United States Patent
Kim et al.

(10) Patent No.: US 10,388,882 B2
(45) Date of Patent: *Aug. 20, 2019

(54) ANTHRACENE DERIVATIVES AND ORGANIC LIGHT EMITTING DEVICES COMPRISING THE SAME

(71) Applicants: SAMSUNG DISPLAY CO., LTD., Yongin, Gyeonggi-Do (KR); SFC CO., LTD., Cheongwon-Gun, Chungcheongbuk (KR)

(72) Inventors: Mi-Kyung Kim, Yongin (KR); Kwan-Hee Lee, Yongin (KR); Yeon-Kwon Ryu, Cheongwon-Gun (KR); Ji-Young Kim, Cheongwon-Gun (KR)

(73) Assignees: Samsung Display Co., Ltd., Yongin-si (KR); SFC Co., Ltd., Cheongwon-Gun (KR)

( * ) Notice: Subject to any disclaimer, the term of this patent is extended or adjusted under 35 U.S.C. 154(b) by 359 days.

This patent is subject to a terminal disclaimer.

(21) Appl. No.: 14/195,836

(22) Filed: Mar. 3, 2014

(65) Prior Publication Data

US 2014/0246657 A1    Sep. 4, 2014

(30) Foreign Application Priority Data

Mar. 4, 2013   (KR) .................. 10-2013-0022833

(51) Int. Cl.
   *C09K 11/06*   (2006.01)
   *H01L 51/00*   (2006.01)
   (Continued)

(52) U.S. Cl.
   CPC ........ *H01L 51/0058* (2013.01); *C07B 59/001* (2013.01); *C07C 13/567* (2013.01);
   (Continued)

(58) Field of Classification Search
   CPC ..... C07B 59/001; C07C 13/567; C07C 13/66; C07C 15/28; C07C 15/30; C07C 15/38;
   (Continued)

(56) References Cited

U.S. PATENT DOCUMENTS 3,968,051 A    7/1976   Stamm et al.
5,635,308 A    6/1997   Inoue et al.
(Continued)

FOREIGN PATENT DOCUMENTS

CN    102925139 A    2/2013
JP    8-12600 A    1/1996
(Continued)

OTHER PUBLICATIONS

Machine translation for JP 2012-119592 A (publication date: Jun. 2012).*

(Continued)

*Primary Examiner* — Dawn L. Garrett
(74) *Attorney, Agent, or Firm* — Lewis Roca Rothgerber Christie LLP

(57) ABSTRACT

An anthracene derivative represented by Formula 1 is disclosed. An organic light-emitting device including an anode, a cathode, and an organic layer between the anode and the cathode, where the organic layer includes at least one anthracene derivative represented by Formula 1, is also disclosed. A method of manufacturing the organic light- (Continued)

| 80 |
|----|
| 70 |
| 60 |
| 50 |
| 40 |
| 30 |
| 20 |
| 10 | emitting device is also disclosed.

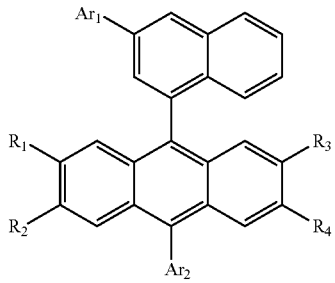

Formula 1

5 Claims, 3 Drawing Sheets

(51) Int. Cl.
| | |
|---|---|
| *H01L 51/50* | (2006.01) |
| *C07F 7/08* | (2006.01) |
| *C07B 59/00* | (2006.01) |
| *C07C 13/567* | (2006.01) |
| *C07C 13/66* | (2006.01) |
| *C07C 15/28* | (2006.01) |
| *C07C 15/30* | (2006.01) |
| *C07C 15/38* | (2006.01) |
| *C07C 15/60* | (2006.01) |
| *C07D 213/16* | (2006.01) |

(52) U.S. Cl.
CPC .............. *C07C 13/66* (2013.01); *C07C 15/28* (2013.01); *C07C 15/30* (2013.01); *C07C 15/38* (2013.01); *C07C 15/60* (2013.01); *C07D 213/16* (2013.01); *C07F 7/0805* (2013.01); *C09K 11/06* (2013.01); *C07C 2103/18* (2013.01); *C07C 2103/24* (2013.01); *C07C 2103/26* (2013.01); *C07C 2103/40* (2013.01); *C07C 2103/50* (2013.01); *C09K 2211/1011* (2013.01); *H01L 51/006* (2013.01); *H01L 51/0054* (2013.01); *H01L 51/0081* (2013.01); *H01L 51/5012* (2013.01)

(58) Field of Classification Search
CPC . C07C 15/60; C07C 2103/18; C07C 2103/24; C07C 2103/26; C07C 2103/40; C07C 2103/50; C07D 213/16; C07F 7/0809; C09K 11/06; C09K 2211/1011
See application file for complete search history.

(56) References Cited

U.S. PATENT DOCUMENTS

| | | | |
|---|---|---|---|
| 5,972,247 | A | 10/1999 | Shi et al. |
| 6,465,115 | B2 | 10/2002 | Shi et al. |
| 6,582,837 | B1 | 6/2003 | Toguchi et al. |
| 6,596,415 | B2 | 7/2003 | Shi et al. |
| 7,053,255 | B2 | 5/2006 | Ikeda et al. |
| 7,233,019 | B2 | 6/2007 | Ionkin et al. |
| 7,732,063 | B2 | 6/2010 | Matsuura et al. |
| 7,839,074 | B2 | 11/2010 | Ikeda et al. |
| 8,221,905 | B2 | 7/2012 | Lin et al. |
| 8,324,802 | B2 | 12/2012 | Matsuura et al. |
| 8,334,648 | B2 | 12/2012 | Matsuura et al. |
| 9,680,108 | B2 * | 6/2017 | Ito ................ H01L 51/0058 |
| 9,711,736 | B2 | 7/2017 | Han et al. |
| 9,893,289 | B2 * | 2/2018 | Ito ................ H01L 51/0052 |
| 10,062,850 | B2 * | 8/2018 | Jung ............. H01L 51/0058 |
| 10,193,074 | B2 * | 1/2019 | Hwang .......... H01L 51/0058 |
| 10,193,078 | B2 * | 1/2019 | Ito ................ H01L 51/0072 |
| 2004/0076853 | A1 * | 4/2004 | Jarikov ............. C09K 11/06 428/690 |
| 2004/0137270 | A1 * | 7/2004 | Seo ................. C09K 11/06 428/690 |
| 2004/0214036 | A1 | 10/2004 | Bentsen et al. |
| 2005/0064233 | A1 | 3/2005 | Matsuura et al. |
| 2005/0089717 | A1 | 4/2005 | Cosimbescu et al. |
| 2005/0156164 | A1 | 7/2005 | Sotoyama |
| 2005/0214565 | A1 | 9/2005 | Ikeda et al. |
| 2005/0245752 | A1 | 11/2005 | Conley et al. |
| 2005/0249972 | A1 | 11/2005 | Hatwar et al. |
| 2006/0052641 | A1 | 3/2006 | Funahashi |
| 2006/0083945 | A1 | 4/2006 | Morishita et al. |
| 2006/0113905 | A1 | 6/2006 | Nakamura |
| 2006/0152146 | A1 | 7/2006 | Funahashi |
| 2006/0159952 | A1 * | 7/2006 | Ricks .............. C09K 11/06 428/690 |
| 2007/0114917 | A1 | 5/2007 | Funahashi et al. |
| 2007/0152565 | A1 * | 7/2007 | Kubota ............ C07C 15/28 313/504 |
| 2007/0155991 | A1 | 7/2007 | Funahashi |
| 2007/0170419 | A1 | 7/2007 | Gerhard et al. |
| 2007/0237984 | A1 | 10/2007 | Matsuura et al. |
| 2008/0160342 | A1 | 7/2008 | Meng et al. |
| 2008/0193796 | A1 * | 8/2008 | Arakane ........... C09K 11/06 428/690 |
| 2009/0004458 | A1 | 1/2009 | Falster et al. |
| 2009/0004485 | A1 | 1/2009 | Zheng et al. |
| 2009/0026930 | A1 | 1/2009 | Shin et al. |
| 2010/0013381 | A1 | 1/2010 | Stoessel et al. |
| 2010/0032658 | A1 | 2/2010 | Lee et al. |
| 2010/0052526 | A1 | 3/2010 | Je et al. |
| 2010/0127618 | A1 | 5/2010 | Ohrui et al. |
| 2010/0187521 | A1 | 7/2010 | Park et al. |
| 2010/0244012 | A1 | 9/2010 | Mazur et al. |
| 2010/0270913 | A1 | 10/2010 | Matsuura et al. |
| 2010/0277061 | A1 | 11/2010 | Matsuura et al. |
| 2010/0279156 | A1 | 11/2010 | Kim et al. |
| 2010/0295445 | A1 | 11/2010 | Kuma et al. |
| 2010/0314615 | A1 | 12/2010 | Mizuki et al. |
| 2011/0001130 | A1 | 1/2011 | Nishimura et al. |
| 2011/0006289 | A1 | 1/2011 | Mizuki et al. |
| 2011/0057116 | A1 | 3/2011 | Trogler et al. |
| 2011/0156016 | A1 | 6/2011 | Kawamura et al. |
| 2011/0210320 | A1 | 9/2011 | Shin et al. |
| 2011/0284832 | A1 | 11/2011 | In et al. |
| 2012/0001158 | A1 | 1/2012 | Asari et al. |
| 2012/0032152 | A1 | 2/2012 | Kim et al. |
| 2012/0056165 | A1 | 3/2012 | Kawamura et al. |
| 2012/0091885 | A1 | 4/2012 | Kim et al. |
| 2012/0138915 | A1 | 6/2012 | Nishimura et al. |
| 2012/0181518 | A1 | 7/2012 | Ogiwara et al. |
| 2012/0181922 | A1 | 7/2012 | Kawamura et al. |
| 2012/0235561 | A1 | 9/2012 | Ikeda et al. |
| 2012/0305904 | A1 | 12/2012 | Kai et al. |
| 2012/0313511 | A1 | 12/2012 | Tsurutani et al. |
| 2013/0001526 | A1 | 1/2013 | Kwak et al. |
| 2013/0049581 | A1 | 2/2013 | Nishide et al. |
| 2013/0090446 | A1 | 4/2013 | Zhou et al. |
| 2013/0105786 | A1 | 5/2013 | Watanabe et al. |
| 2013/0112949 | A1 | 5/2013 | Sim et al. |
| 2013/0119355 | A1 | 5/2013 | Han et al. |
| 2013/0221332 | A1 | 8/2013 | Xia et al. |
| 2013/0228752 | A1 | 9/2013 | Shin et al. |
| 2013/0295706 | A1 | 11/2013 | Goto et al. |
| 2013/0306958 | A1 | 11/2013 | Ito et al. |
| 2014/0008641 | A1 | 1/2014 | Kubota et al. |
| 2014/0048792 | A1 | 2/2014 | Chun et al. |
| 2014/0124763 | A1 | 5/2014 | Funahashi |
| 2014/0175395 | A1 | 6/2014 | Kim et al. |
| 2014/0264301 | A1 | 9/2014 | Takaku et al. |
| 2014/0332772 | A1 | 11/2014 | Han et al. |
| 2014/0346406 | A1 | 11/2014 | Lee et al. |
| 2014/0346464 | A1 | 11/2014 | Kim et al. |
| 2014/0346482 | A1 | 11/2014 | Mizuki et al. |

(56) References Cited

U.S. PATENT DOCUMENTS

| | | | |
|---|---|---|---|
| 2015/0001479 A1* | 1/2015 | Lee | H01L 51/0073 257/40 |
| 2015/0053946 A1 | 2/2015 | Kim et al. | |
| 2015/0069344 A1 | 3/2015 | Kim et al. | |
| 2015/0090964 A1 | 4/2015 | Hwang et al. | |
| 2015/0090965 A1 | 4/2015 | Park et al. | |
| 2015/0108448 A1 | 4/2015 | Dai et al. | |
| 2015/0171337 A1* | 6/2015 | Jung | H01L 51/0058 257/40 |
| 2015/0236273 A1 | 8/2015 | Jang et al. | |
| 2015/0255736 A1* | 9/2015 | Kim | H01L 51/0061 257/40 |
| 2015/0318508 A1 | 11/2015 | Kim et al. | |
| 2015/0333266 A1* | 11/2015 | Ito | H01L 51/0052 257/40 |
| 2015/0333268 A1 | 11/2015 | Han et al. | |
| 2015/0349265 A1* | 12/2015 | Hwang | H01L 51/0058 257/40 |
| 2015/0357574 A1* | 12/2015 | Ito | H01L 51/0052 257/40 |
| 2015/0364693 A1* | 12/2015 | Ito | H01L 51/0058 257/40 |
| 2016/0005980 A1* | 1/2016 | Ito | H01L 51/0072 257/40 |
| 2016/0020404 A1* | 1/2016 | Ito | H01L 51/0067 257/40 |

FOREIGN PATENT DOCUMENTS

| | | |
|---|---|---|
| JP | 11-003782 A | 1/1999 |
| JP | 2002-63989 | 2/2002 |
| JP | 2003-306454 | 10/2003 |
| JP | 2005-041843 A | 2/2005 |
| JP | 2006-273737 A | 10/2006 |
| JP | 2007-63501 A | 3/2007 |
| JP | 2007-77094 A | 3/2007 |
| JP | 2008-291263 | 12/2008 |
| JP | 2009-212238 | 9/2009 |
| JP | 2011-176267 A | 9/2011 |
| JP | 2012-82209 | 4/2012 |
| JP | 2012-119592 A | 6/2012 |
| JP | 2012-156499 A | 8/2012 |
| JP | 2013-063930 | 4/2013 |
| JP | 2013-063931 | 4/2013 |
| JP | 5281304 | 5/2013 |
| JP | 52-08271 B2 | 6/2013 |
| KR | 10-2005-0058465 | 6/2005 |
| KR | 10-2005-086518 | 8/2005 |
| KR | 10-2005-0107809 | 11/2005 |
| KR | 10-2006-0006760 | 1/2006 |
| KR | 10-2006-0109524 | 10/2006 |
| KR | 10-2006-0113954 | 11/2006 |
| KR | 10-2006-0127138 | 12/2006 |
| KR | 10-2007-0009074 | 1/2007 |
| KR | 10-2007-0015195 | 2/2007 |
| KR | 10-2007-0050393 A | 5/2007 |
| KR | 10-2008-0068720 A | 7/2008 |
| KR | 10-2009-0010763 A | 1/2009 |
| KR | 10-2009-0033493 | 4/2009 |
| KR | 10-2009-0122922 A | 12/2009 |
| KR | 10-2010-0007552 | 1/2010 |
| KR | 10-2010-0007780 | 1/2010 |
| KR | 10-2010-0024894 | 3/2010 |
| KR | 10-2010-0048203 | 5/2010 |
| KR | 10-2010-0057465 | 5/2010 |
| KR | 10-2010-0070979 | 6/2010 |
| KR | 10-2010-0070992 | 6/2010 |
| KR | 10-2010-0093085 | 8/2010 |
| KR | 10-2010-0097182 | 9/2010 |
| KR | 10-2010-0099327 | 9/2010 |
| KR | 10-2010-0105099 | 9/2010 |
| KR | 10-2011-0015213 | 2/2011 |
| KR | 10-2011-0041728 | 4/2011 |
| KR | 10-2011-0043625 A | 4/2011 |
| KR | 1-0047278 A | 5/2011 |
| KR | 10-2011-0094271 | 8/2011 |
| KR | 10-2011-0107679 | 10/2011 |
| KR | 10-2011-0134885 | 12/2011 |
| KR | 10-2012-0002865 | 1/2012 |
| KR | 10-2012-0026513 | 3/2012 |
| KR | 10-2012-0039470 | 4/2012 |
| KR | 10-2012-0041110 | 4/2012 |
| KR | 10-1132635 B1 | 4/2012 |
| KR | 10-2012-0057611 | 6/2012 |
| KR | 10-2012-0066390 | 6/2012 |
| KR | 10-2012-0093354 | 8/2012 |
| KR | 10-2012-0117622 | 10/2012 |
| KR | 10-2012-0117675 | 10/2012 |
| KR | 10-2013-0007495 | 1/2013 |
| KR | 10-2013-0009765 | 1/2013 |
| KR | 10-1233377 | 2/2013 |
| KR | 10-1262420 | 5/2013 |
| KR | 10-2013-0100948 | 9/2013 |
| WO | WO 2010/050781 A1 | 5/2010 |
| WO | WO 2010/058995 A1 | 5/2010 |
| WO | WO 2010/107244 A2 | 9/2010 |
| WO | WO 2010/137678 A1 | 12/2010 |
| WO | WO 2012/070226 A1 | 5/2012 |
| WO | WO 2012/070234 A1 | 5/2012 |
| WO | WO 2013/051875 A2 | 4/2013 |

OTHER PUBLICATIONS

Zhensheng, et al., A Succinct Synthesis of the Vaulted Biaryl Ligand Vanol via a Dienone-Phenol Rearrangement, Full Papers, 2011 Wiley-VCH Verlag GmbH & Co., KGaA, Weinheim, Chem. Asian J. 2011, 6,2130-2146, 17 pages.
Katritzky, A., et al., Polycyclic Fused Phenanthridines: An Alternative Approach from Benzotriazoles, Center for Heterocyclic Compounds., Department of Chemistry, Univ. of Florida, pp. 1-27 (No Date Provided).
Notice of Allowance dated Jul. 15, 2016, for cross reference U.S. Appl. No. 14/533,004.
STIC Search Report for cross reference U.S. Appl. No. 14/533,004, dated Dec. 1, 2015 (15 pages).
U.S. Office action dated Dec. 8, 2015, for cross reference U.S. Appl. No. 14/533,004, (12 pages).
U.S. Office action dated Feb. 19, 2016, for cross reference U.S. Appl. No. 14/072,478, (12 pages).
U.S. Office Action dated Apr. 20, 2016, issued in cross-reference U.S. Appl. No. 14/075,573 (10 pages).
Leem et al., "Highly efficient tandem p-i-n. organic light-emitting diodes adopting a low temperature evaporated rhenium oxide interconnecting later," Applied Physics Letters, 93, 103304-1-3, 2008.
Kaminaga, et al., Machine Translation of JP 2011-176267A, Published Sep. 2011, Retrieved from Google Patents on Feb. 3, 2017, pp. 1-44.
Yumiko et al., Machine English translation of KR 10-2010-0097182. Mar. 10, 2017.
U.S. Notice of Allowance dated Feb. 10, 2017, issued in cross-reference U.S. Appl. No. 14/533,004 (12 pages).
U.S. Office Action dated Feb. 16, 2017, issued in cross-reference U.S. Appl. No. 14/075, 573 (14 pages).
U.S. Notice of Allowance dated Mar. 27, 2017, issued in cross-reference U.S. Appl. No. 14/550,801 (9 pages).
Machine translation for JP 2012-119592 A, publication date Jun. 21, 2012, 27 pages.
Machine Translation for KR 10-2011-0041728, publication date Apr. 22, 2011, 19 pages.
U.S. Office Action dated Jul. 13, 2017, issued in cross-reference U.S. Appl. No. 14/508,677 (10 pages).
U.S. Office Action dated May 18, 2017, issued in cross-reference U.S. Appl. No. 14/789,672 (18 pages).
Machine English translation of Shin et al. (KR 10-2009-0010763), 27 pages Year: 2009.
U.S. Notice of Allowance dated Mar. 15, 2017, issued in U.S. Appl. No. 14/513,144 (9 pages).

(56) References Cited

OTHER PUBLICATIONS

U.S. Office Action dated Aug. 23, 2017, issued in U.S. Appl. No. 14/702,970 (9 pages).
U.S. Office Action dated Sep. 7, 2017, issued in U.S. Appl. No. 14/789,672 (16 pages.).
U.S. Notice of Allowance dated Jan. 25, 2018, issued in U.S. Patent Application No. 14/075,573 (8 pages).
U.S. Notice of Allowance dated Mar. 13, 2018, issued in U.S. Appl. No. 14/789,672 (10 pages).
U.S. Office Action dated Dec. 18, 2017, issued in U.S. Appl. No. 14/550,801 (9 pages).

* cited by examiner

ANTHRACENE DERIVATIVES AND ORGANIC LIGHT EMITTING DEVICES COMPRISING THE SAME

CROSS-REFERENCE TO RELATED APPLICATION

This application claims priority to and the benefit of Korean Patent Application No. 10-2013-0022833, filed on Mar. 4, 2013 in the Korean Intellectual Property Office, the entire content of which is incorporated herein by reference.

BACKGROUND

1. Technical Field

One or more aspects according to embodiments of the present invention relate to organic light-emitting compounds and organic light-emitting devices including the organic light-emitting compounds, for example, anthracene derivatives and organic light-emitting devices including the anthracene derivatives.

2. Description of the Related Art

In an organic light-emitting device, materials used for an organic material layer may be categorized into an emission material or a charge-transporting material, depending on the function of the material used. Examples of charge-transporting materials include a hole-injecting material, a hole-transporting material, an electron-transporting material, and an electron-injecting material. The emission material may be categorized into a polymer-type or a low molecular weight type, depending on a molecular weight thereof. The emission material may be further categorized into a fluorescent material (e.g., a material having a singlet excited state of an electron) or a phosphorescent material (e.g., a material having a triplet excited state of an electron), depending on the emission mechanism thereof. Also, the emission material may be categorized into yellow or orange emission materials, depending on the color emitted, which are used to achieve more natural colors than blue, green, and red emission materials.

Meanwhile, when only one material is used as the emission material, problems, such as the occurrence of a molecular interaction, which causes a movement of a maximum emission wavelength as long-wavelength (e.g., a shift to a longer wavelength), decreased color purity, or decreased emission, may occur which reduce the efficiency of a device. Thus, a host-dopant system may be used for the emission material to improve emission efficiency through improved energy transfer and to increase color purity.

When a small amount of a dopant having a smaller energy band gap than a host of the emission layer is mixed into the emission layer, excitons generated in the emission layer are transported to the dopant to emit high efficiency light. In this regard, a wavelength of the host moves (or shifts) according to a wavelength of the dopant and thus, light of a desired wavelength may be obtained according to the type of the dopant.

For an organic light-emitting device to show good characteristics as described above, materials included in the organic material layer of the device, such as a hole-injecting material, a hole-transporting material, an emission material, an electron-transporting material, and/or an electron-injecting material need to be stable and efficient materials; however, there has not been sufficient development of a stable and efficient material for the organic material layer of the organic light-emitting device. Accordingly, development of a new material is continuously being pursued in the art.

For example, a phenanthryl anthracene derivative can be used as a host material. Such anthracene derivative can be used as a blue emission material; however, a driving voltage of the device using such an anthracene derivative needs to be improved. Also, a compound in which an anthracene ring and a naphthyl ring are directly connected can be used in a light-emitting device; however, lifespan characteristics of a device using the compound need to be improved for the commercialization thereof. Accordingly, there is a need to develop a good material for low driving voltage, improved emission efficiency, and long lifespan characteristics of an organic light-emitting device.

SUMMARY

One or more aspects according to embodiments of the present invention are directed toward an anthracene derivative and an organic light-emitting device including the anthracene derivative.

Additional aspects are set forth in part in the description which follows and, in part, will be apparent from the description, or may be learned by practice of the presented embodiments.

According to one or more embodiments of the present invention, an anthracene derivative is represented by Formula 1.

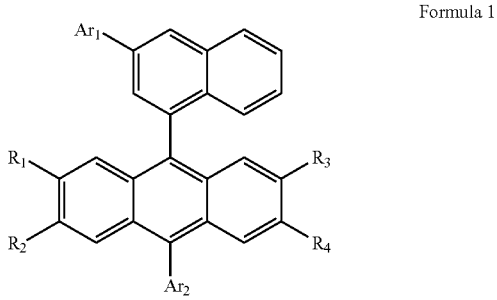

Formula 1

The substituents of Formula 1 and the anthracene derivative compound are as described below.

According to one or more embodiments of the present invention, an organic light-emitting device includes an anode, a cathode, and an organic layer between the anode and the cathode, where the organic layer includes at least one anthracene derivative represented by Formula 1.

BRIEF DESCRIPTION OF THE DRAWINGS

These and/or other aspects will become apparent and more readily appreciated by reference to the following detailed description when considered together with the accompanying drawings in which.

DETAILED DESCRIPTION

Figure 1:
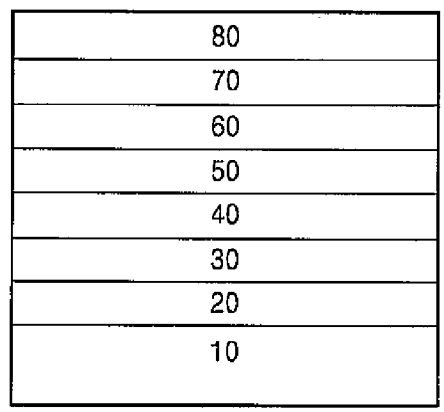
FIG. 1 is a cross-sectional view of a layer structure of an organic light-emitting device according to an embodiment of the present invention.

Reference will now be made to certain embodiments, examples of which are illustrated in the accompanying drawings, where like reference numerals refer to like elements throughout. As those skilled in the art would recognize, the described embodiments may be modified in many ways and, therefore, should not be construed as limiting. Accordingly, the embodiments are described below, by referring to the figures, merely to explain aspects of the present description. Expressions such as "at least one of," when preceding a list of elements, modify the entire list of elements and do not modify the individual elements of the list.

Hereinafter, embodiments of the present invention will be described in greater detail.

An anthracene derivative according to an embodiment of the present invention may be represented by Formula 1 below:

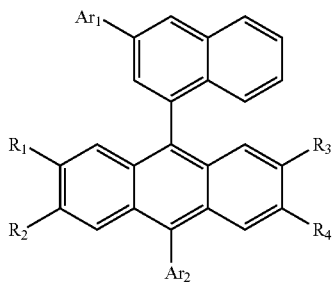

Formula 1

In Formula 1, $Ar_1$ and $Ar_2$ may be the same or different, and may be each independently a substituted or unsubstituted C6-C50 aryl group or a substituted or unsubstituted C3-C50 heteroaryl group having O, N, or S as a heteroatom.

Also, $R_1$ to $R_4$ may be the same or different, and may be each independently a hydrogen atom, a deuterium atom, a substituted or unsubstituted C1-C30 alkyl group, a substituted or unsubstituted C2-C30 alkenyl group, a substituted or unsubstituted C3-C30 cycloalkyl group, a substituted or unsubstituted C5-C30 cycloalkenyl group, a substituted or unsubstituted C1-C30 alkoxy group, substituted or unsubstituted C6-C30 aryloxy group, a substituted or unsubstituted C1-C30 alkylthioxy group, a substituted or unsubstituted C5-C30 arylthioxy group, a substituted or unsubstituted C1-C30 alkylamine group, a substituted or unsubstituted C5-C30 arylamine group, a substituted or unsubstituted C6-C50 aryl group, a substituted or unsubstituted C3-C50 heteroaryl group having O, N or S as a heteroatom, a substituted or unsubstituted silicon group, a substituted or unsubstituted boron group, a substituted or unsubstituted silane group, a carbonyl group, a phosphoryl group, an amino group, a nitrile group, a hydroxy group, a nitro group, a halogen group, an amide group, or an ester group.

Also, $R_1$ and $R_2$ and/or $R_3$ and $R_4$ may, optionally, combine together to form a saturated or an unsaturated ring.

In Formula 1, when $R_1$ to $R_4$, and $Ar_1$ and $Ar_2$ are further substituted with substituents, the substituents may be each independently at least one of a C6-C24 aryl group, a C2-C24 heteroaryl group, a C1-C24 alkyl group, a C1-C24 heteroalkyl group, a C3-C24 cycloalkyl group, a C1-C24 alkoxy group, a cyano group, a halogen group, a C6-C24 aryloxy group, a C1-C24 alkyl silyl group, C6-C24 aryl silyl group, or a deuterium atom, where the substituent may, optionally, combine together with a nearby substituent to form a saturated or an unsaturated ring.

Also, the anthracene derivative of Formula 1 according to an embodiment of the present invention may be any one of compounds represented by Formula 2 to Formula 12 below:

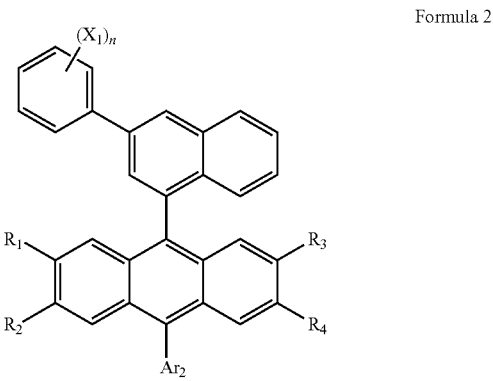

Formula 2

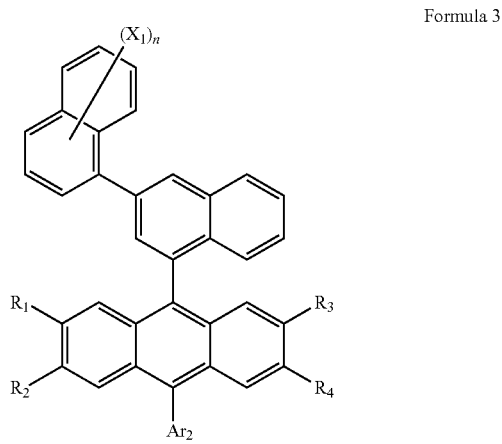

Formula 3

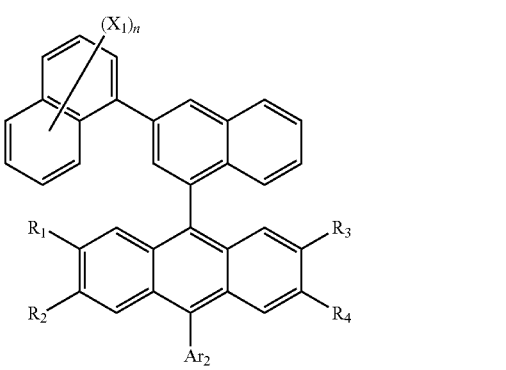

Formula 4

Formula 5
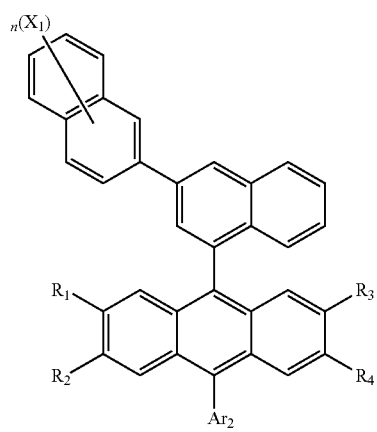
Formula 6
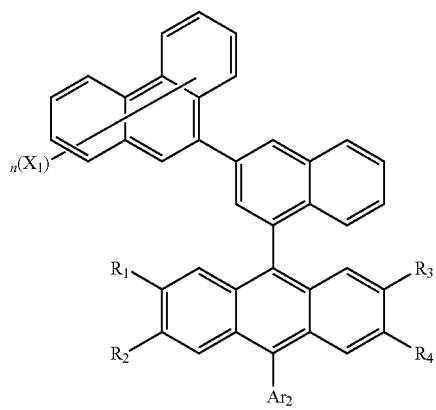
Formula 7
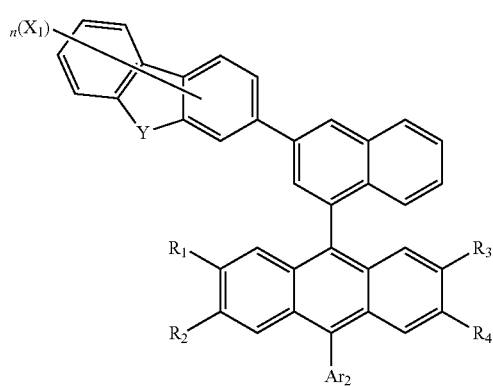
Formula 8
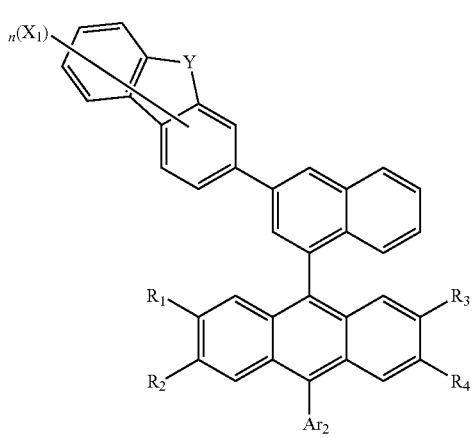
Formula 9
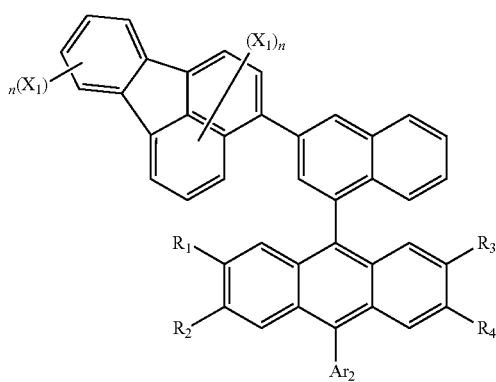
Formula 10
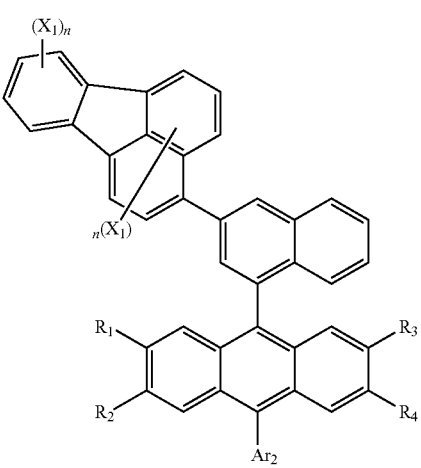

Formula 11

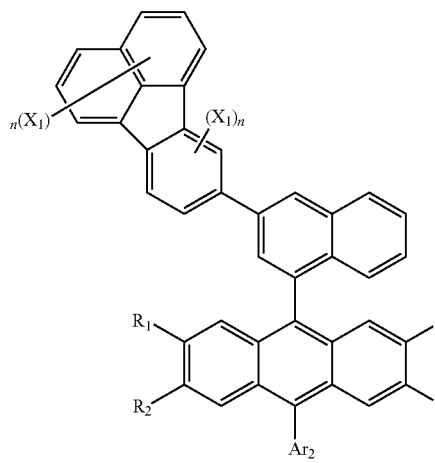

Formula 12

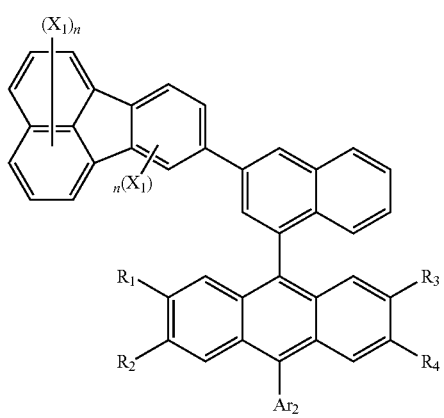

Formula 13

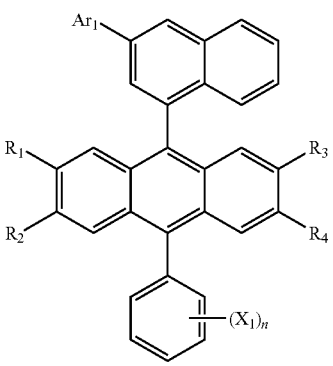

Formula 14

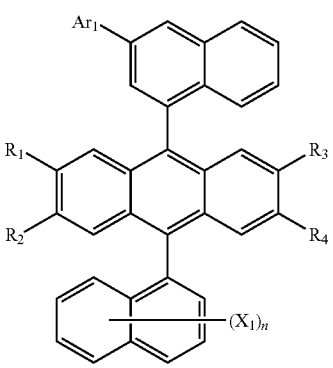

Formula 15

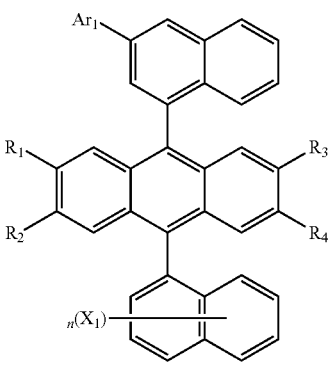

Formula 16

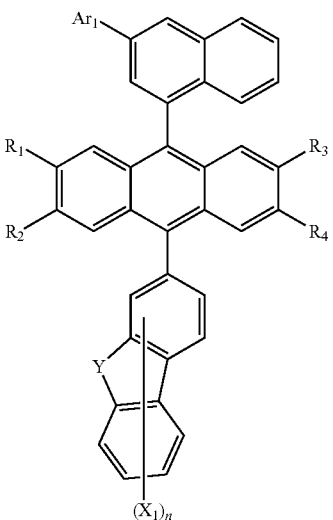

In Formula 2 to Formula 12, $X_1$ may be a hydrogen atom, a deuterium atom, a cyano group, a halogen group, a C1-C24 alkyl group, a C3-C24 cycloalkyl group, a C6-C24 aryl group, a C2-C24 heteroaryl group, a C1-C24 alkoxy group, a C6-C24 aryloxy group, a C1-C24 an alkyl silyl group, or a C6-C24 aryl silyl group.

When n is an integer of 2 or more, a plurality of $X_1$s may be the same or different.

Also, Y may be $CR_5R_6$ or $NR_7$, $Ar_2$ and $R_1$ to $R_4$ may be the same as described above with respect to Formula 1, and $R_5$ to $R_7$ may be the same as described above with respect to $R_1$ to $R_4$ of Formula 1.

According to an embodiment of the present invention, in Formula 2 to Formula 12, at least one carbon atom of a phenyl group, a naphthyl group, a phenanthryl group, a fluorenyl group, or a fluoranthenyl group coupled to a seventh location of the naphthyl group (e.g., bonded to a carbon atom at the seventh position of the naphthyl group), which is coupled to a ninth location of the anthracene (e.g., bonded to a carbon atom at the ninth position of the anthracene), may be each independently substituted with at least one heteroatom of O, N, or S.

Also, the anthracene derivative of Formula 1 according to an embodiment of the present invention may be any one of compounds represented by Formula 13 to Formula 27.

Formula 17
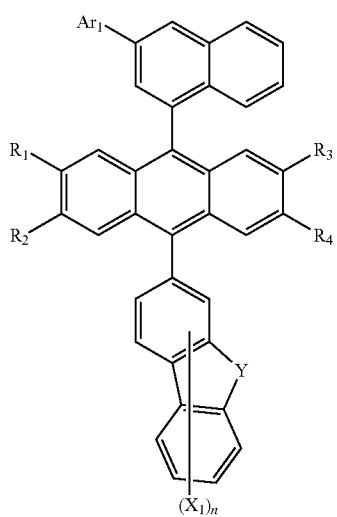
Formula 18
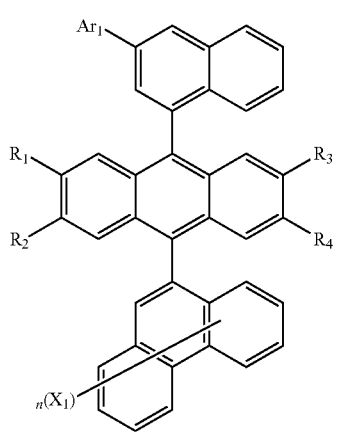
Formula 19
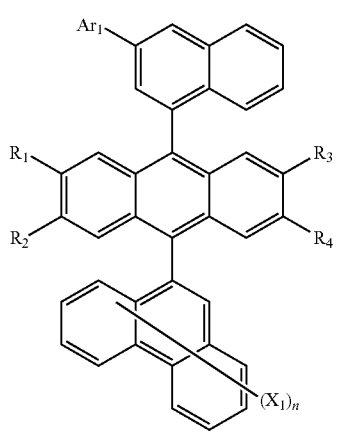
Formula 20
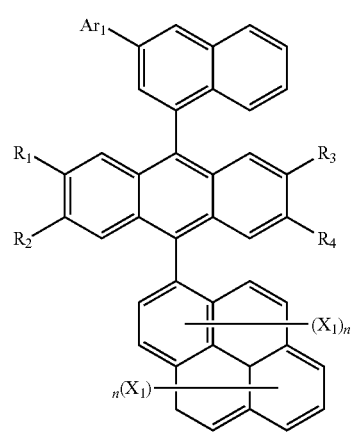
Formula 21
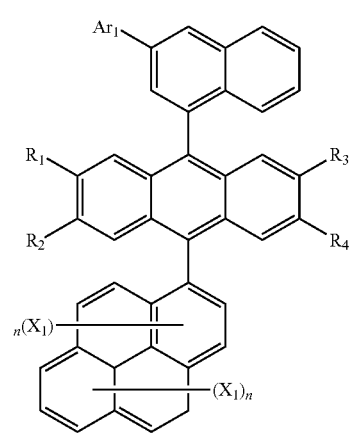
Formula 22
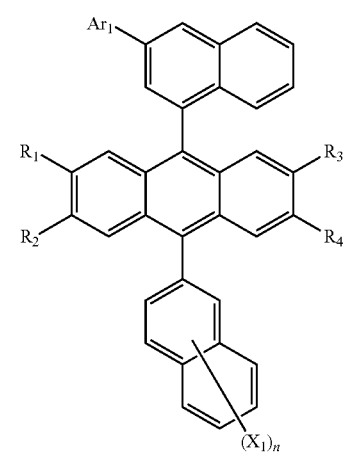

-continued

Formula 23
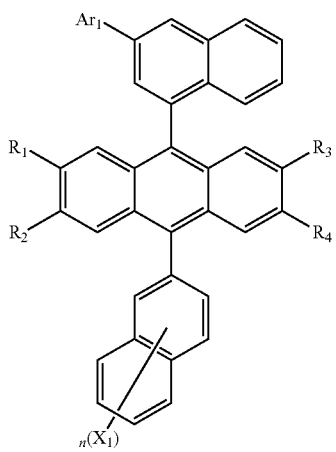

Formula 24
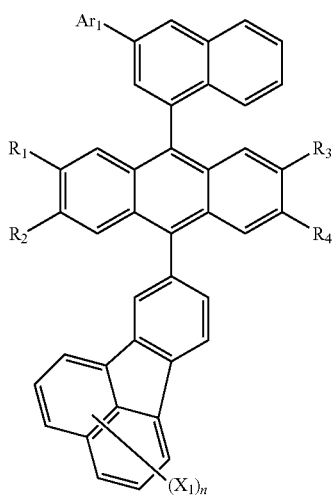

Formula 25
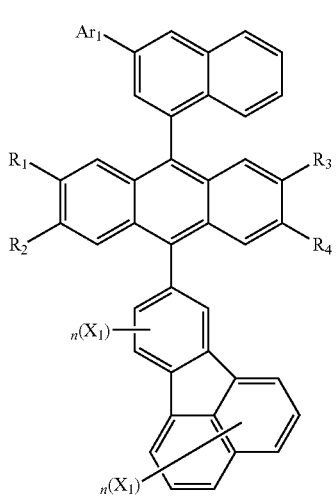

-continued

Formula 26
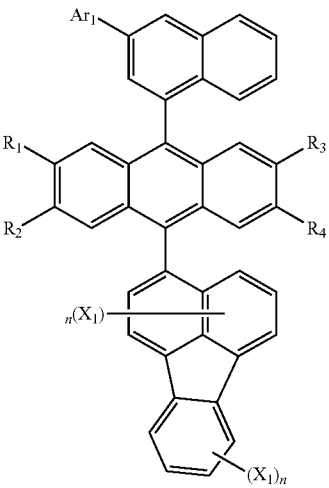

Formula 27
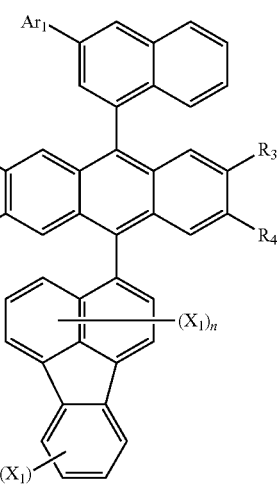

In Formula 13 to Formula 27, $X_1$ may be a hydrogen atom, a deuterium atom, a cyano group, a halogen group, a C1-C24 alkyl group, a C3-C24 cycloalkyl group, a C6-C24 aryl group, a C2-C24 heteroaryl group, a C1-C24 alkoxy group, a C6-C24 aryloxy group, a C1-C24 alkyl silyl group, or a C6-C24 aryl silyl group.

When n is an integer of 2 or more, a plurality of $X_1$s may be each independently the same or different.

Also, Y may be $CR_5R_6$ or $NR_7$, $Ar_1$ and $R_1$ to $R_4$ may be the same as described above with respect to Formula 1, and $R_5$ to $R_7$ may be the same as described above with respect to $R_1$ to $R_4$ of Formula 1.

According to an embodiment of the present invention, in Formula 13 to Formula 27, at least one carbon atom of a phenyl group, a naphthyl group, a phenanthryl group, a pyrenyl group, a fluorenyl group, or a fluoranthenyl group coupled to a tenth location of the anthracene (e.g., bonded to a carbon atom at the tenth position of the anthracene) may be each independently substituted with at least one heteroatom of O, N, or S.

An anthracene derivative represented by Formula 1 according to an embodiment of the present invention may be any one of compounds represented by Formula 28 to Formula 107.

Formula 28
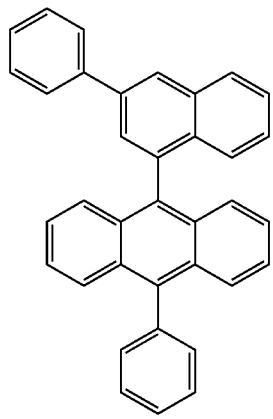
Formula 29
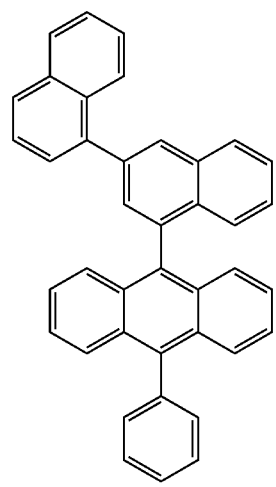
Formula 30
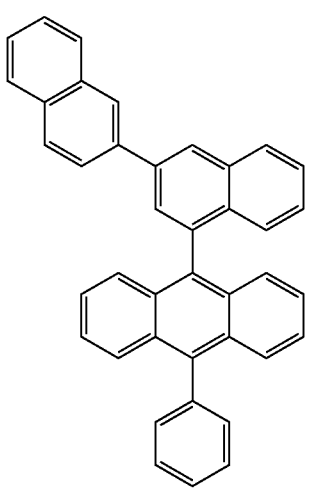
Formula 31
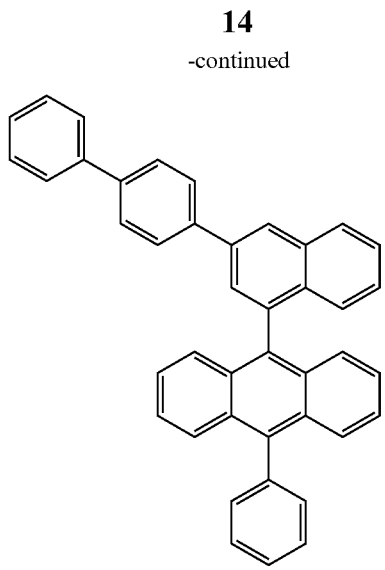
Formula 32
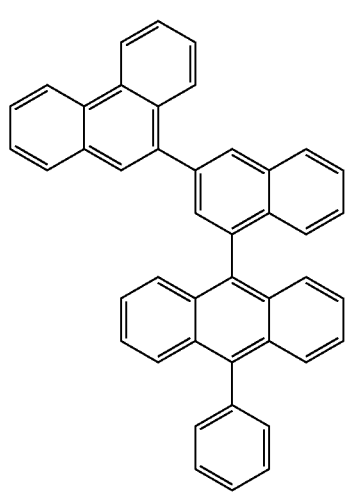
Formula 33
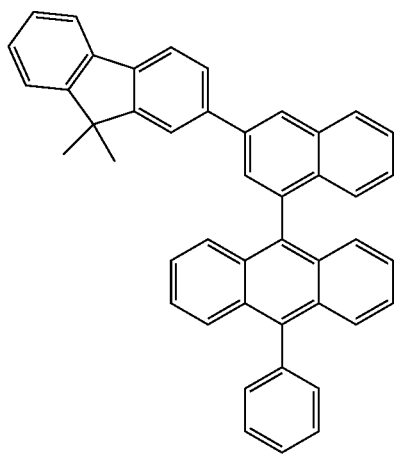

Formula 34
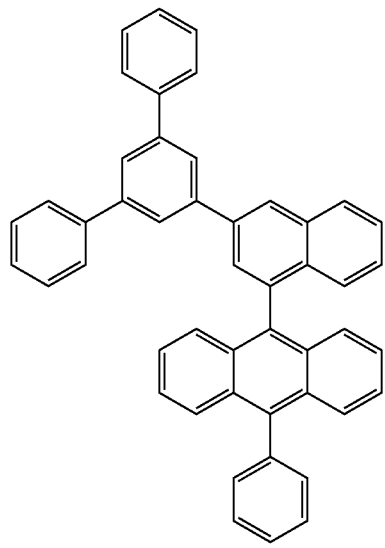
Formula 35
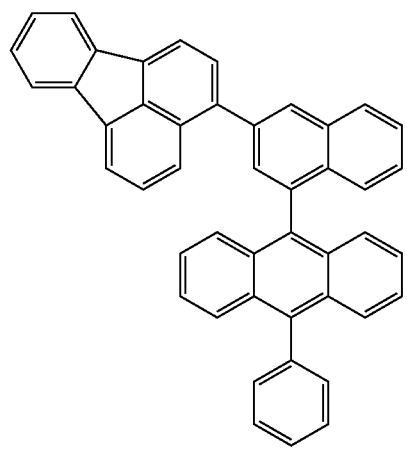
Formula 36
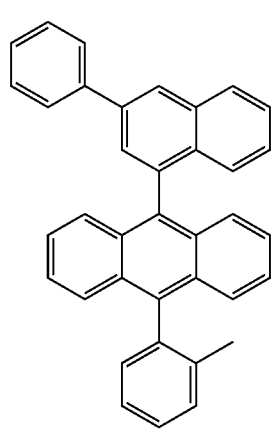
Formula 37
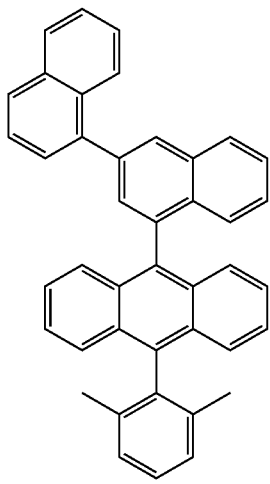
Formula 38
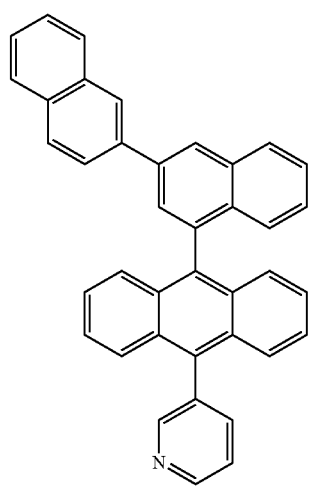
Formula 39
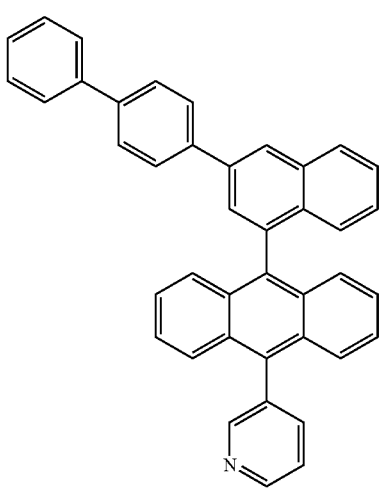

Formula 40
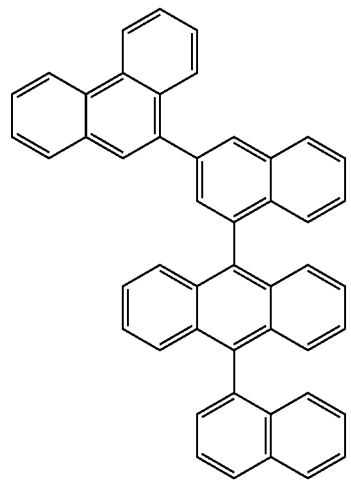
Formula 41
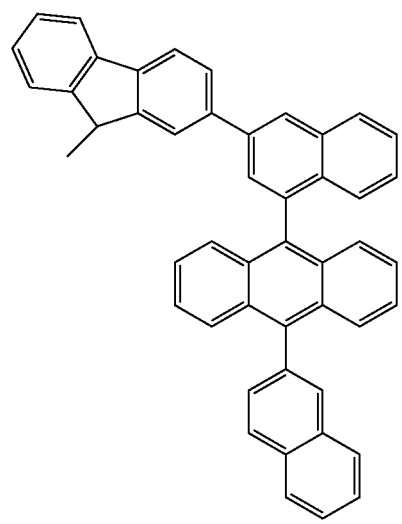
Formula 42
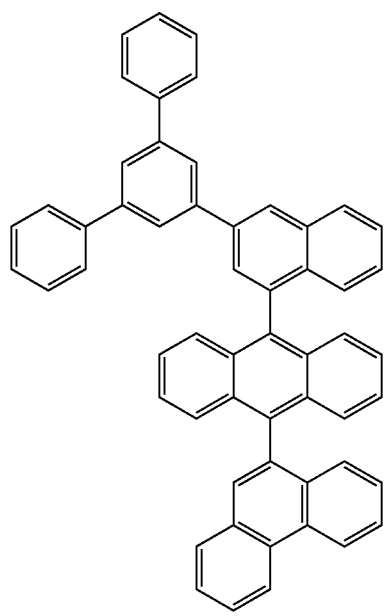
Formula 43
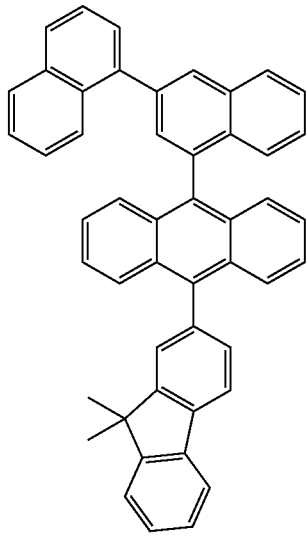
Formula 44
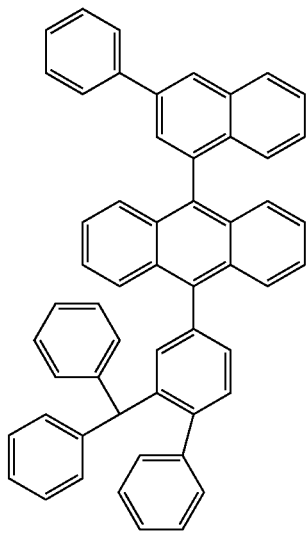
Formula 45
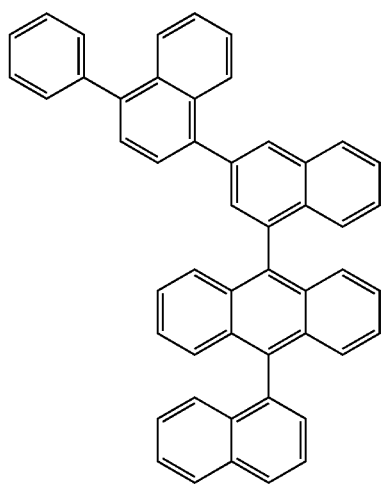

Formula 46
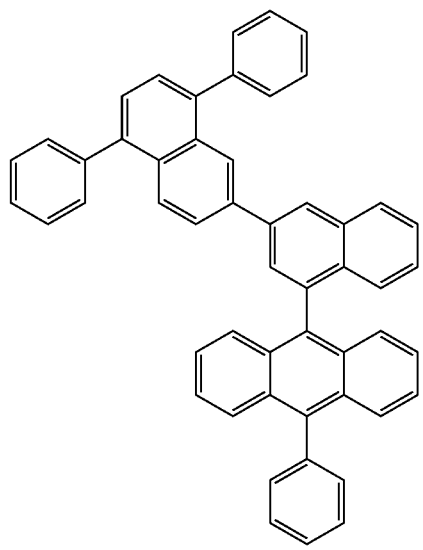
Formula 47
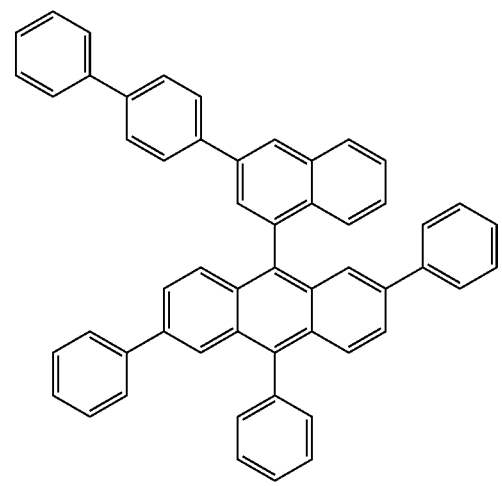
Formula 48
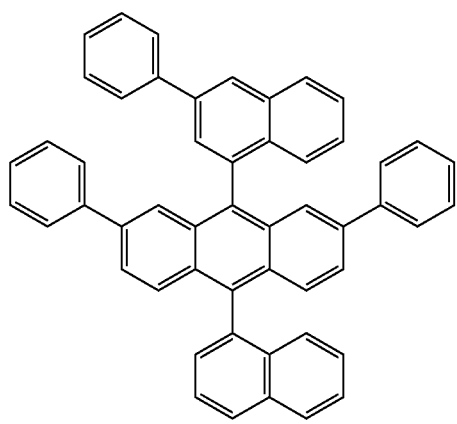
Formula 49
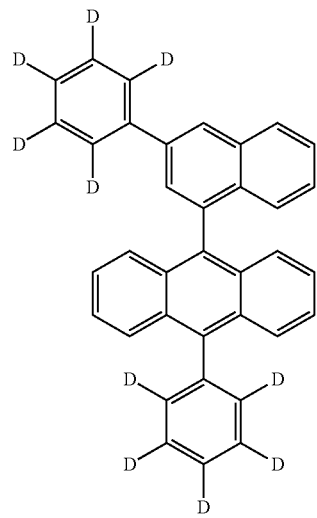
Formula 50
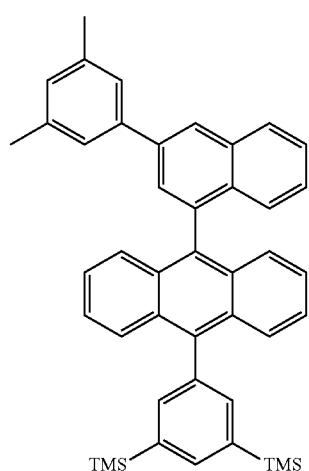
Formula 51
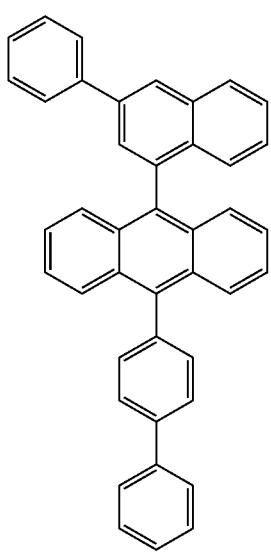

Formula 52
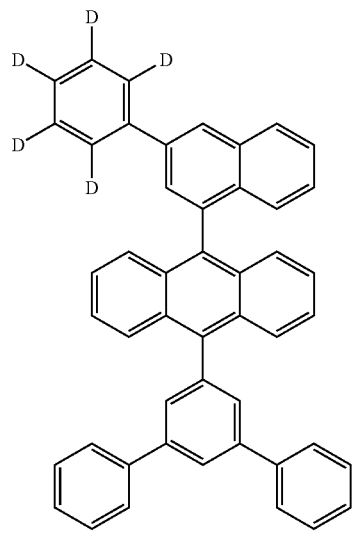
Formula 53
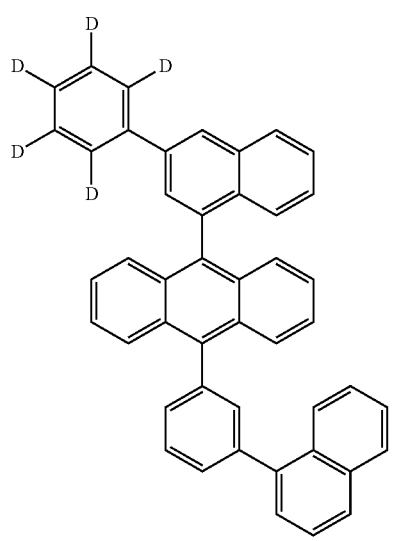
Formula 54
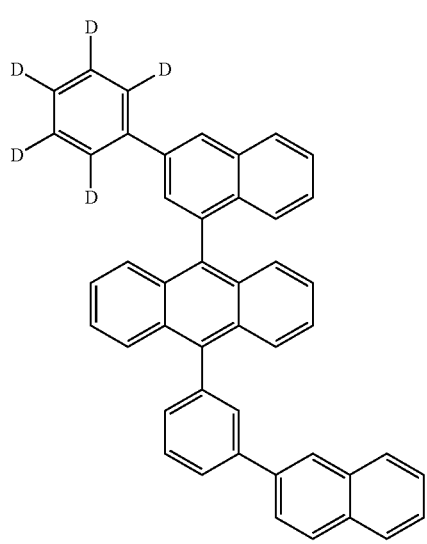
Formula 55
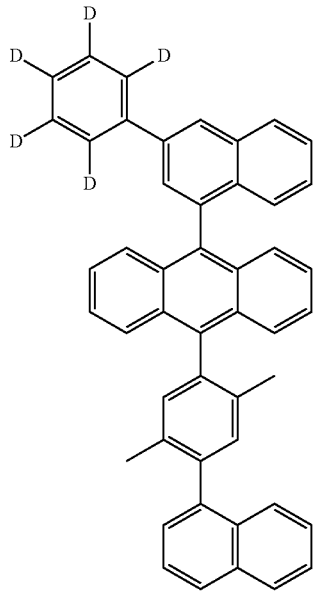
Formula 56
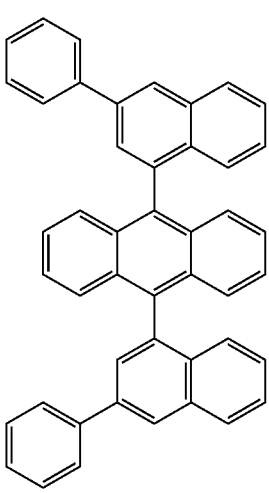
Formula 57
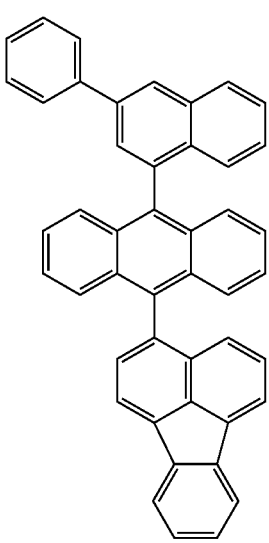

-continued
Formula 58
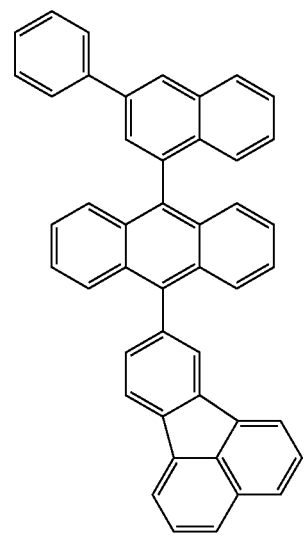
Formula 59
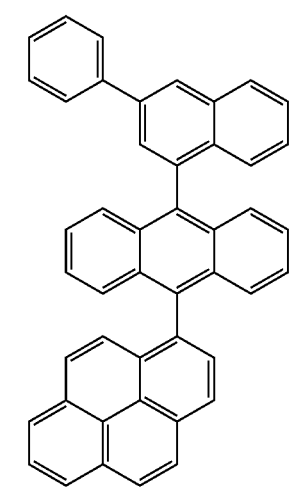
Formula 60
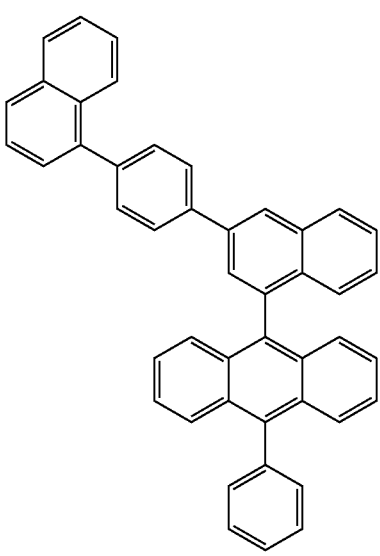
-continued
Formula 61
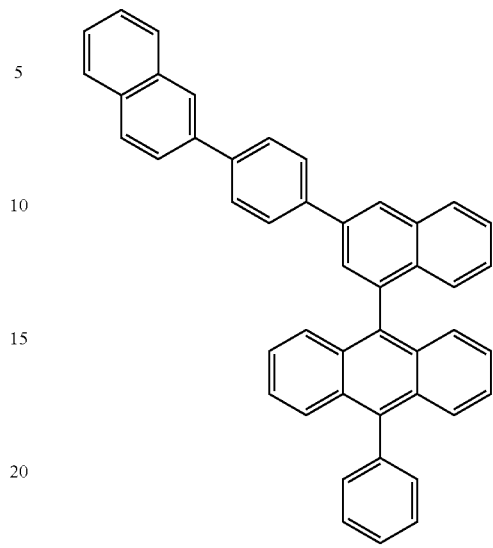
Formula 62
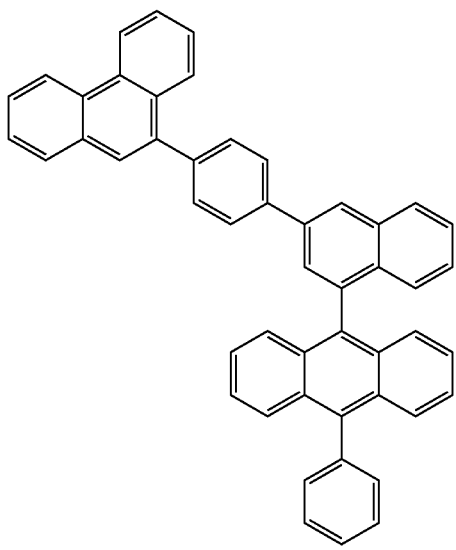
Formula 63
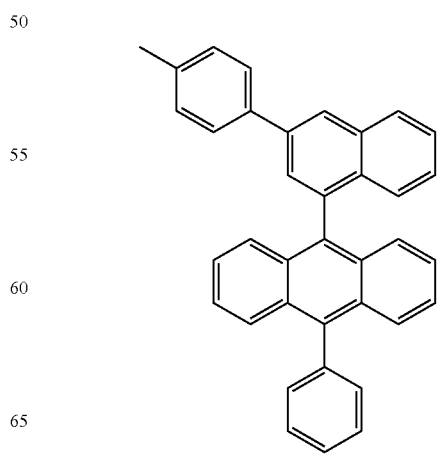

Formula 64
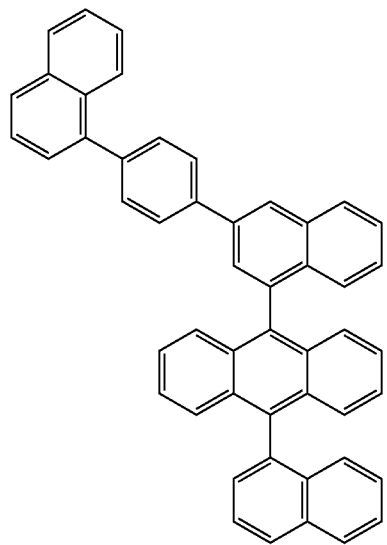
Formula 65
Formula 66
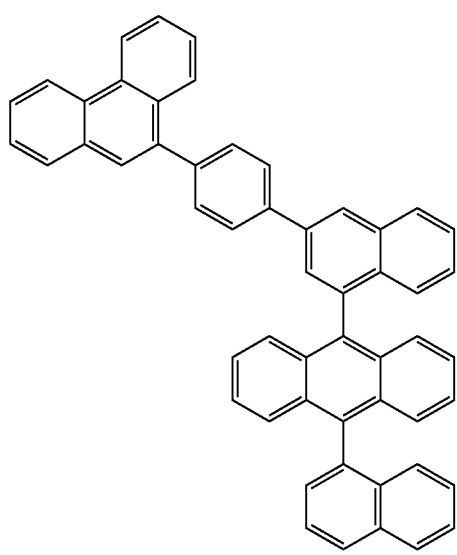
Formula 67
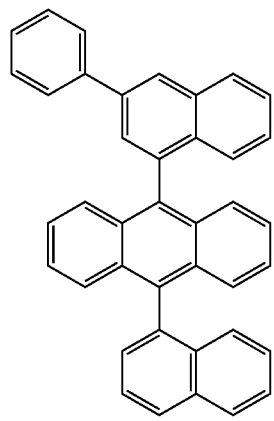
Formula 68
Formula 69
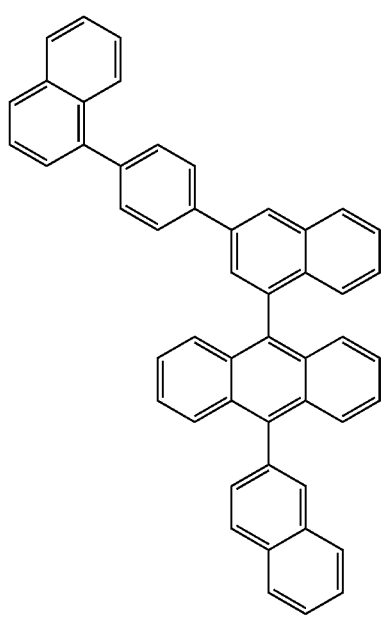

Formula 70
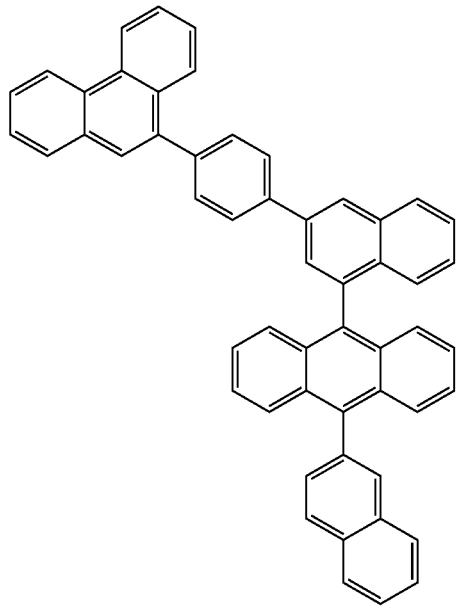
Formula 71
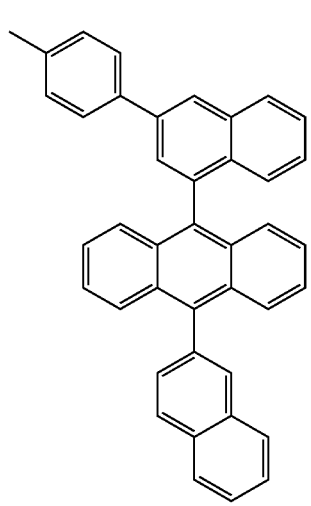
Formula 72
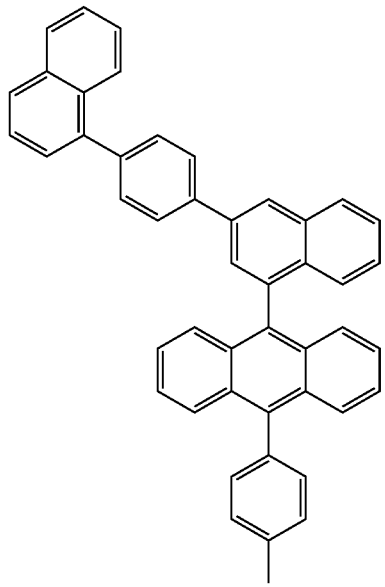
Formula 73
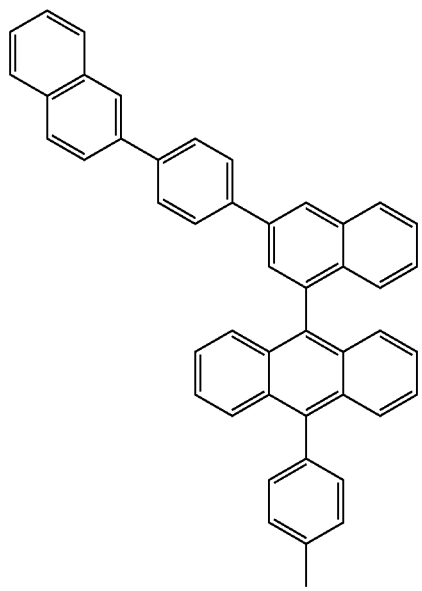

Formula 74
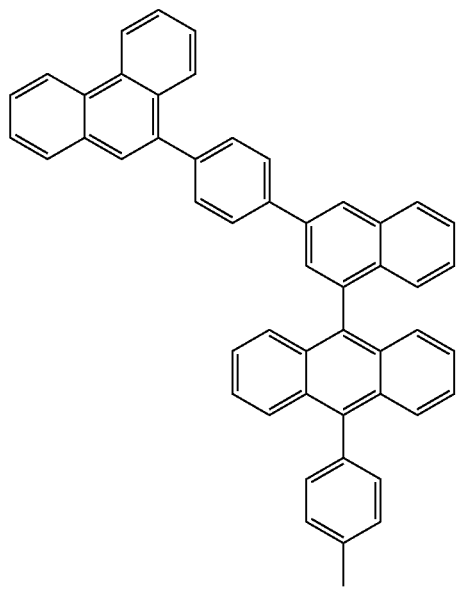
Formula 75
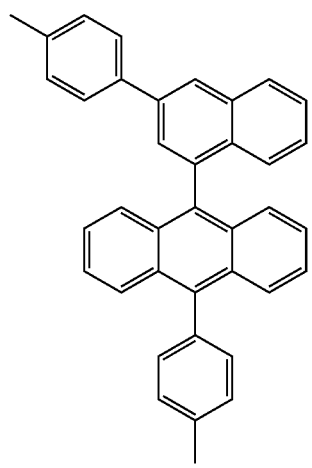
Formula 76
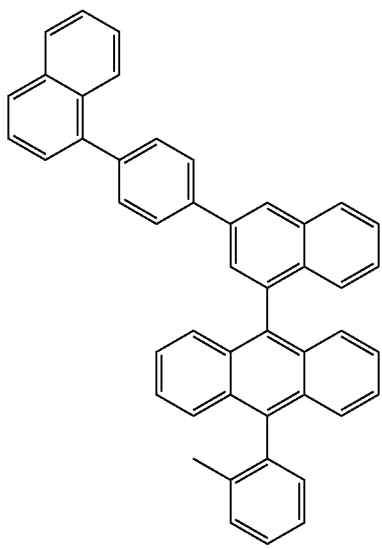
Formula 77
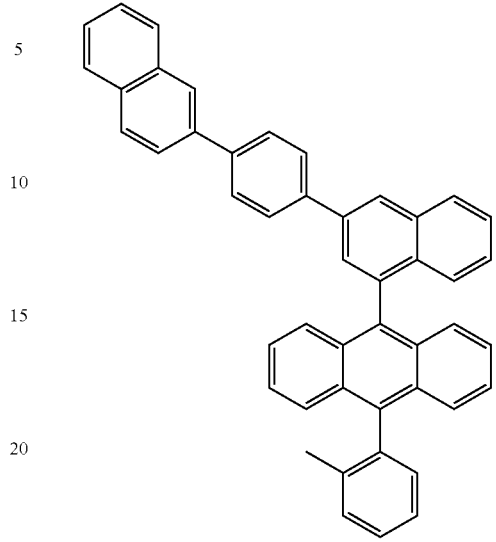
Formula 78
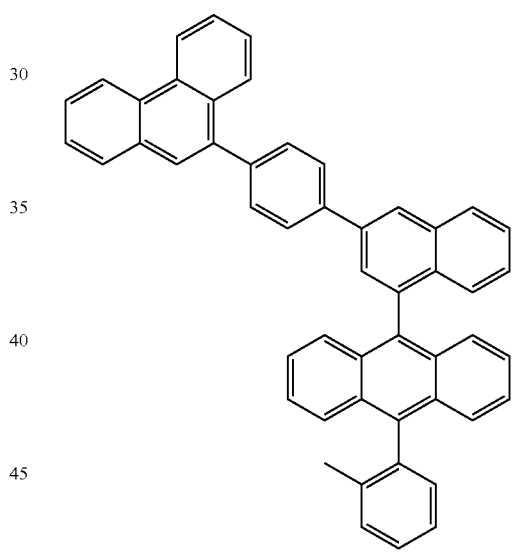
Formula 79
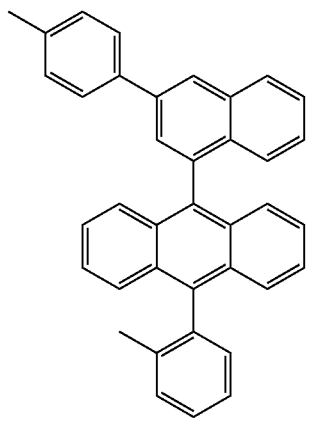

Formula 80
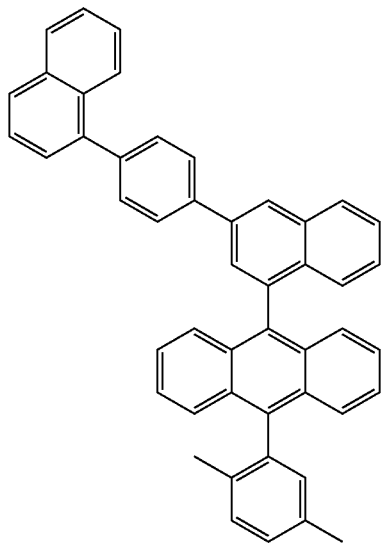
Formula 81
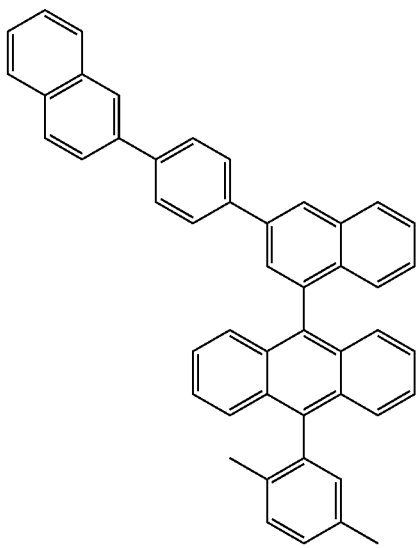
Formula 82
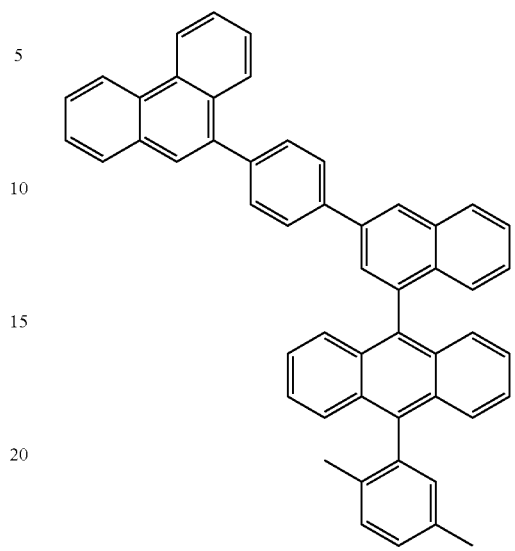
Formula 83
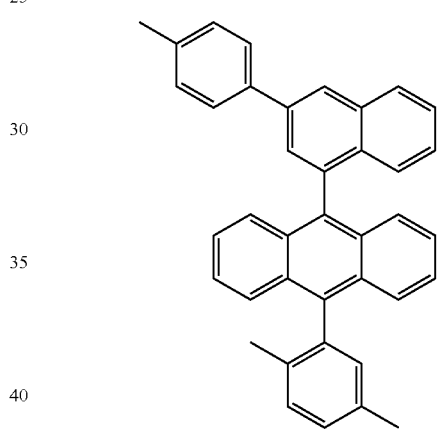
Formula 84
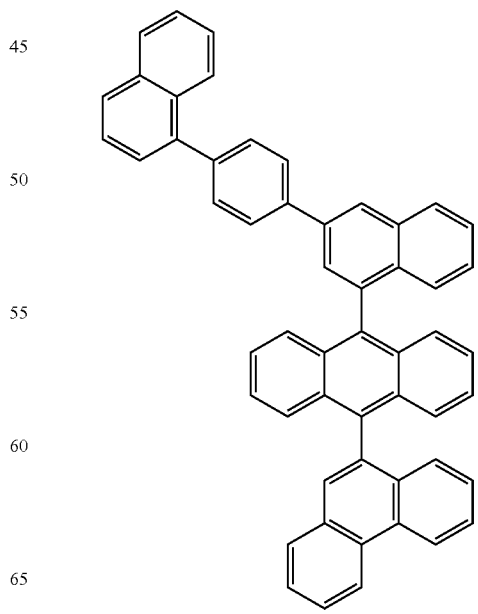

Formula 85
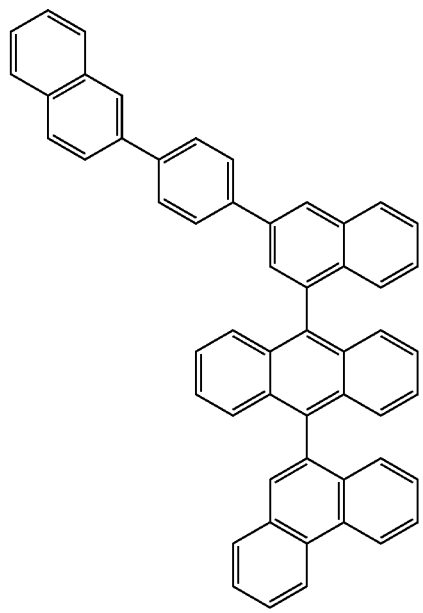
Formula 86
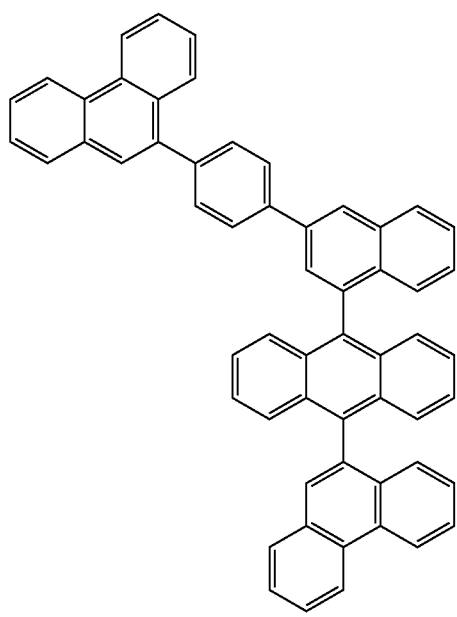
Formula 87
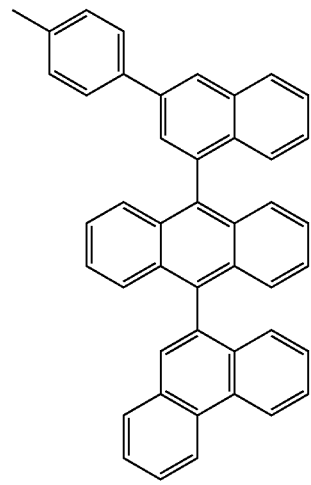
Formula 88
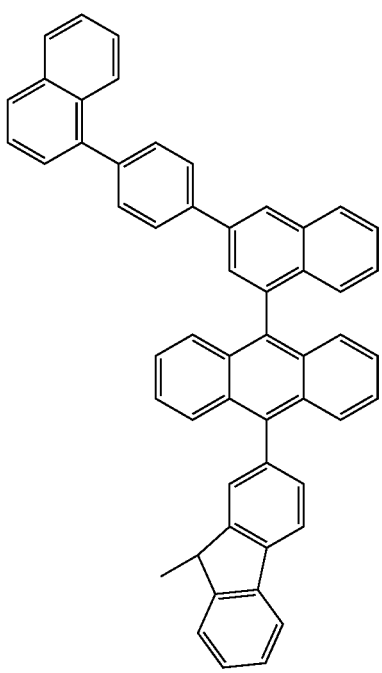

Formula 89
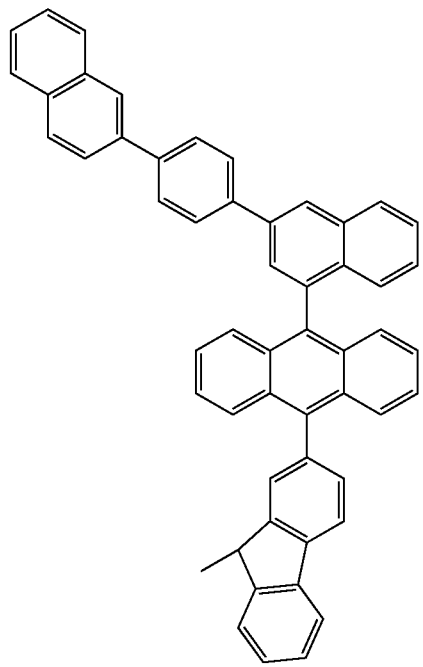
Formula 91
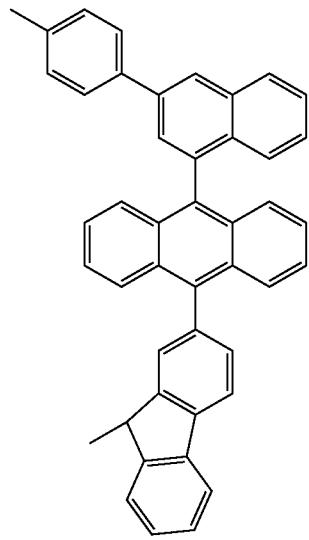
Formula 90
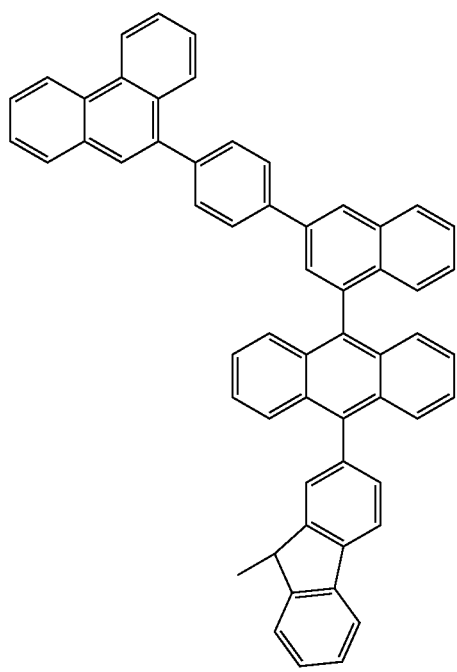
Formula 92
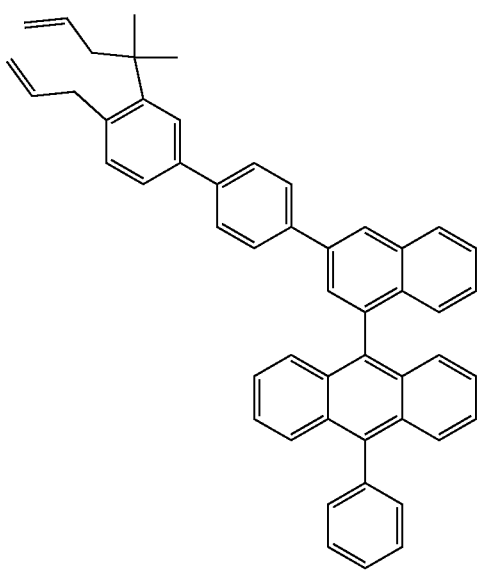

Formula 93
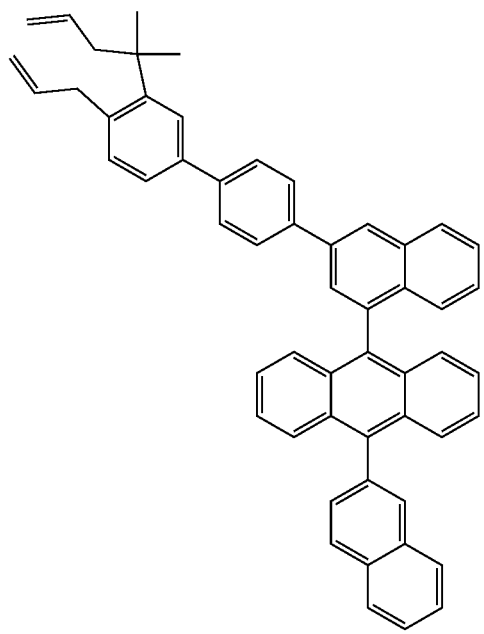
Formula 95
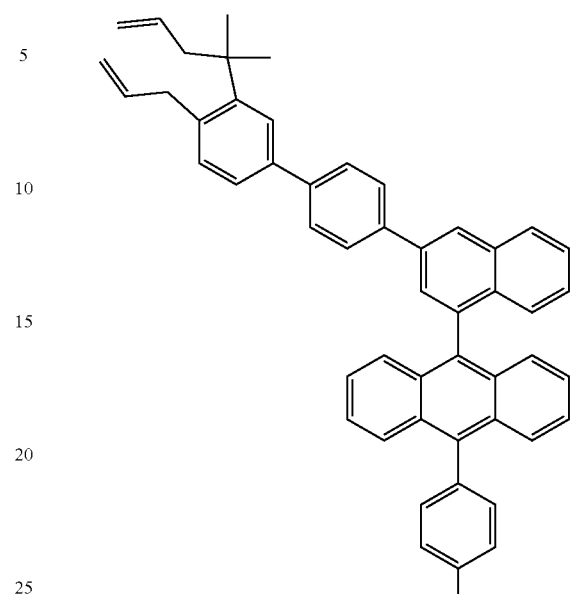
Formula 94
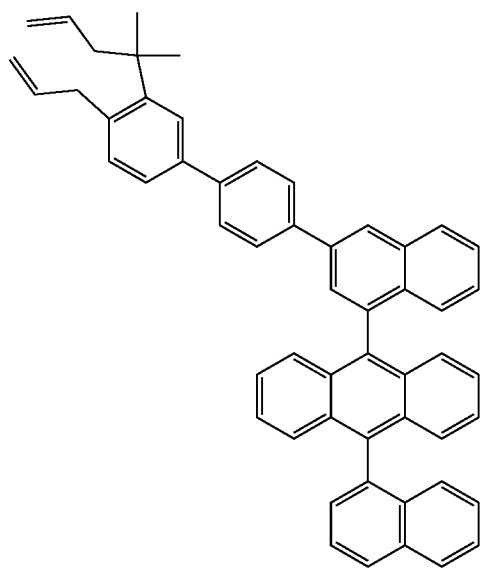
Formula 96
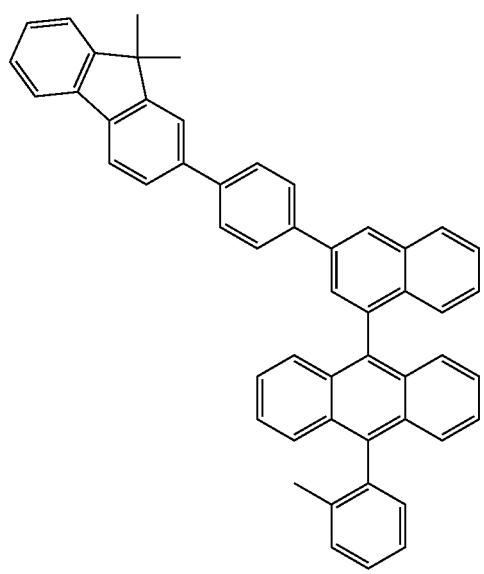

Formula 97
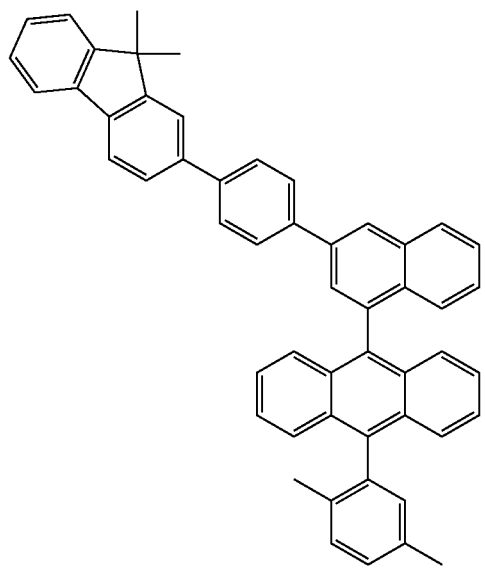
Formula 98
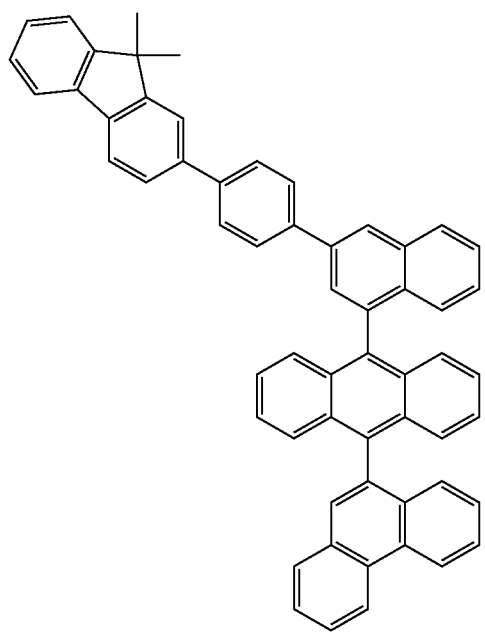
Formula 99
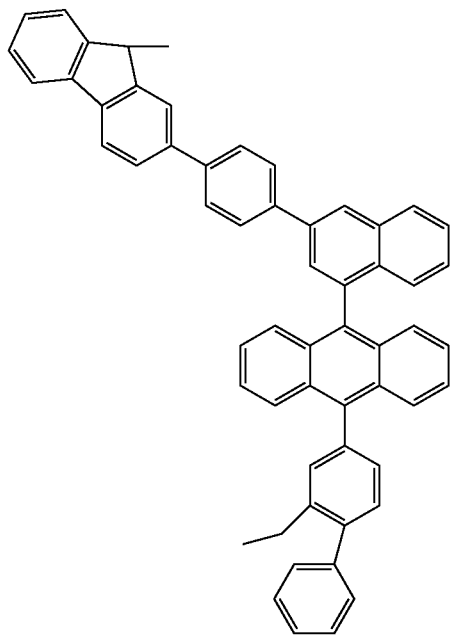
Formula 100
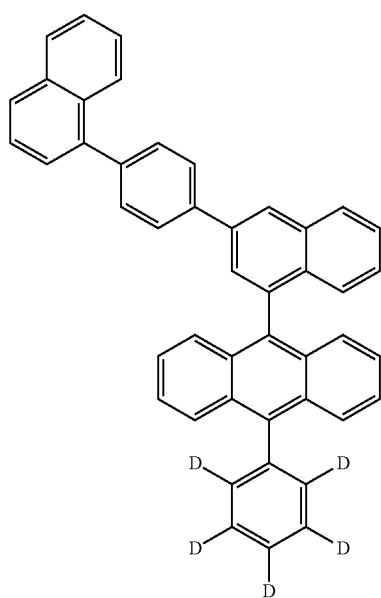

Formula 101
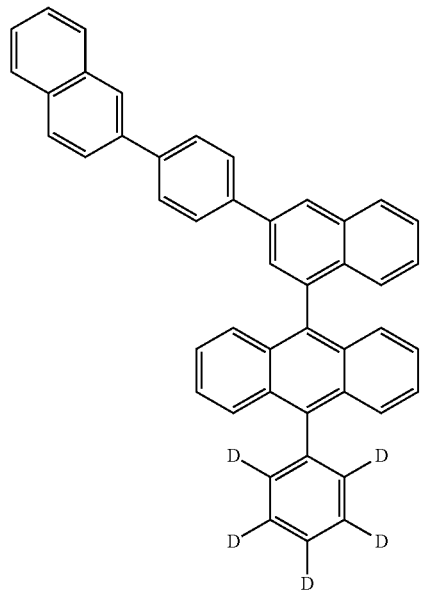
Formula 102
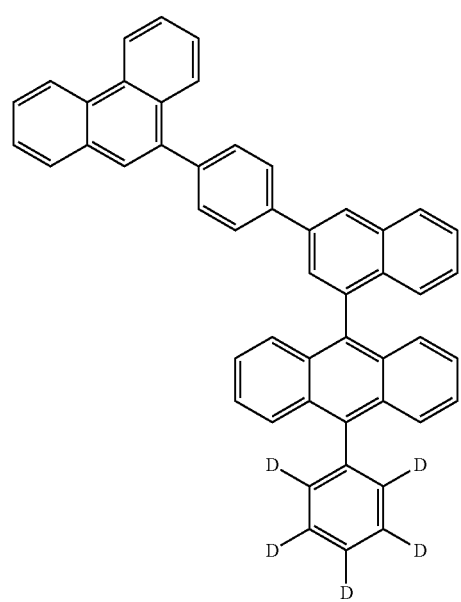
Formula 103
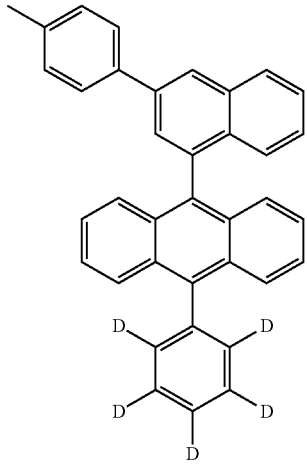
Formula 104
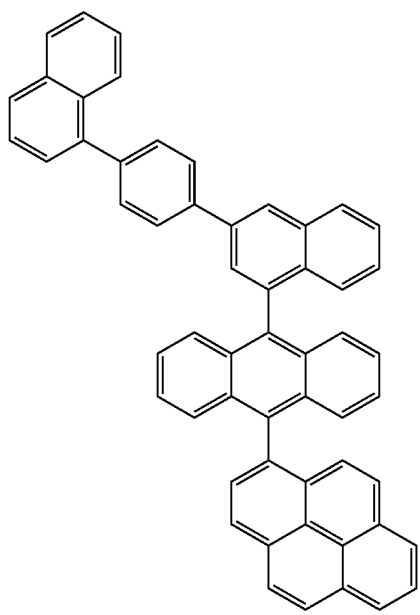
Formula 105
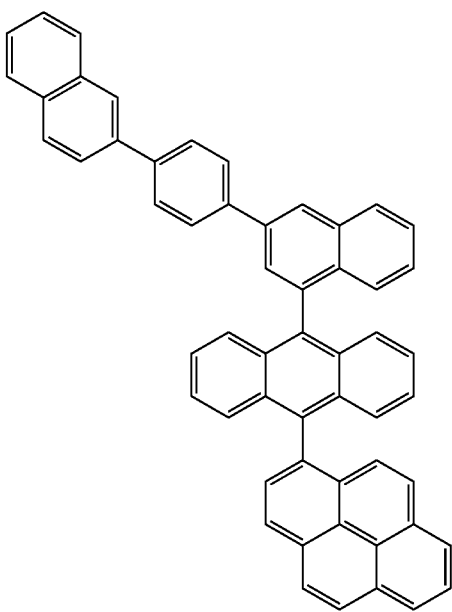

Formula 106

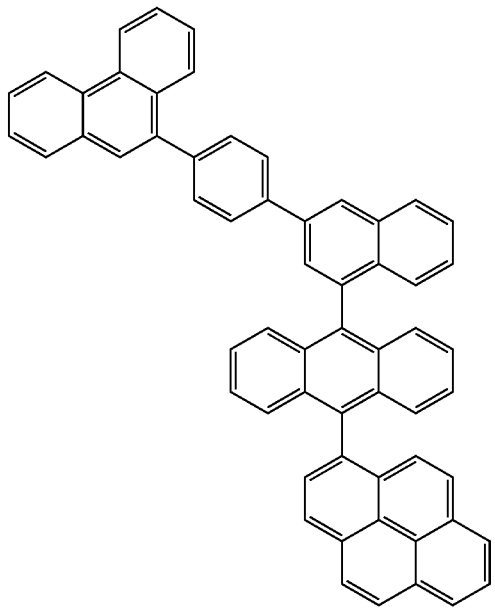

Formula 107

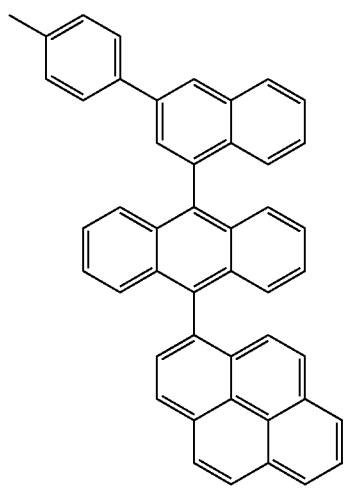

Also, an embodiment of an organic light-emitting device includes an anode, a cathode, and an anthracene derivative represented by Formula 1 between the anode and the cathode. In this regard, a layer including the anthracene derivative may be an emission layer between the anode and the cathode.

Also, an organic light-emitting device according to an embodiment of the present invention includes at least one compound represented by Formula 1 as a host compound and further includes various dopant materials therein to improve emission efficiency, color purity, and long lifespan characteristics.

An embodiment of the present invention may further include at least one dopant compound represented by Formula I or Formula II.

Formula I

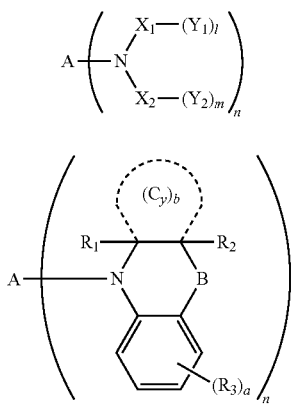

Formula II

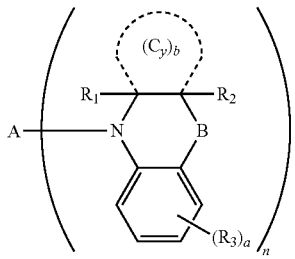

In Formula I to Formula II, A may be a substituted or unsubstituted C6-C60 arylene group, for example, anthracene, pyrene, phenanthrene, indenophenanthrene, chrysene, naphthacene, picene, triphenylene, perylene, or pentacene. In this regard, A may be a compound (or functional group) represented by Formula A1 to Formula A10.

Formula A1

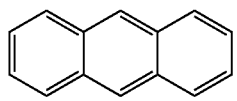

Formula A2

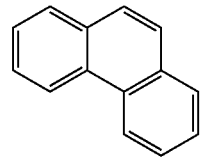

Formula A3

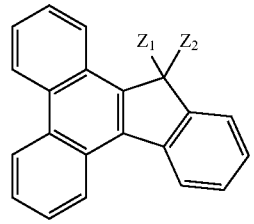

Formula A4

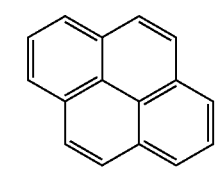

Formula A5

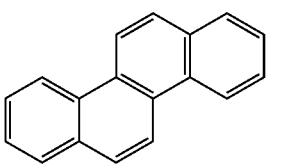

Formula A6

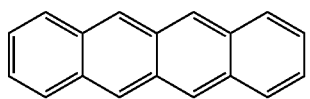

-continued

Formula A7

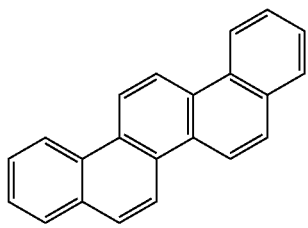

Formula A8

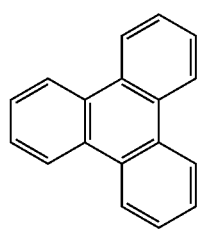

Formula A9

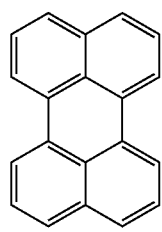

Formula A10

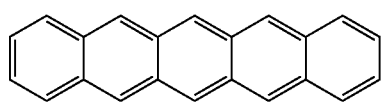

$Z_1$ to $Z_2$ of Formula A3 may be at least one of a hydrogen atom, a deuterium atom, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C1-C60 alkylthio group, a substituted or unsubstituted C3-C60 cycloalkyl group, a substituted or unsubstituted C6-C60 aryl group, a substituted or unsubstituted C5-C60 aryloxy group, a substituted or unsubstituted C5-C60 arylthio group, a substituted or unsubstituted C2-C60 heteroaryl group, a substituted or unsubstituted C1-C60 (alkyl) amino group, a di(substituted or unsubstituted C1-C60 alkyl) amino group, a (substituted or unsubstituted C6-C60 aryl)amino group, or a di(substituted or unsubstituted C6-C60 aryl)amino group, where $Z_1$ to $Z_2$ are the same or different and may, optionally, combine together with a nearby group to form a condensed ring.

In Formula I, $X_1$ to $X_2$ may be each independently a substituted or unsubstituted C6-C30 arylene group or a single bond, and $X_1$ and $X_2$ may, optionally, combine together to form a ring.

$Y_1$ to $Y_2$ may be each independently at least one of a substituted or unsubstituted C6-C24 aryl group, a substituted or unsubstituted C2-C24 heteroaryl group, a substituted or unsubstituted C1-C24 alkyl group, a substituted or unsubstituted C1-C24 heteroalkyl group, a substituted or unsubstituted C3-C24 cycloalkyl group, a substituted or unsubstituted C1-C24 alkoxy group, a cyano group, a halogen group, a substituted or unsubstituted C6-C24 aryloxy group, a substituted or unsubstituted C1-C40 alkyl silyl group, a substituted or unsubstituted C6-C30 aryl silyl group, germanium, phosphorus, boron, a deuterium atom, a hydrogen atom, where $Y_1$ to $Y_2$ may be the same or different and may, optionally, combine together with a nearby group to form an aliphatic, aromatic, heteroaliphatic, or heteroaromatic condensed ring.

For example, $X_1$ to $X_2$ of Formula I may be a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentacenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolinylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazoylene group, a substituted or unsubstituted dibenzothiophenylene group, a substituted or unsubstituted dibenzofuranylene group, a substituted or unsubstituted triazinylene group, and a substituted or unsubstituted oxadiazolylene group.

l and m may each be an integer of 1 to 20 and n may be an integer of 1 to 4.

Also, in Formula II, Cy is a substituted or unsubstituted C3-C8 cycloalkyl group, b is an integer of 1 to 4, and when b is 2 or more, the cycloalkanes may be fused. Also, each hydrogen atom may be substituted with a deuterium atom or an alkyl group, and each substituent may be the same or different.

B may be a single bond or —[C($R_5$)($R_6$)]p-, where p may be an integer of 1 to 3, and when p is 2 or more, a plurality of $R_5$ and $R_6$ may be the same or different.

$R_1$ to $R_6$ of Formula II may be each independently a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C1-C60 alkylthio group, a substituted or unsubstituted C3-C60 cycloalkyl group, a substituted or unsubstituted C6-C60 aryl group, a substituted or unsubstituted C5-C60 aryloxy group, a substituted or unsubstituted C5-C60 arylthio group, a substituted or unsubstituted C2-C60 heteroaryl group, a substituted or unsubstituted C1-C60 (alkyl)amino group, a di(substituted or unsubstituted C1-C60 alkyl)amino group, or a (substituted or unsubstituted C6-C60 aryl)amino group, a di(substituted or unsubstituted C6-C60 aryl)amino group, a substituted or unsubstituted C1-C40 alkyl silyl group, a substituted or unsubstituted C6-C30 aryl silyl group, germanium, phosphorus, or boron.

In Formula II, a may be an integer of 1 to 4 and when a is 2 or more, a plurality of $R_3$ may be the same or different, and when there are a plurality of $R_3$s, each $R_3$ (or two or more of the $R_3$s) may, optionally, combine together, and n may be an integer of 1 to 4.

For example, $R_1$, $R_2$, and $R_3$ may be each a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C1-C20 alkyl group, a substituted or unsubstituted C1-C20 alkenyl group, a substituted or unsubstituted C2-C20 alkynyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentacenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolinyl group, a substituted or unsubstituted carbazolyl group, a substituted or unsubstituted phenazinyl group, a substituted or unsubstituted phenanthridinyl group, a substituted or unsubstituted pyranyl group, substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, or a substituted or unsubstituted oxadiazolyl group. B in Formula II of the present invention may be a single bond.

Also, an amine derivative substituent bound to A or B in Formula I and Formula II may be any one of substituent 1 to substituent 52, but the amine derivative substituent is not limited thereto.

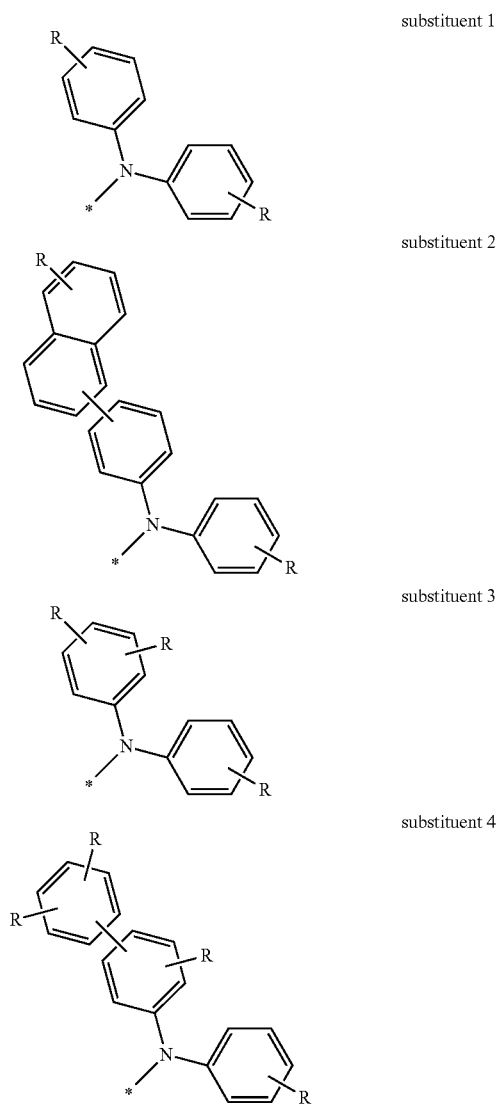

substituent 1 substituent 2 substituent 3 substituent 4 substituent 5
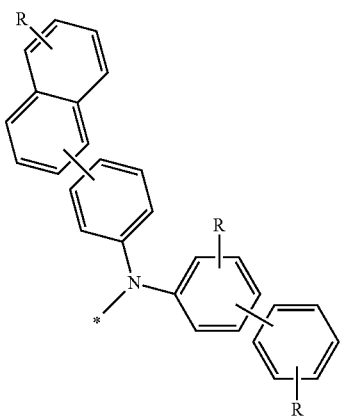
substituent 6
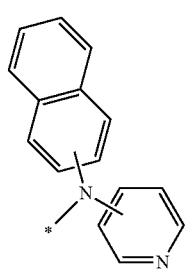
substituent 7
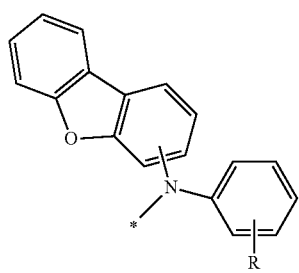
substituent 8
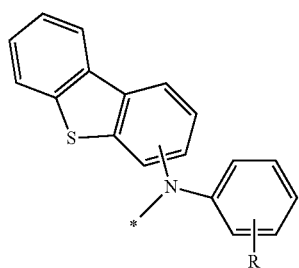
substituent 9
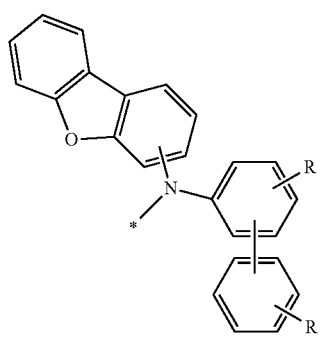
substituent 10
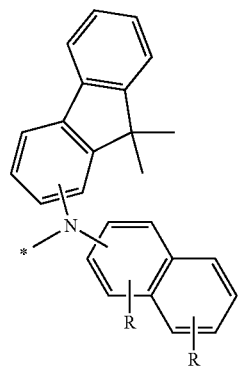
substituent 11
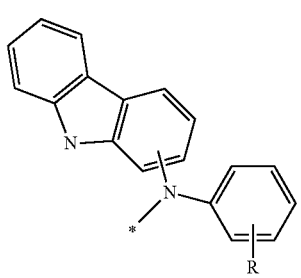
substituent 12
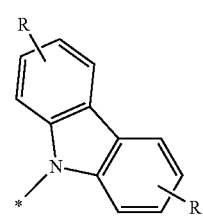
substituent 13
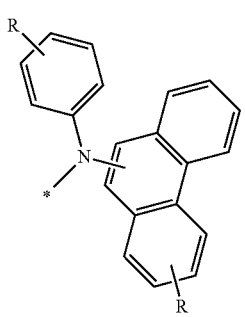
substituent 14
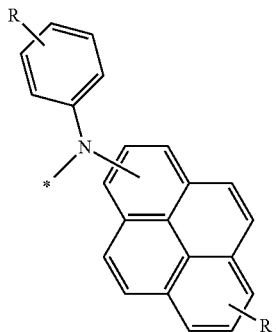

substituent 15
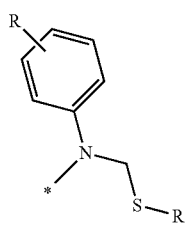
substituent 16
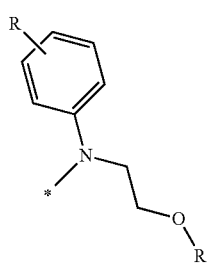
substituent 17
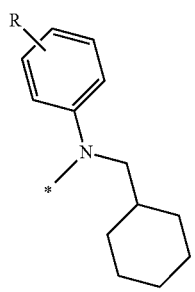
substituent 18
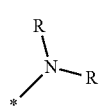
substituent 19
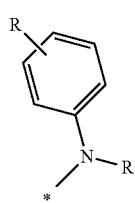
substituent 20
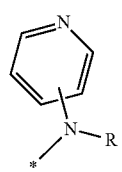
substituent 21
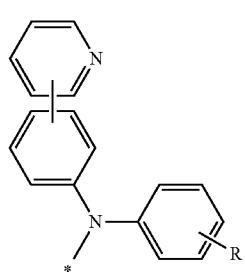
substituent 22
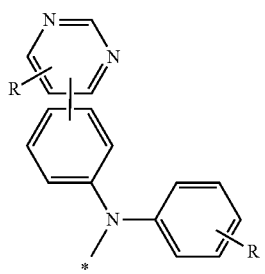
substituent 23
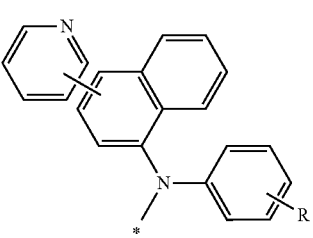
substituent 24
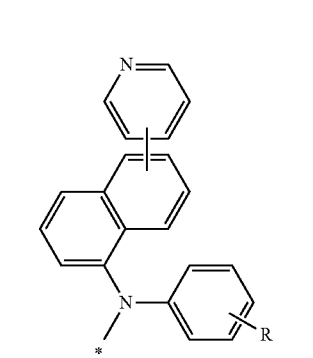
substituent 25
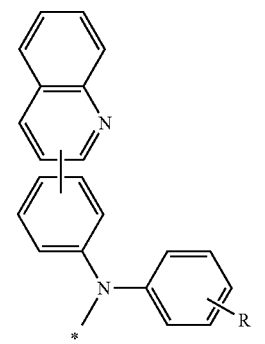
substituent 26
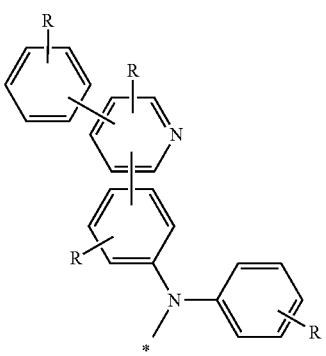

| | |
|---|---|
| sustituent 27 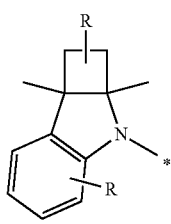 | substituent 33 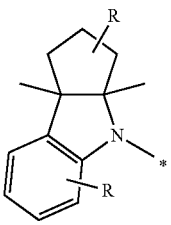 |
| substituent 28 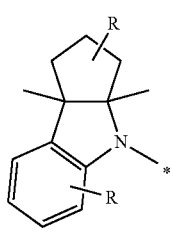 | substituent 34 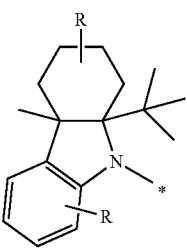 |
| substituent 29 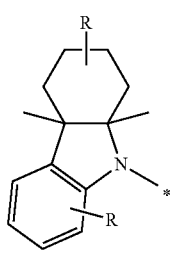 | substituent 35 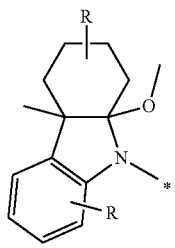 |
| sunstituent 30 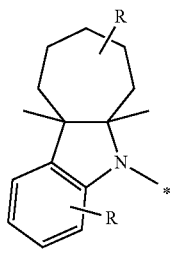 | substituent 36 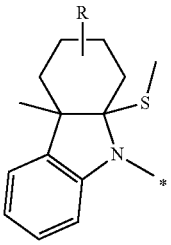 |
| substituent 31 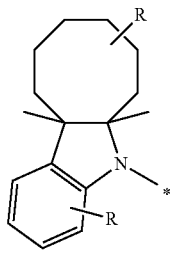 | substituent 37 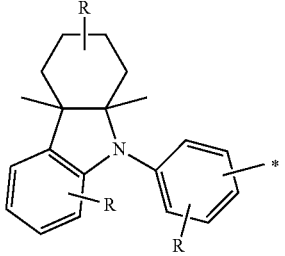 |
| substituent 32 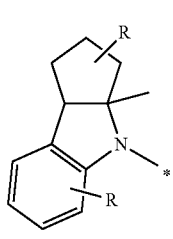 | substituent 38 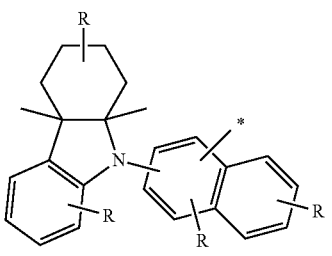 | substituent 39
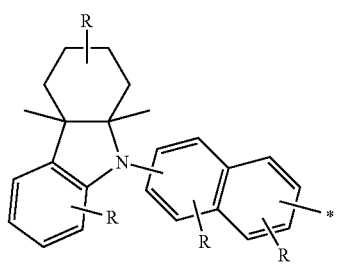
substituent 40
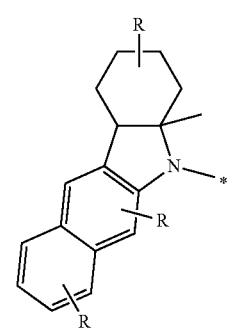
substituent 41
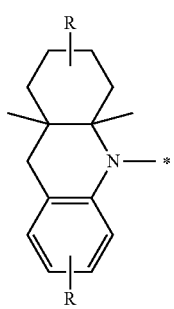
substituent 42
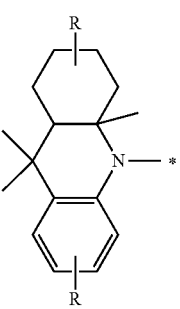
substituent 43
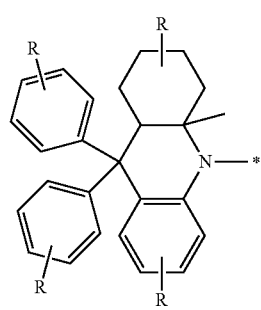
substituent 44
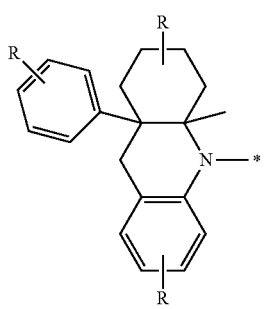
substituent 45
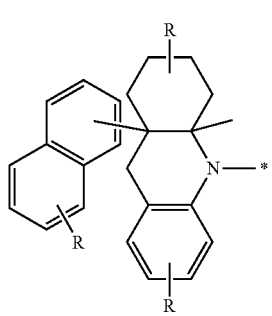
substituent 46
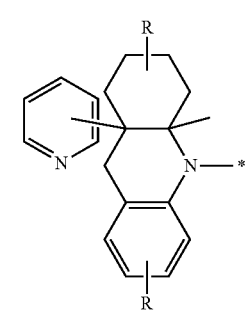
substituent 47
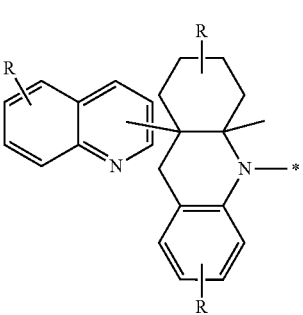
substituent 48
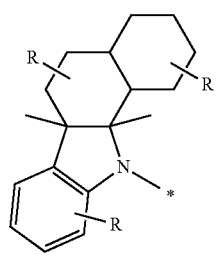

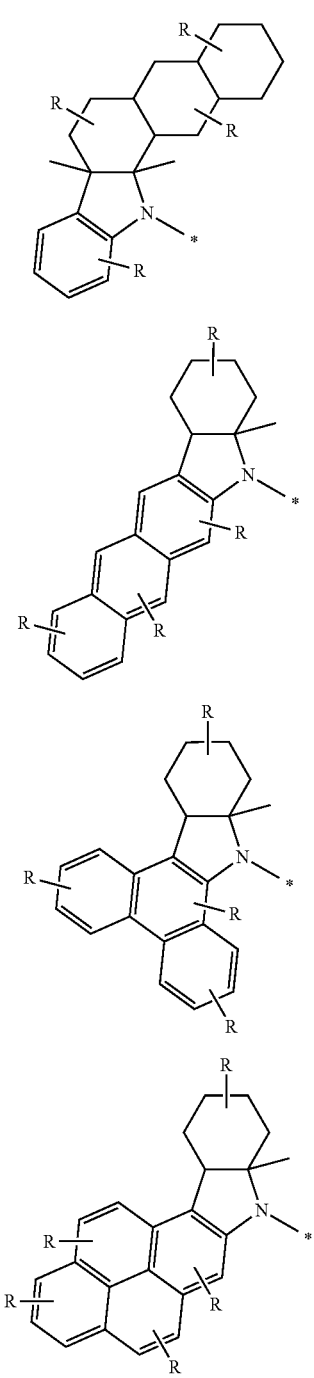

substituent 49 substituent 50 substituent 51 substituent 52

In substituent 1 to substituent 52, R may be each independently at least one of a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C1-C60 alkylthio group, a substituted or unsubstituted C3-C60 cycloalkyl group, a substituted or unsubstituted C6-C60 aryl group, a substituted or unsubstituted C5-C60 aryloxy group, a substituted or unsubstituted C5-C60 arylthio group, a substituted or unsubstituted C2-C60 heteroaryl group, a substituted or unsubstituted C1-C60 (alkyl)amino group, a di(substituted or unsubstituted C1-C60 alkyl)amino group, a (substituted or unsubstituted C6-C60 aryl)amino group, a di(substituted or unsubstituted C6-C60 aryl)amino group, a substituted or unsubstituted C1-C40 alkyl silyl group, a substituted or unsubstituted C6-C30 aryl silyl group, germanium, phosphorus, or boron, and may, optionally, combine together with a nearby substituent to form a condensed ring.

Also, at least one layer of a hole-injecting layer, a hole-transporting layer, an electron-blocking layer, a hole-blocking layer, an electron-transporting layer, or an electron-injecting layer may be between the anode and the cathode.

For example, a hole-transporting layer (HTL) may be between the anode and the organic emission layer and an electron-transporting layer (ETL) may additionally be between the cathode and the organic emission layer. In some embodiments, the HTL is layered to facilitate injection of holes from the anode, and an electron-donating molecule having a small ionization potential is used as an HTL material, and a diamine, triamine, or a tetraamine derivative having a basic structure of triphenylamine is used as the HTL material.

The HTL material may be any suitable material generally used in the art, for example, N,N'-bis(3-methyl phenyl)-N, N'-diphenyl-[1,1-biphenyl]-4,4'-diamine (TPD) or N,N'-di (naphthalene-1-yl)-N,N'-diphenyl benzidine (α-NPD) may be used.

A hole-injecting layer (HIL) may be additionally at the bottom of the HTL and an HIL material may be any suitable material generally used in the art. For example, copper-phthalocyanine (CuPc) or a starburst-type amine such as TCTA(4,4',4"-tri(N-carbazolyl)triphenyl-amine) and m-MT-DATA(4,4',4"-tris-(3-methylphenylphenyl amino)triphenylamine) may be used.

Also, the ETL used in an organic light-emitting device according to an embodiment of the present invention thoroughly transports electrons supplied from the cathode to the organic emission layer and inhibits (or reduces) the movement of holes that did not combine with an electron in the organic emission layer, to thereby increase the chance for recombination of the holes in the emission layer.

A material for the ETL may be any suitable material generally used in the art, for example, oxadiazole derivatives such as PBD, BMD, BND, or Alq$_3$.

Meanwhile, an electron-injecting layer (EIL), which facilitates thorough injection of electrons from the cathode to improve power efficiency, may be further on the ETL. An EIL material may be any suitable material generally used in the art, for example, LiF, NaCl, NaF, CsF, Li$_2$O, or BaO.

An organic light-emitting device according to an embodiment of the present invention may be used in an indicating device, a display device, or a single color or white color light emitting device.

FIG. 1 is a cross-sectional view showing a structure of an organic light-emitting device according to an embodiment of the present invention. The organic light-emitting device according to the embodiment of the present invention shown in FIG. 1 includes an anode 20, an HTL 40, an organic emission layer 50, an ETL 60, and a cathode 80, and may further include an HIL 30 and an EIL 70, one or two layers of an intermediate layer, a hole-blocking layer, or an electron-blocking layer, if needed.

Referring to FIG. 1, an embodiment of an organic light-emitting device and an embodiment of a method of manufacturing the organic light-emitting device are as follows. First, a substrate 10 is coated with an anode material to manufacture an anode 20. In this regard, the substrate 10 may be any suitable substrate generally used in an organic light-emitting device, which may include a glass substrate or a transparent plastic substrate having transparency, surface smoothness, ease of handling, and water resistance. Also, the anode material may include indium tin oxide (ITO), indium zinc oxide (IZO), tin oxide ($SnO_2$), and zinc oxide (ZnO) having good transparency and conductivity.

The anode 20 is coated with the HIL material by using vacuum thermal deposition or spin-coating to form the HIL 30. Then, the HIL 30 is coated with the HTL material by vacuum thermal evaporation or spin-coating to form the HTL 40.

Thereafter, the organic emission layer 50 is deposited on the HTL 40 and the hole-blocking layer may be selectively (or optionally) deposited on the organic emission layer 50 by using vacuum thermal evaporation or spin-coating to form a thin film. When holes pass through the organic emission layer into the cathode, lifespan and efficiency of the organic light-emitting device decrease and thus, the hole-blocking layer may include a material having a very low HOMO (Highest Occupied Molecular Orbital) level to prevent (or mitigate) such problems. In this regard, a hole-blocking material used is not particularly limited as long as the material has suitable electron-transporting capability and has an ionization potential higher than that of an emission compound of the emission layer. Representative examples of the hole-blocking material include BAlq, BCP, and TPBI.

The ETL 60 is deposited on the hole-blocking layer by using a vacuum deposition method or a spin-coating method. The ETL 60 is coated with the EIL material by using vacuum thermal deposition or spin-coating to form the EIL 70, and a metal for forming the cathode may be thermally deposited on the EIL 70 to manufacture the cathode 80, to thereby complete the organic light-emitting device. In this regard, the metal for forming the cathode may be lithium (Li), magnesium (Mg), aluminum (Al), aluminum-lithium (Al—Li), calcium (Ca), magnesium-indium (Mg—In), magnesium-silver (Mg—Ag), or the like, and a transmissive cathode using ITO and IZO may be used to obtain a top emission light-emitting device.

Also, according to another embodiment of the present invention, at least one layer of the HIL, the HTL, the electron-blocking layer, the emission layer, the hole-blocking layer, the ETL, and the EIL may be formed (e.g., deposited) by a unimolecular deposition method or a solution process. The organic light-emitting device according to an embodiment of the present invention may be used in an indicating device, a display device, or a single color light or white color light device.

EXAMPLE

Synthesis Example 1

Synthesis of a compound represented by Formula 28

Synthesis Example 1-(1)

Synthesis of Intermediate 1-a

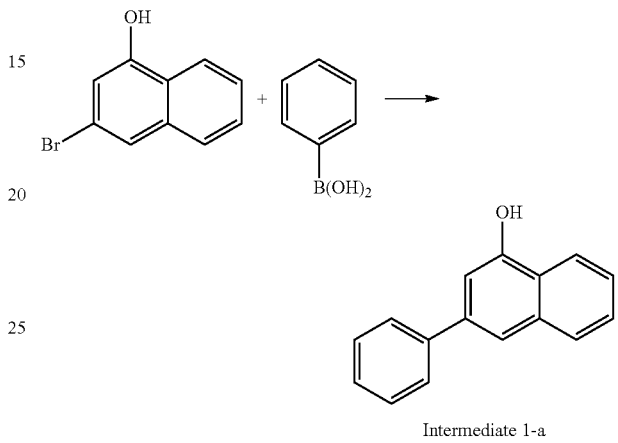

Intermediate 1-a 33.5 g (0.15 mol) of 3-bromo-1-naphthol, 3.35 g (3.1 mmol) of $Pd(PPh_3)_4$, 43 g (0.31 mol) of potassium carbonate, and 24.6 g (0.2 mol) of phenyl boronic acid were added to a 1000 mL round bottom flask, and then 200 mL of toluene, 200 mL of 1,4-dioxane, and 100 mL of water were added thereto, and the resultant was refluxed for 16 hours. After refluxing for 16 hours (or after completing the reaction), an organic layer was separated therefrom and a water layer was extracted two times with 100 mL of toluene. The collected organic layer was vacuum evaporated and then recrystallized with toluene and methanol to obtain Intermediate 1-a (33 g, 75%).

Synthesis Example 1-(2)

Synthesis of Intermediate 1-b

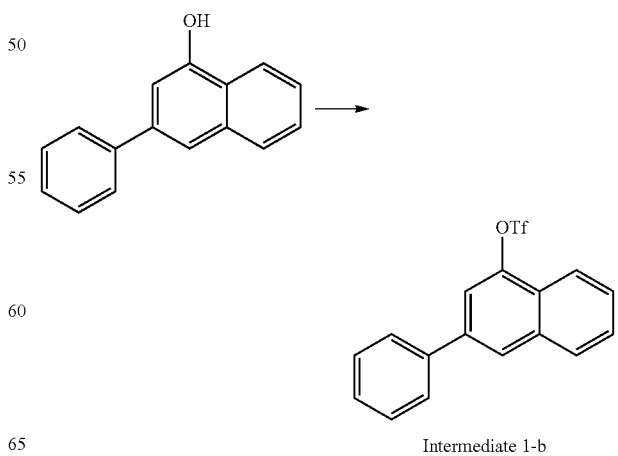

Intermediate 1-b 30 g (0.14 mol) of Intermediate 1-a was added to a 1000 mL three-neck round bottom flask and then dissolved in 300 mL of dichloromethane. After dissolution, 14 g (0.18 mol) of pyridine was added thereto and then the same was cooled to a temperature of 0° C. After slowly adding 42.3 g (0.15 mol) of (CF$_3$SO$_2$)$_2$O thereto in a drop-wise manner, the reactants were moved (i.e., increased) to room temperature, agitated for 1 hour, and then 150 mL of water was added thereto. An organic layer was separated therefrom and then vacuum evaporated. Then, column chromatography was performed to obtain Intermediate 1-b (35 g, 72.9%).

Synthesis Example 1-(3)

Synthesis of Intermediate 1-c

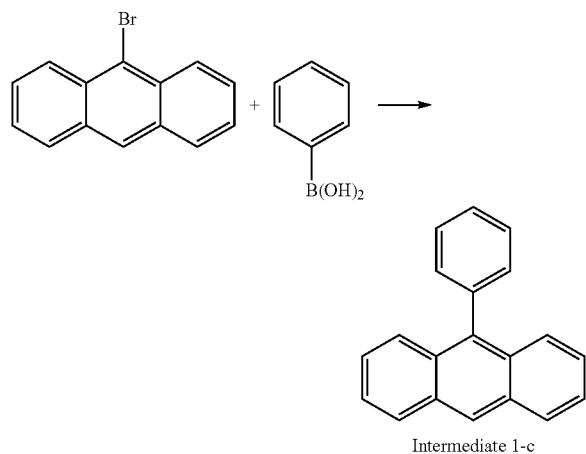

Intermediate 1-c 400 g (1.55 mol) of 9-bromoanthracene, 35.99 g (0.031 mol) of Pd(PPh$_3$)$_4$, 430.7 g (3.11 mol) of potassium carbonate, and 246.6 g (2.02 mol) of phenyl boronic acid were added to a 10 L four neck round bottom flask, and then 2000 mL of toluene, 2000 mL of 1,4-dioxane, and 1000 mL of water were added thereto and refluxed for 16 hours. After refluxing for 16 hours (or after completing the reaction), an organic layer was separated therefrom, which was vacuum evaporated and then recrystallized with toluene and methanol to obtain Intermediate 1-c (298 g, 75.3%).

Synthesis Example 1-(4)

Synthesis of Intermediate 1-d

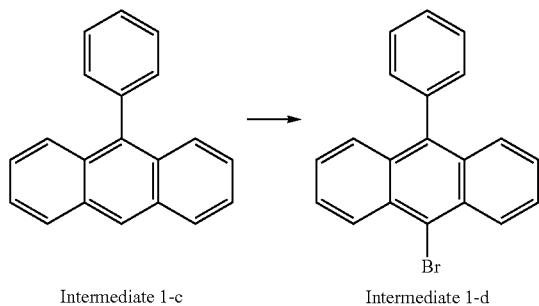

Intermediate 1-c    Intermediate 1-d 298 g (1.17 mol) of Intermediate 1-c was added to a 10 L four neck round bottom flask and then 4000 mL of dichloromethane was added thereto and Intermediate 1-c was dissolved. The reactants were cooled to a temperature of 0° C. and 206 g (1.29 mol) of bromine was slowly added thereto in a drop-wise manner. After adding bromine in a drop-wise manner, the reactants were moved (i.e., increased) to room temperature and then agitated for 2 hours. After agitating for 2 hours (or after completing the reaction), 1000 mL of sodium bicarbonate aqueous solution was added thereto, then agitated for 30 minutes, and an organic layer was separated therefrom, which was vacuum evaporated and then recrystallized with dichloromethane and methanol to obtain Intermediate 1-d (313 g, 80.3%).

Synthesis Example 1-(5)

Synthesis of Intermediate 1-e

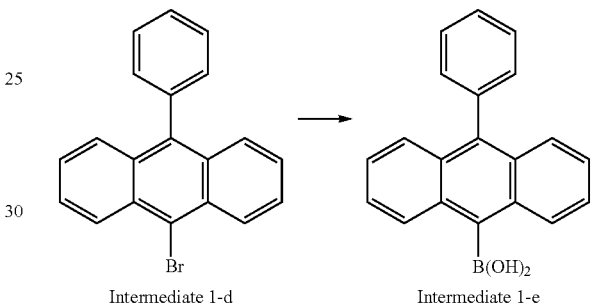

Intermediate 1-d    Intermediate 1-e 280 g (0.84 mol) of Intermediate 1-d and 3000 mL of THF were added to a 10 L four neck round bottom flask and then maintained at a temperature of −78° C. 630 mL of 1.6 M n-butyllithium (n-BuLi) was slowly added thereto in a dropwise-manner, agitated for 2 hours, and then B(OMe)$_3$ was added thereto in a drop-wise manner at the same (substantially the same) temperature. The temperature thereof was increased to room temperature and then agitated for 12 hours. After agitating for 12 hours (or after completing the reaction), 2 N HCl was added thereto. An organic layer was separated therefrom, neutralized, and then recrystallized with toluene to obtain Intermediate 1-e (228 g, 91%).

Synthesis Example 1-(6)

Synthesis of a Compound Represented by Formula 28

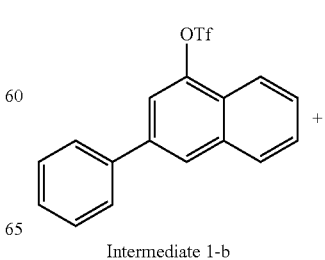

Intermediate 1-b

+

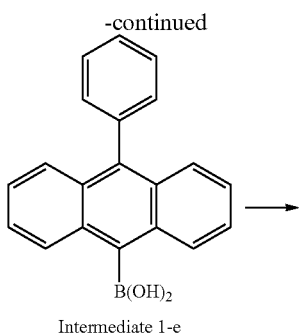

Intermediate 1-e

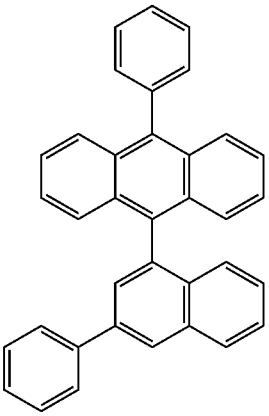

Formula 28

30 g (0.085 mol) of Intermediate 1-b, 2.5 g (0.002 mol) of Pd(PPh$_3$)$_4$, 29.4 g (0.21 mol) of potassium carbonate, and 33 g (0.11 mol) of Intermediate 1-e were added to a 1000 mL four neck round bottom flask and then 300 mL of toluene, 150 mL of ethanol, and 150 mL of water were added thereto and then refluxed for 12 hours. After refluxing for 12 hours (or after completing the reaction), an organic layer was separated therefrom, which was vacuum evaporated and then recrystallized with toluene and methanol to obtain a compound represented by (Formula 28 (22 g, 56.7%), and NMR spectroscopy was performed to identify the same.

δ 8.32 (1H), 8.12 (1H), 7.94-7.93 (1H), 7.86-7.83 (2H), 7.80 (1H), 7.77 (1H), 7.69-7.48 (11H), 7.42-7.33 (3H), 7.30-7.26 (3H)

Synthesis Example 2

Synthesis of a Compound Represented by Formula 59

Synthesis Example 2-(1)

Synthesis of Intermediate 2-a

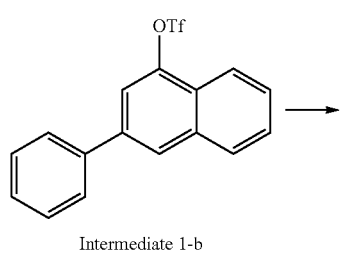

Intermediate 1-b

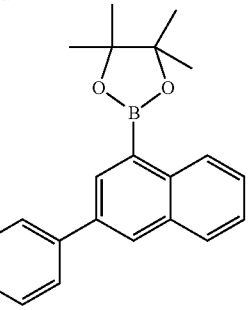

Intermediate 2-a 32 g (0.062 mol) of Intermediate 1-b, 23.8 g (0.094 mol) of bis(pinacolato)diborone, 2.5 g (0.003 mol) of PdCl$_2$(dppf), 21.3 g (0.28 mol) of potassium acetate, and 350 mL of toluene were added to a 1000 mL four neck round bottom flask and then refluxed for 12 hours. After refluxing for 12 hours (or after completing the reaction), an organic layer was separated therefrom and then vacuum evaporated. Column chromatography was performed to obtain Intermediate 2-a (16.8 g, 81.5%).

Synthesis Example 2-(2)

Synthesis of Intermediate 2-b

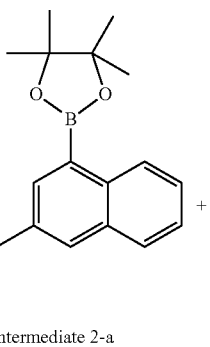

Intermediate 2-a

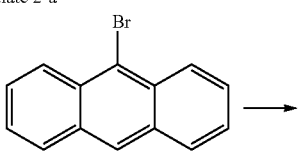

Intermediate 2-b 11.5 g (0.045 mol) of 9-bromoanthracene, 17 g (0.051 mol) of Intermediate 2-a, 1.8 g (0.002 mol) of PdCl$_2$(dppf), and 9.4 g (0.11 mol) of sodium bicarbonate were added to a 500 mL three neck round bottom flask, and then 110 mL of tetrahydrofuran and 30 mL of water were added thereto and then refluxed for 12 hours. After refluxing for 12 hours (or after completing the reaction), an organic layer was separated therefrom and a water layer was extracted once with 150 mL of dichloromethane. The collected organic layer was vacuum evaporated. Column chromatography was performed to obtain Intermediate 2-b (14.5 g, 85.3%).

Synthesis Example 2-(3)

Synthesis of Intermediate 2-c

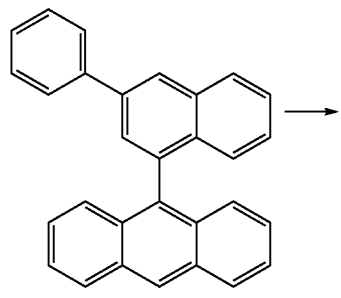

Intermediate 2-b

↓

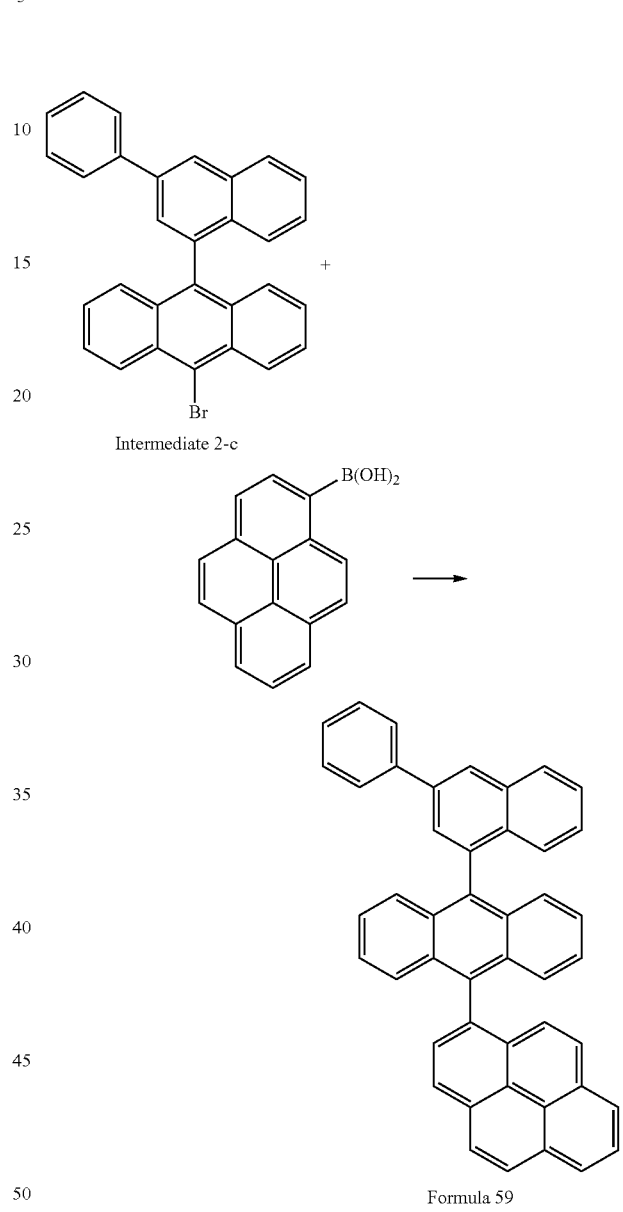

Synthesis Example 2-(3)

Synthesis of a Compound Represented by Formula 59

14.5 g (0.038 mol) of Intermediate 2-b was added to a 500 mL three neck round bottom flask, 95 mL of N,N-dimethyl formaldehyde was added thereto to dissolve Intermediate 2-b. After cooling the reactants to a temperature of 0° C., 8.1 g (0.146 mol) of N-bromosuccinimide (NBS) was dissolved in 20 mL of N,N-dimethyl formaldehyde and then slowly added to the three neck round bottom flask in a drop-wise manner. After adding the NBS solution in a drop-wise manner, the reactants were moved to room temperature and then agitated for 4 hours. After agitating for 4 hours (or after completing the reaction), 100 mL of methanol was added thereto and then filtered. A filtered crystal was recrystallized with toluene and methanol to obtain Intermediate 2-c (12 g, 68.6%).

3.9 g (0.016 mol) of 1-pyrene boronic acid, 6 g (0.013 mol) of Intermediate 2-c, 0.4 g (0.001 mol) of Pd(PPh$_3$)$_4$, and 4.5 g (0.033 mol) of sodium bicarbonate were added to a 250 mL of three neck round bottom flask, and then 30 mL of toluene, 30 mL of tetrahydrofuran, and 18 mL of water were added thereto and then refluxed for 12 hours. After refluxing for 12 hours (or after completing the reaction), the reactants were cooled, 50 mL of methanol was added thereto and then filtered. A crystal obtained therefrom was recrystallized by using dichlorobenzene to obtain a compound represented by Formula 59 (3.5 g, 46%), and NMR spectroscopy was performed to identify the same.

δ 8.55 (1H), 8.18-8.04 (4H), 7.91-7.85 (6H), 7.82 (1H), 7.76 (1H), 7.71 (4H), 7.55-7.41 (7H), 7.39 (4H)

Synthesis Example 3

Synthesis of a Compound Represented by Formula 60

Synthesis Example 3-(1)

Synthesis of Intermediate 3-a

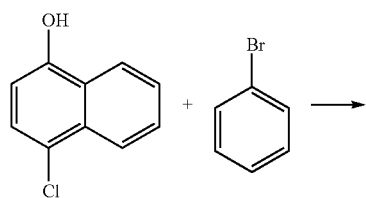

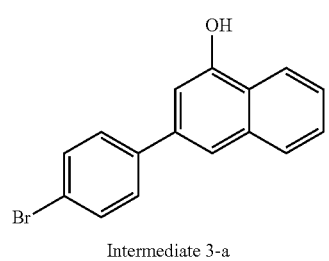

Intermediate 3-a

Intermediate 3-a was synthesized as in the method disclosed in Chemistry—An Asian Journal, 2011, vol. 6(8), 2130-2146, the entire contents of which is incorporated herein by reference.

Synthesis Example 3-(2)

Synthesis of Intermediate 3-b

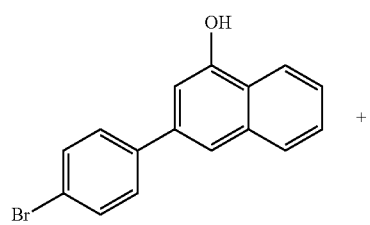

Intermediate 3-a

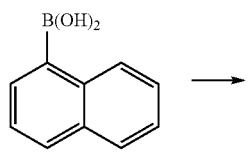

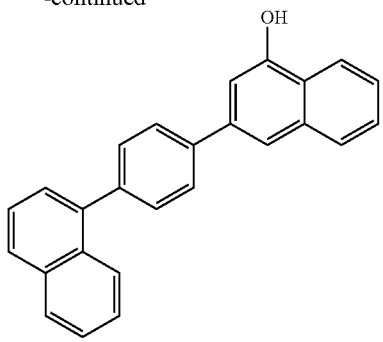

Intermediate 3-b 25 g (0.08 mol) of Intermediate 3-a, 2.4 g (0.002 mol) of Pd(PPh$_3$)$_4$, 28.9 g (0.21 mol) of potassium carbonate, and 18.7 g (0.11 mol) of 2-naphthalene boronic acid were added to a 1000 mL four neck round bottom flask, and then 150 mL of toluene, 150 mL of 1,4-dioxane, and 125 mL of water were added thereto and then refluxed for 12 hours. After refluxing for 12 hours (or after completing the reaction), an organic layer was separated therefrom, which was vacuum evaporated and recrystallized with toluene and methanol to obtain Intermediate 3-b (18 g, 62.2%).

Synthesis Example 3-(2)

Synthesis of Intermediate 3-c

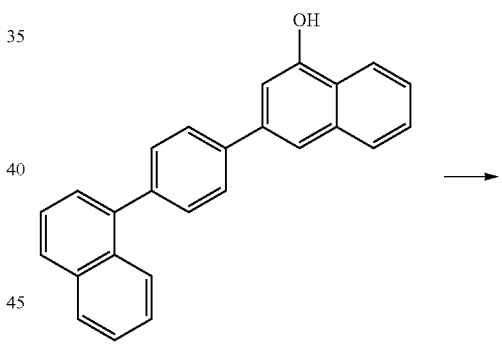

Intermediate 3-b

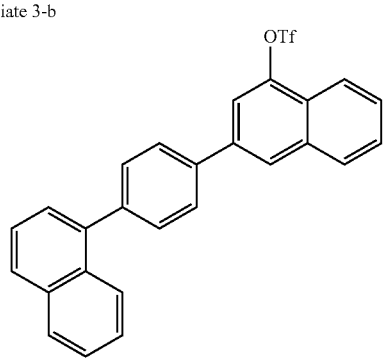

Intermediate 3-c 18 g (0.05 mol) of Intermediate 3-b was added to a 1000 mL three neck round bottom flask and then dissolved in 200 mL of dichloromethane. After dissolving the reactants, 5.3 g (0.07 mol) of pyridine was added thereto and then cooled to a temperature of 0° C. Then, 16.1 g (0.6 mol) of (CF₃SO₂)₂O was slowly added in a drop-wise manner. After slowly adding the same in a drop-wise manner, the reactants were maintained at room temperature for 1 hour and 150 mL of water was added thereto. An organic layer was separated therefrom and then vacuum evaporated. Column chromatography was performed to obtain Intermediate 3-c (19 g, 76.4%).

Synthesis Example 3-(3)

Synthesis of a Compound Represented by Formula 60

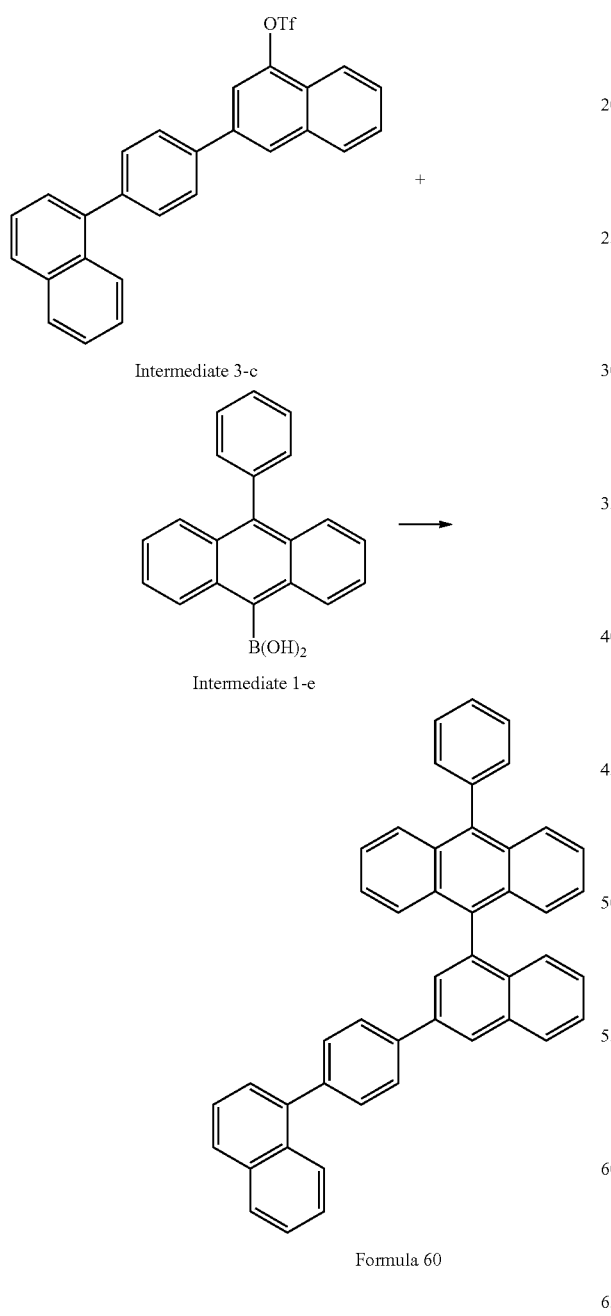

19 g (0.04 mol) of Intermediate 3-c, 1.1 g (0.001 mol) of Pd(PPh₃)₄, 13.7 g (0.1 mol) of potassium carbonate, and 15.4 g (0.05 mol) of Intermediate 1-e were added to a 1000 mL four neck round bottom flask, and then 200 mL of toluene, 100 mL of ethanol, and 100 mL of water were added thereto and then refluxed for 12 hours. After refluxing for 12 hours (or after completing the reaction), an organic layer was separated therefrom, which was vacuum evaporated and recrystallized with toluene and methanol to obtain a compound represented by Formula 60 (12 g, 51.9%), and then NMR spectroscopy was performed to identify the same.

δ 8.55 (2H), 8.42 (1H), 8.08-8.04 (3H), 7.91-7.76 (6H), 7.61-7.51 (9H), 7.41-7.39 (5H), 7.25 (4H)

Synthesis Example 4

Synthesis of a Compound Represented by Formula 63

Synthesis Example 4-(1)

Synthesis of Intermediate 4-a

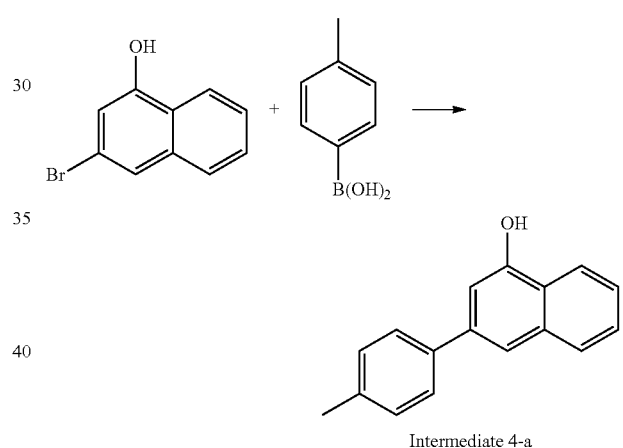

Intermediate 4-a was synthesized using the method described in Synthesis Example 1-(1), except that toluene-4-boronic acid was used instead of phenyl boronic acid.

Synthesis Example 4-(2)

Synthesis of Intermediate 4-b

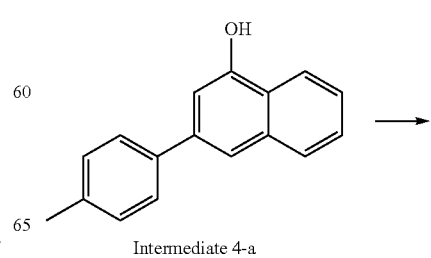

-continued

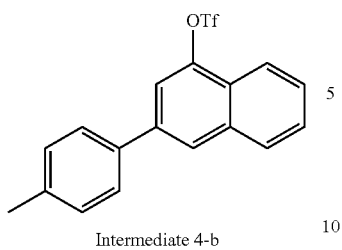

Intermediate 4-b 20 g (0.09 mol) of Intermediate 4-a was added to a 1000 mL three neck round bottom flask and then dissolved in 200 mL of dichloromethane. After dissolving the reactants, 8.8 g (0.11 mol) of pyridine was added thereto and then the reactants were cooled to a temperature of 0° C. 26.5 g (0.09 mol) of (CF$_3$SO$_2$)$_2$O was slowly added in a drop-wise manner. After slowly adding the same in a drop-wise manner, the reactants were maintained at room temperature for 1 hour and 150 mL of water was added thereto. An organic layer was separated therefrom and then vacuum evaporated. Column chromatography was performed to obtain Intermediate 4-b (25 g, 79.9%).

Synthesis Example 4-(3)

Synthesis of a Compound Represented by Formula 63

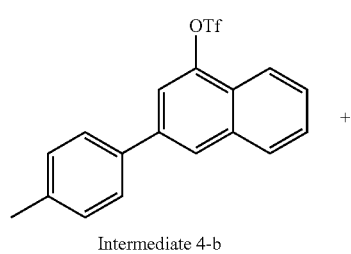

Intermediate 4-b

+

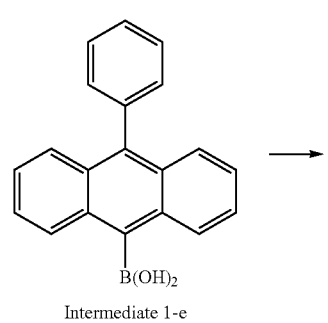

Intermediate 1-e

-continued

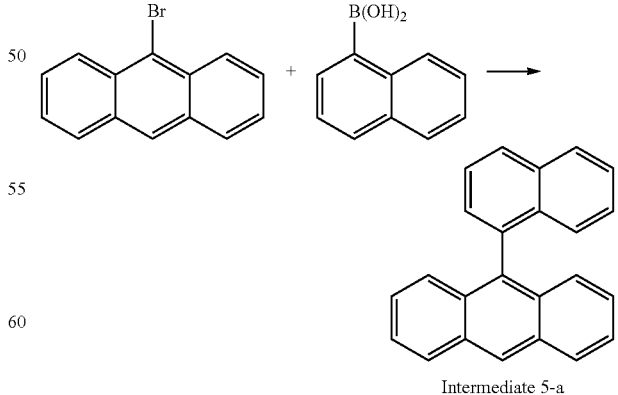

Formula 63

25 g (0.082 mol) of Intermediate 4-b, 1.5 g (0.001 mol) of Pd(PPh$_3$)$_4$, 18.1 g (0.13 mol) of potassium carbonate, and 20.3 g (0.07 mol) of Intermediate 1-e were added to a 1000 mL four neck round bottom flask, and then 250 mL of toluene, 125 mL of ethanol, and 125 mL of water were added thereto, and then refluxed for 12 hours. After refluxing for 12 hours (or after completing the reaction), an organic layer was separated therefrom and a water layer was extracted once with 200 mL of toluene. The organic layer was vacuum evaporated and then recrystallized with toluene and methanol to obtain a compound represented by Formula 63 (13 g, 52.9%), and then NMR spectroscopy was used to identify the same.

δ 8.32 (1H), 8.12 (1H), 7.94-7.93 (1H), 7.86-7.83 (2H), 7.80 (1H), 7.77 (1H), 7.55-7.51 (6H), 7.41-7.33 (10H), 2.34 (3H)

Synthesis Example 5

Synthesis of a Compound Represented by Formula 67

Synthesis Example 5-(1)

Synthesis of Intermediate 5-a

Intermediate 5-a 93.1 g (0.36 mol) of 9-bromoanthracene and 12.7 g (0.011 mol) of Pd(PPh$_3$)$_4$, 132 g (0.91 mol) potassium carbonate, and 87.2 g (0.51 mol) of 1-naphthalene boronic acid, and then 500 mL of toluene, 500 mL of tetrahydrofuran, and 200 mL of water were added thereto and then refluxed for 16 hours. After refluxing for 16 hours (or after completing the reaction), an organic layer was separated therefrom, and a water layer was extracted two times with 1000 mL of toluene. The organic layer was vacuum evaporated and then recrystallized with toluene and methanol to obtain Intermediate 5-a (88 g, 79.4%).

Synthesis Example 5-(2)

Synthesis of Intermediate 5-b

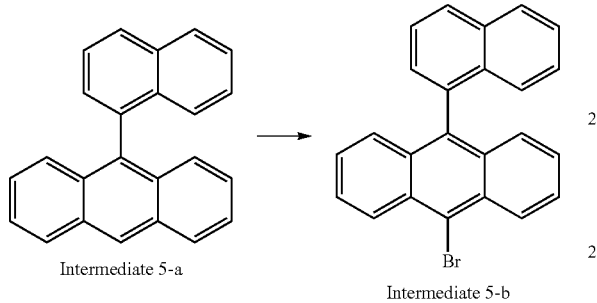

Intermediate 5-a

Intermediate 5-b 88 g (0.29 mol) of Intermediate 5-a was added to a 2 L four neck round bottom flask and 700 mL of dimethyl formamide was added thereto to dissolve Intermediate 5-a. Thereafter, NBS (70.7 g, 0.4 mol) was dissolved in 200 mL of dimethyl formamide. The NBS solution obtained therefrom was slowly added in a drop-wise manner to the flask in which the Intermediate 5-a was dissolved. After adding the NBS solution in a drop-wise manner, the reactants were agitated for 2 hours. After agitating for 2 hours (or after completing the reaction), the reactants were immersed in water to obtain Intermediate 5-b (108 g, 97.5%).

Synthesis Example 5-(3)

Synthesis of Intermediate 5-c

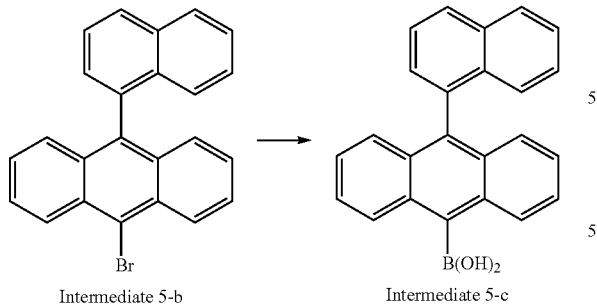

Intermediate 5-b

Intermediate 5-c 5 g (0.2 mol) of Intermediate 5-b and 750 mL of tetrahydrofuran were added to a four neck round bottom flask and then maintained at a temperature of −78° C. 150 mL of 1.6 M n-BuLi was slowly added in a drop-wise manner to the flask, agitated for 2 hours, and then B(OMe)₃ was added thereto in a drop-wise manner at the same temperature. The temperature was increased to room temperature and then the resultant was agitated for 12 hours. After agitating for 12 hours (or after completing the reaction), 2 N HCl was added thereto. An organic layer was separated therefrom, neutralized, and then recrystallized with toluene to obtain Intermediate 5-c (30 g, 45%).

Synthesis Example 5-(4)

Synthesis of a Compound Represented by Formula 67

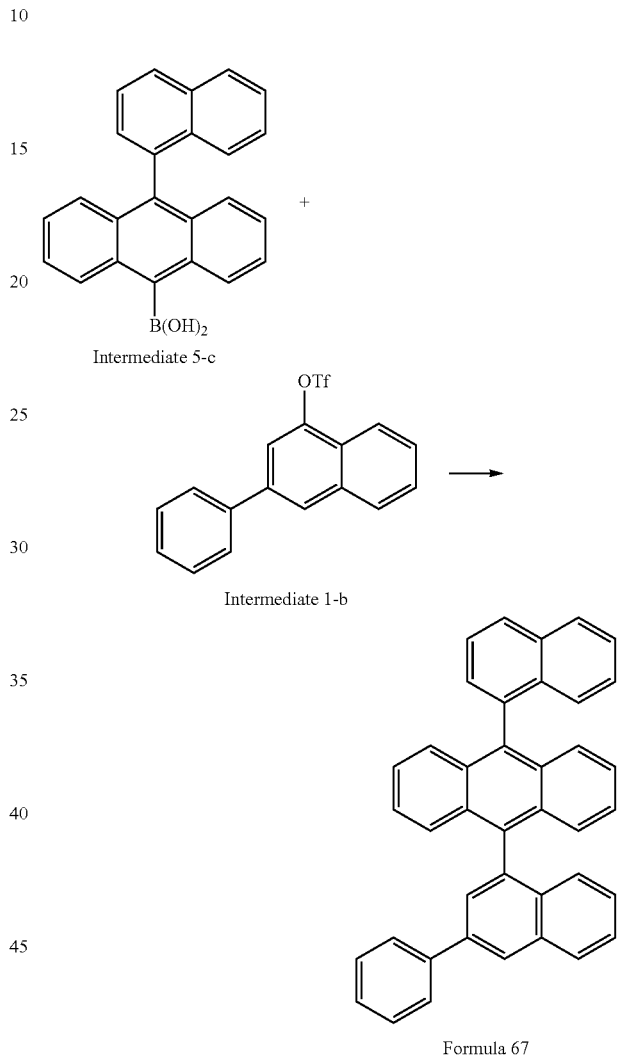

28.5 g (0.082 mol) of Intermediate 5-c, 1.5 g (0.001 mol) of Pd(PPh₃)₄, 18.1 g (0.13 mol) of potassium carbonate, and 20.3 g (0.07 mol) of Intermediate 1-e were added to a 1000 mL four neck round bottom flask, and then 250 mL of toluene, 125 mL of ethanol, and 125 mL of water were added thereto and refluxed for 12 hours. After refluxing for 12 hours (or after completing the reaction), an organic layer was separated therefrom and a water layer was extracted once with 200 mL of toluene. The organic layer was vacuum evaporated and then recrystallized with toluene and methanol to obtain a compound represented by Formula 67 (21.1 g, 50.9%) and NMR spectroscopy was performed to identify the same.

δ 8.34 (1H), 8.13-7.97 (5H), 7.80 (1H), 7.77 (1H), 7.76-7.49 (11H), 7.48-7.23 (7H)

Figure 2:
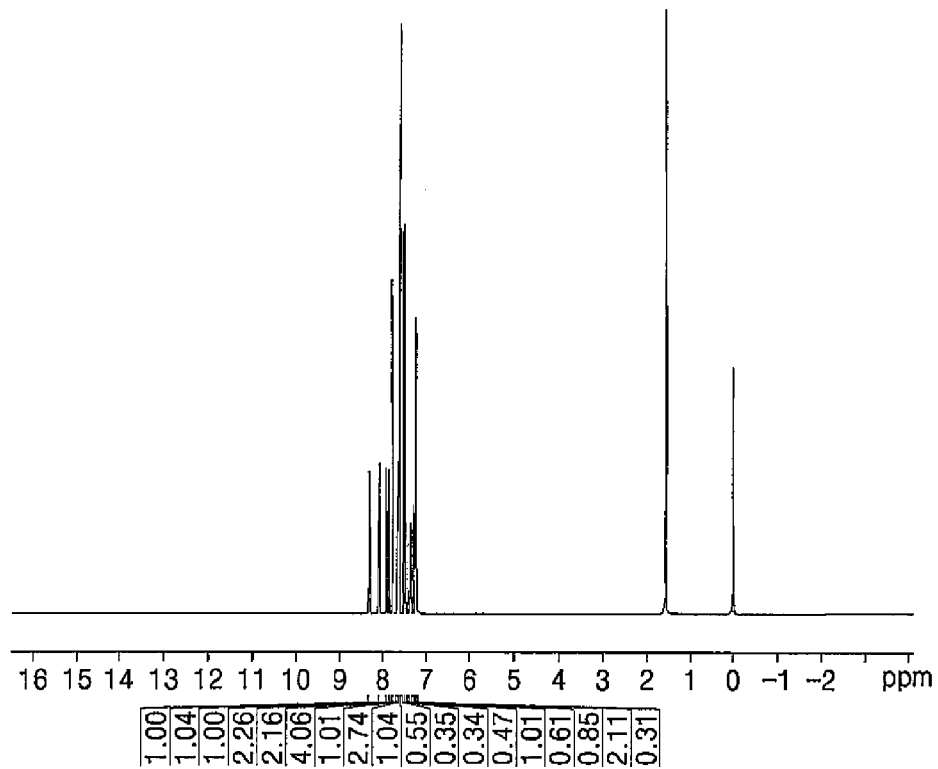
FIG. 2 is a nuclear magnetic resonance (NMR) spectrum of an anthracene derivative represented by Formula 8 according to an embodiment of the present invention.
Figure 3:
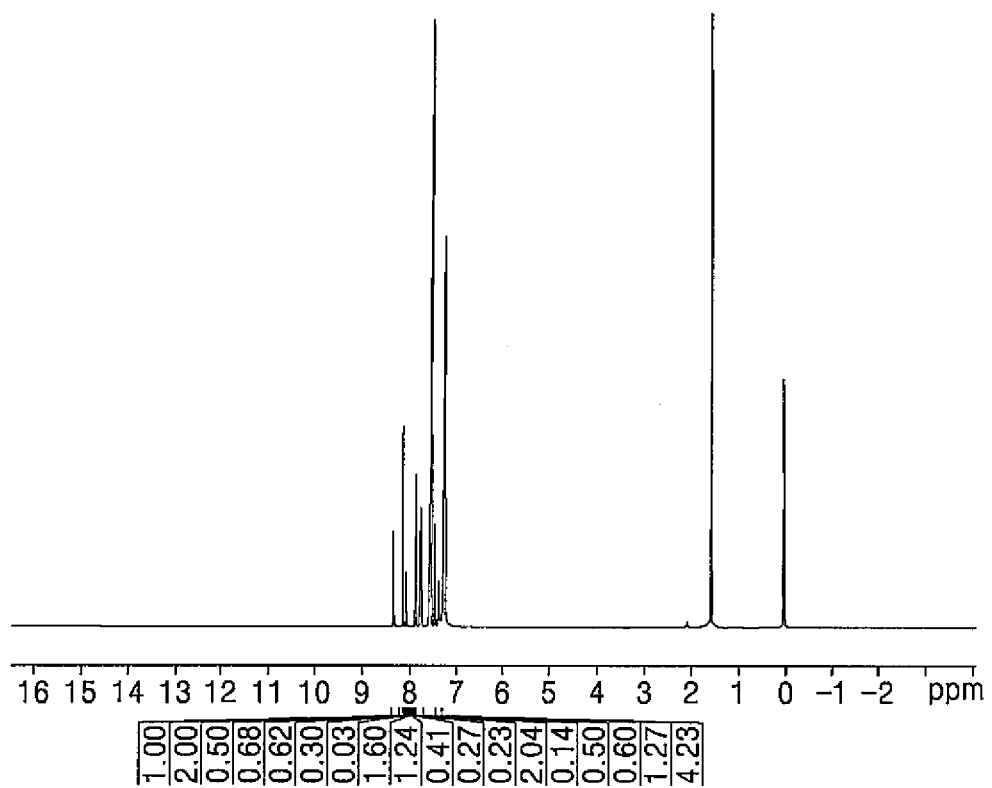
FIG. 3 is an NMR spectrum of an anthracene derivative represented by Formula 47 according to an embodiment of the present invention.

Anthracene derivatives represented by Formulae 8 and 47, respectively, were synthesized using syntheses similar to those described above. FIG. 2 is a nuclear magnetic resonance (NMR) spectrum of an anthracene derivative represented by Formula 8. FIG. 3 is an NMR spectrum of an anthracene derivative represented by Formula 47.

Example 1

Manufacturing an Organic Light-Emitting Device

An ITO glass was patterned to make an emission area of 2 mm×2 mm and then washed. The ITO glass was mounted on a vacuum chamber, a base pressure was set to 1×10$^{-7}$ torr, CuPc (800 Å) and α-NPD (300 Å) were sequentially deposited on the ITO glass, and a mixture of a compound represented by Formula 28 according to an embodiment of the present invention and 3% of BD1 (250 Å) was deposited. Then, Alq$_3$ (350 Å), LiF (5 Å), and Al (500 Å) were sequentially deposited thereon to manufacture an organic light-emitting device. Emission characteristics were measured at 0.4 mA. A structure of BD1 is shown below.

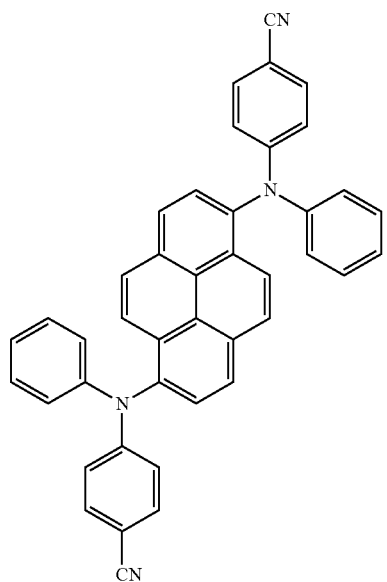

BD1

Examples 2 to 9

Manufacturing an Organic Light-Emitting Device

An organic light-emitting device was manufactured as in Example 1, except that a compound as disclosed in Table 1 was used instead of the compound represented by Formula 28. Emission characteristics of the organic light-emitting devices were measured at 0.4 mA.

Comparative Example 1

An organic light-emitting device was manufactured as in Example 1, except that BH1 was used instead of the compound represented by Formula 28. Emission characteristics of the organic light-emitting device were measured at 0.4 mA.

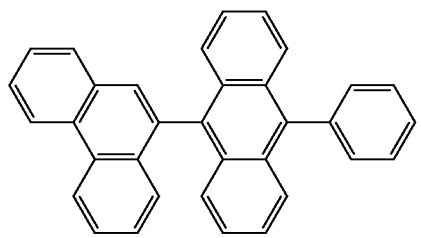

BH1

Comparative Example 2

An organic light-emitting device was manufactured as in Example 1, except that BH2 was used instead of the compound represented by Formula 28. Emission characteristics of the organic light-emitting device were measured at 0.4 mA.

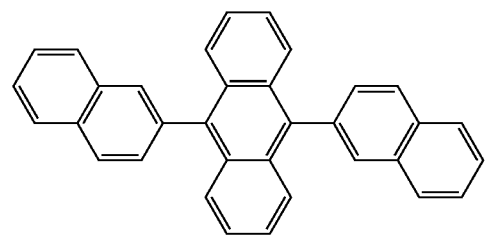

BH2

Figure 4:
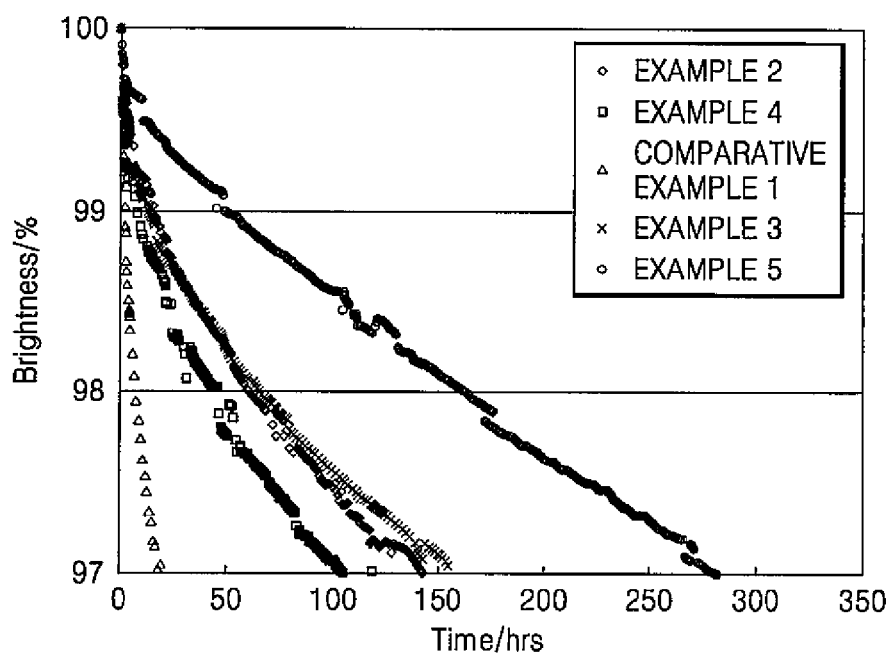
FIG. 4 is a graph showing a relative amount of change in brightness of organic light-emitting devices manufactured as in Examples 2-5 and Comparative Example 1, as compared to an initial brightness level thereof, according to time.
Figure 5:
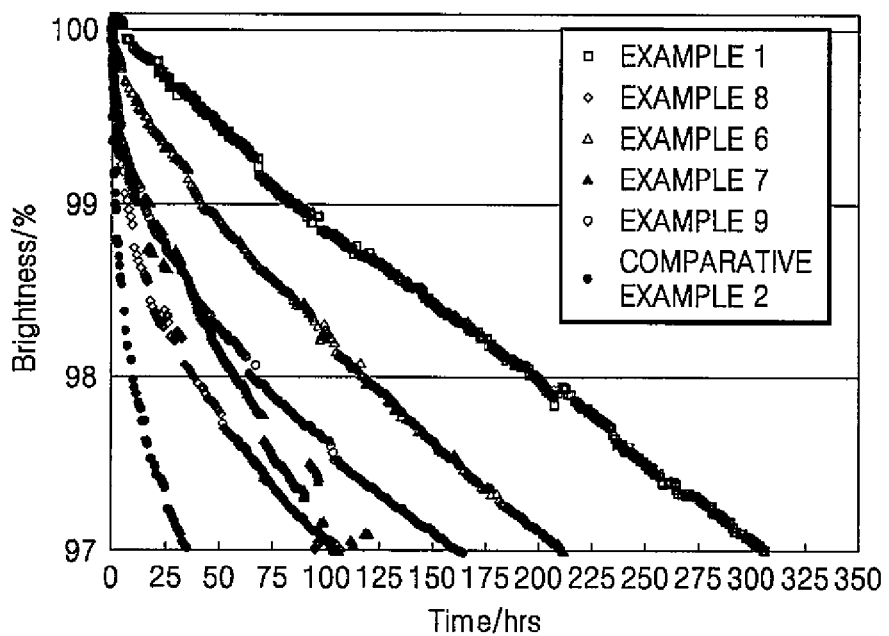
FIG. 5 is a graph showing a relative amount of change in brightness of organic light-emitting devices manufactured as in Examples 1 and 6 to 9, and Comparative Example 2, as compared to an initial brightness level thereof, according to time.

Voltages, currents, brightness, color coordinates, and lifespans of the organic light-emitting devices manufactured in Examples 1 to 9 and Comparative Examples 1 to 2 were measured and the results thereof are shown in Table 1 below. T80 refers to an amount of time that elapsed until brightness of the organic light-emitting device reached 80% of the initial brightness thereof. FIG. 4 is a graph showing a relative amount of change in brightness of organic light-emitting devices manufactured as in Examples 2-5 and Comparative Example 1, as compared to an initial brightness level thereof, according to time, and FIG. 5 is a graph showing a relative amount of change in brightness of organic light-emitting devices manufactured as in Examples 1 and 6 to 9, and Comparative Example 2, as compared to an initial brightness level thereof, according to time

TABLE 1

| | Voltage | Current density (mA/Cd/m$^2$) | Brightness (cd/m$^2$) | CIEx | CIEy | T80 |
|---|---|---|---|---|---|---|
| Example 1 Formula 28 | 3.7 | 10 | 752 | 0.14 | 0.11 | 300 |
| Example 2 Formula 33 | 3.7 | 10 | 683 | 0.14 | 0.12 | 140 |
| Example 3 Formula 36 | 3.8 | 10 | 651 | 0.14 | 0.11 | 153 |
| Example 4 Formula 59 | 3.7 | 10 | 813 | 0.14 | 0.13 | 100 |
| Example 5 Formula 60 | 3.8 | 10 | 578 | 0.14 | 0.10 | 283 |
| Example 6 Formula 63 | 3.7 | 10 | 717 | 0.14 | 0.11 | 211 |
| Example 7 Formula 67 | 3.7 | 10 | 873 | 0.14 | 0.13 | 110 |

TABLE 1-continued

|  | Voltage | Current density (mA/Cd/m²) | Brightness (cd/m²) | CIEx | CIEy | T80 |
|---|---|---|---|---|---|---|
| Example 8 Formula 83 | 3.8 | 10 | 648 | 0.14 | 0.12 | 105 |
| Example 9 Formula 101 | 3.7 | 10 | 840 | 0.14 | 0.13 | 166 |
| Comparative Example 1 BH1 | 4.8 | 10 | 530 | 0.14 | 0.12 | 23 |
| Comparative Example 2 BH2 | 4.7 | 10 | 560 | 0.14 | 0.12 | 30 |

As shown in Table 1 above, and FIGS. 4 and 5, an organic light-emitting device including an anthracene derivative according to an embodiment of the present invention has better brightness and emission efficiency and longer lifespan than those of the Comparative Examples.

As described above, according to aspects of one or more embodiments of the present invention, an organic light-emitting device including an anthracene derivative according to an embodiment of the present invention has good color purity, brightness, emission efficiency, and lifespan characteristics and thus, may be useful for an indicating device, a display device, and lights.

It should be understood that the embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the accompanying drawings, it will be understood by those of ordinary skill in the art that various changes may be made to the described embodiments without departing from the spirit and scope of the present invention as defined by the following claims.

What is claimed is:

1. An anthracene derivative comprising at least one compound represented by Formula 28 to Formula 107:

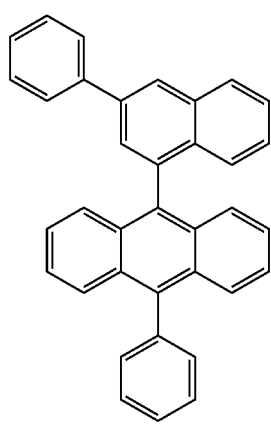

Formula 28

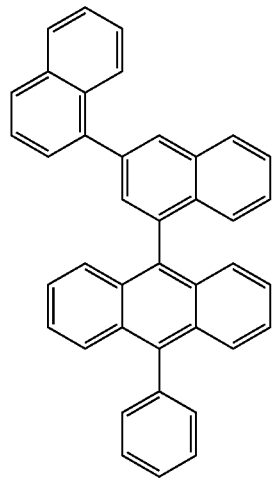

Formula 29

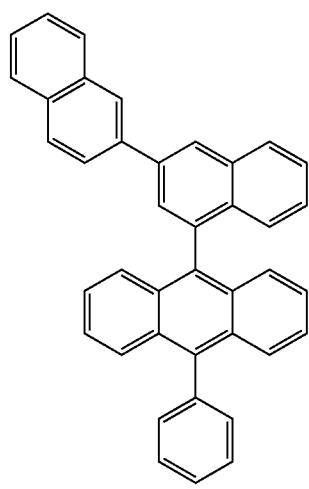

Formula 30

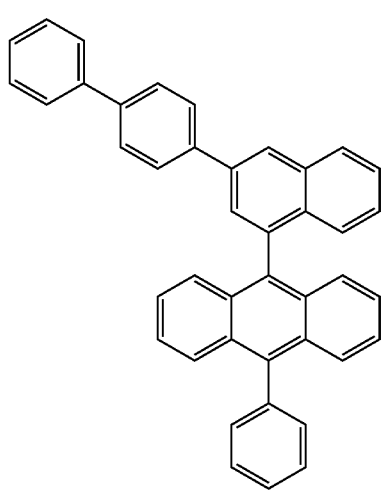

Formula 31

-continued
Formula 32
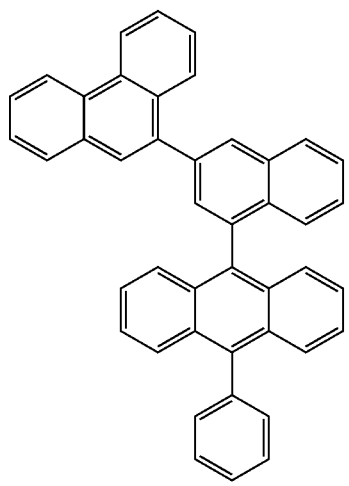
Formula 33
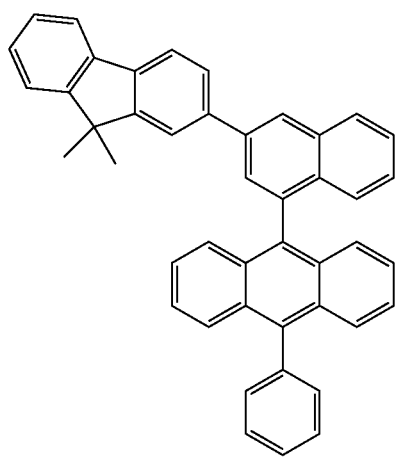
Formula 34
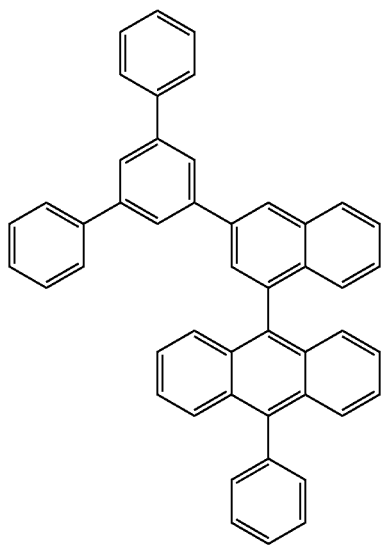
-continued
Formula 35
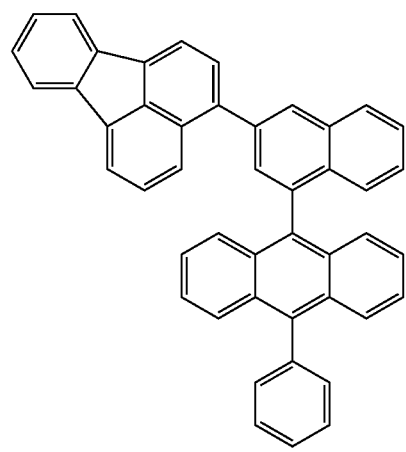
Formula 36
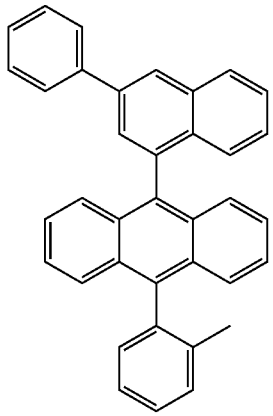
Formula 37
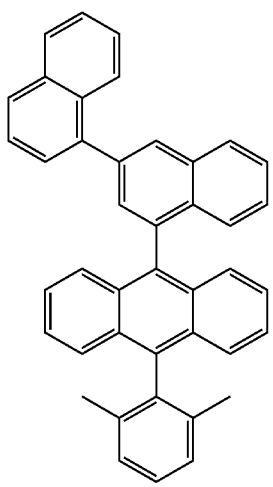

-continued
Formula 38
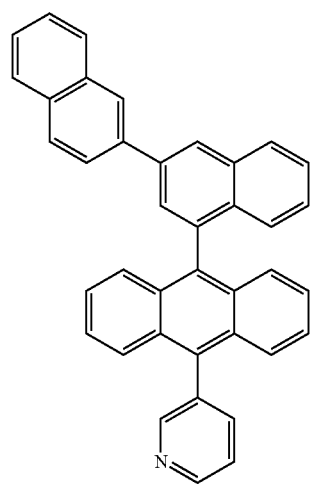
Formula 39
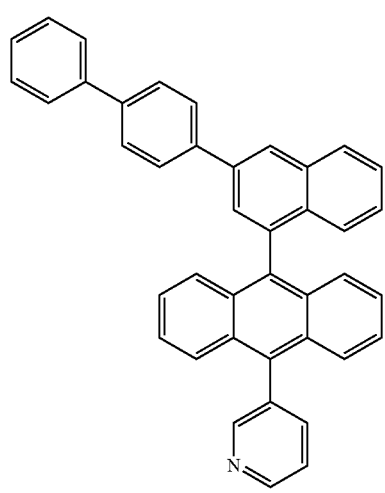
Formula 40
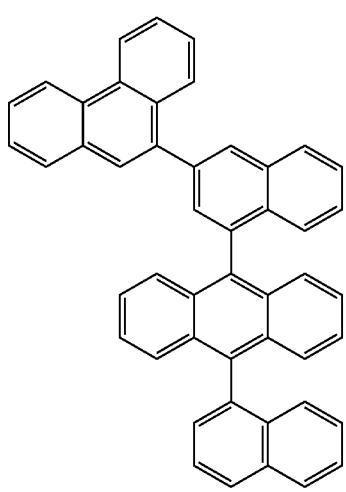
-continued
Formula 41
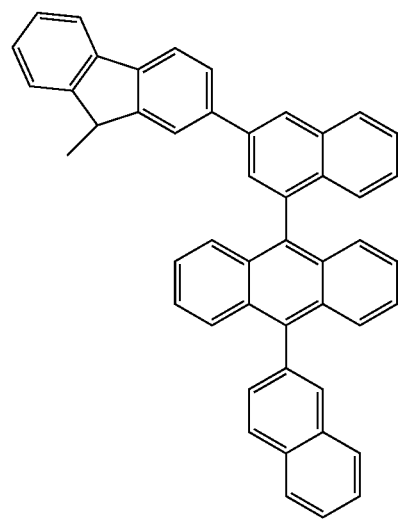
Formula 42
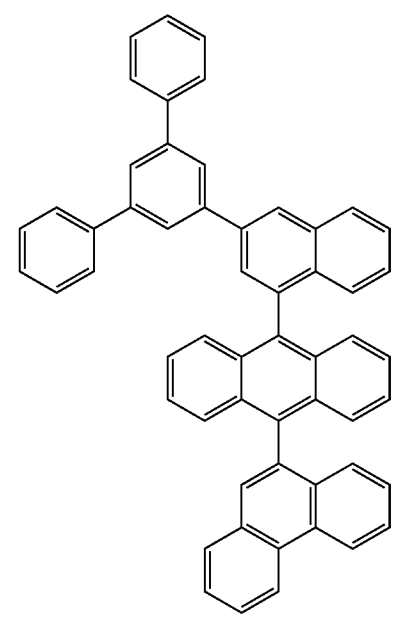
Formula 43
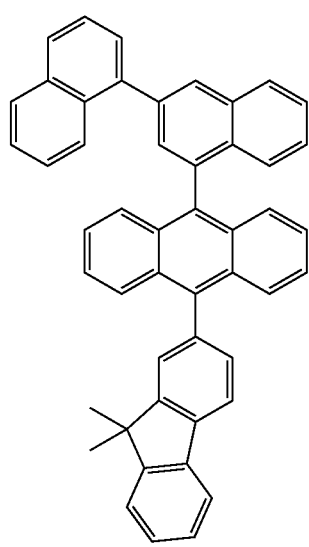

Formula 44
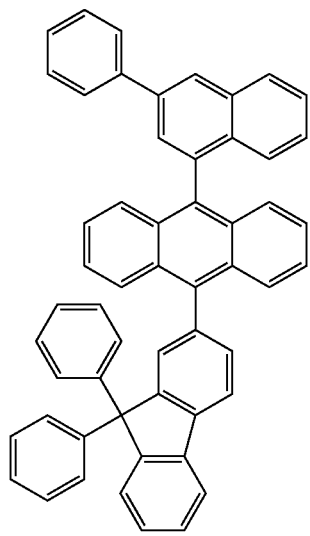
Formula 45
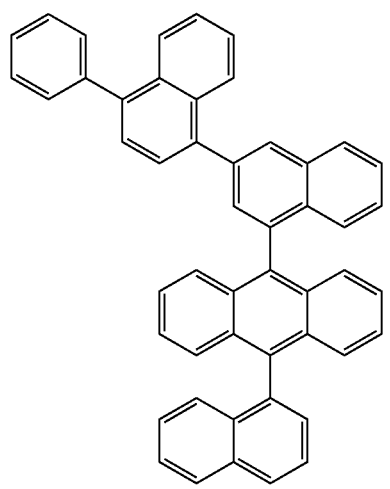
Formula 46
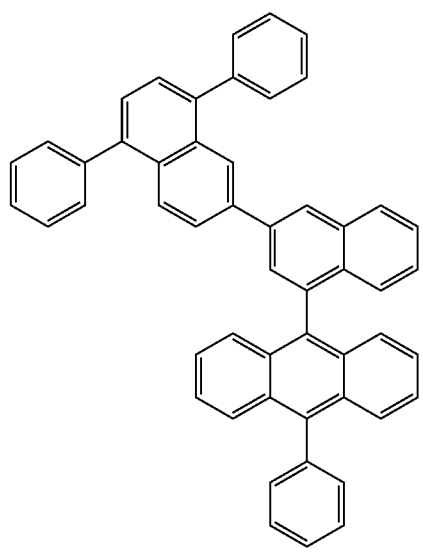
Formula 47
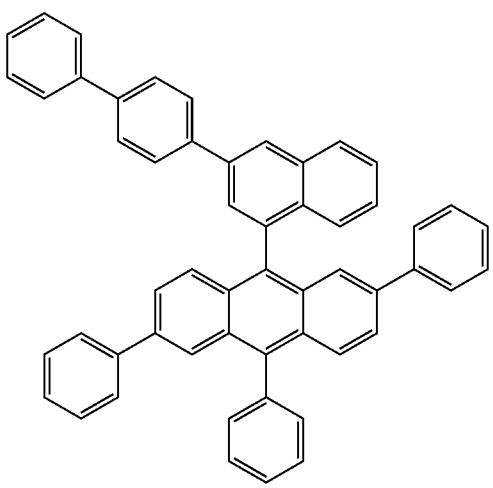
Formula 48
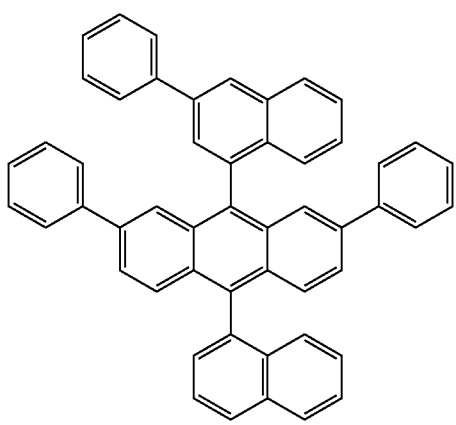
Formula 49
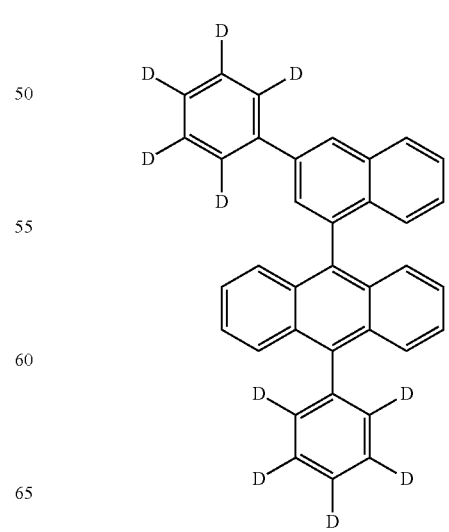

Formula 50
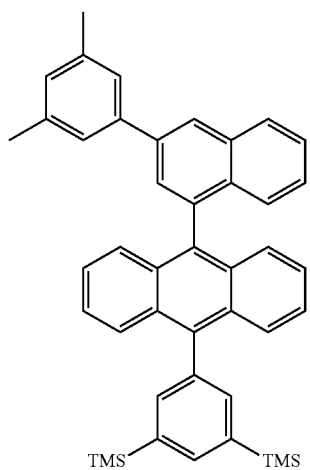
Formula 51
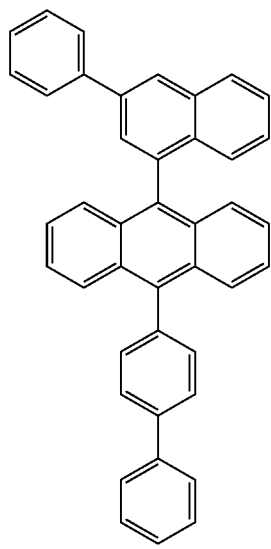
Formula 52
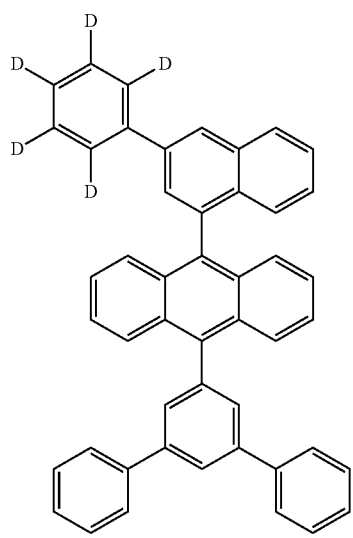
Formula 53
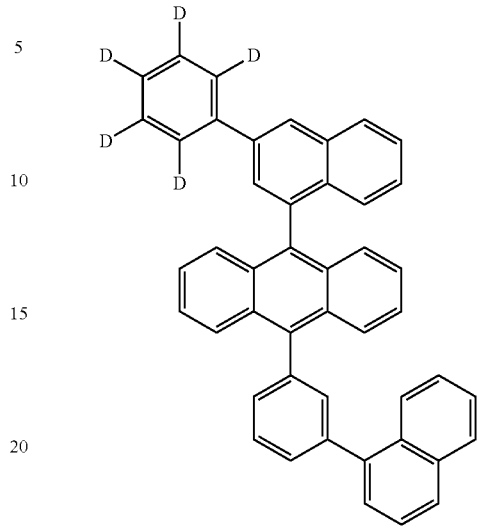
Formula 54
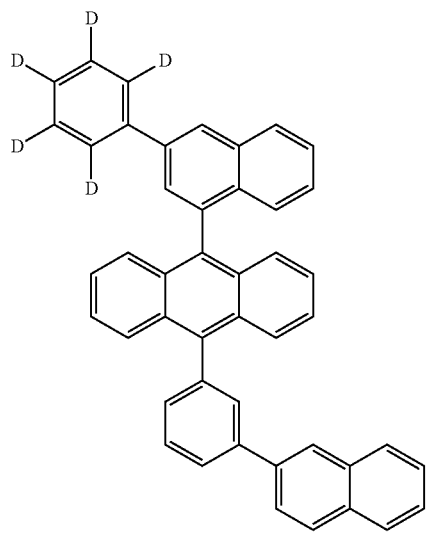

Formula 55
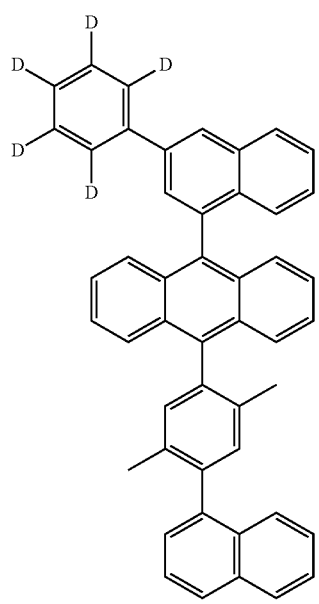
Formula 56
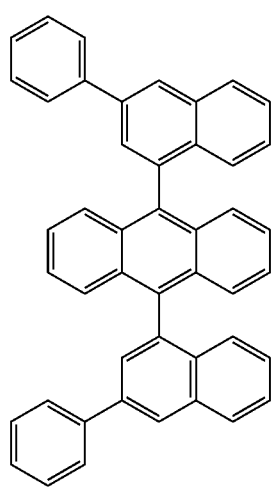
Formula 57
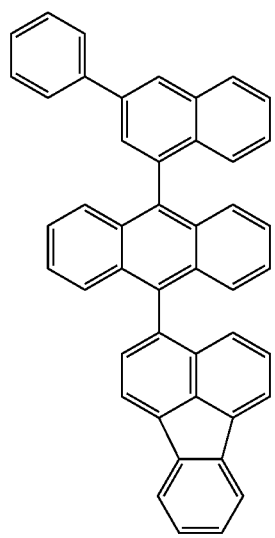
Formula 58
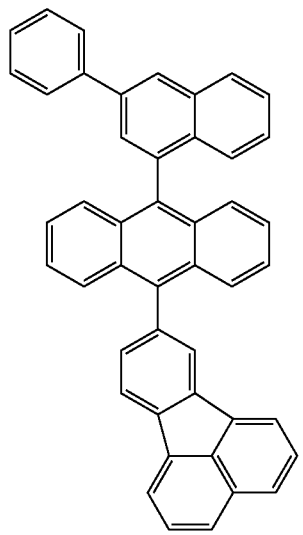
Formula 59
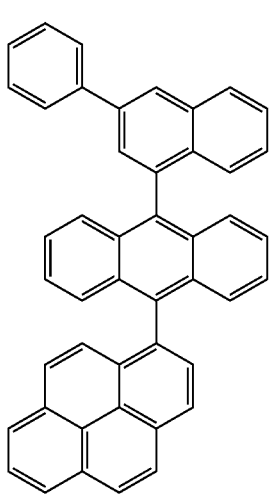
Formula 60
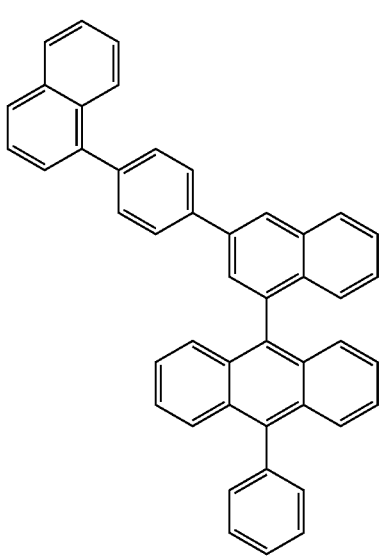

Formula 61
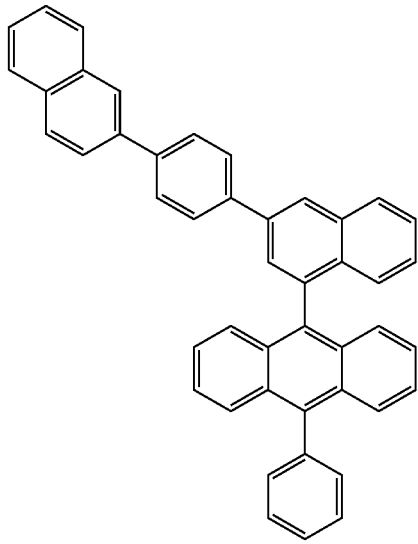
Formula 62
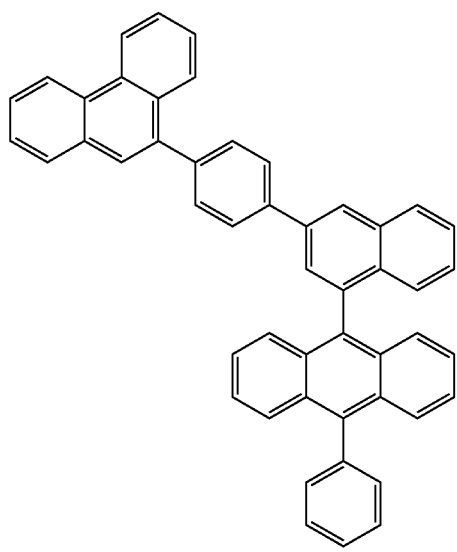
Formula 63
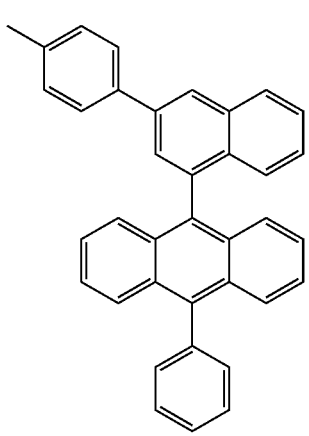
Formula 64
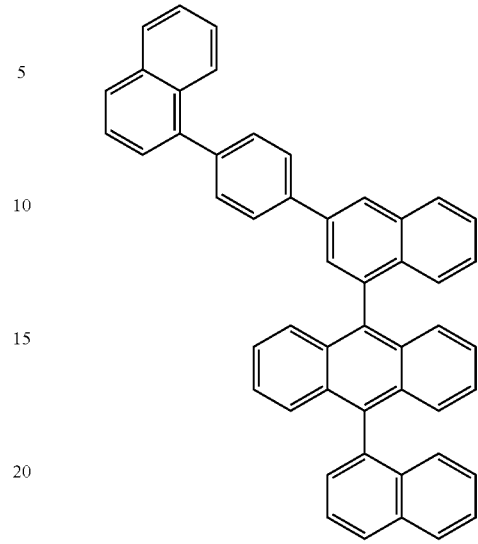
Formula 65
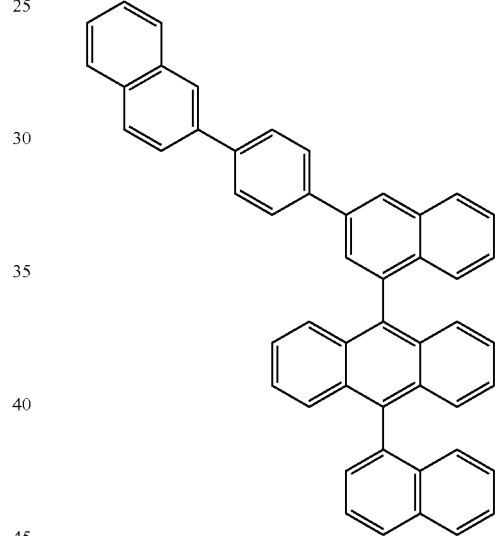
Formula 66
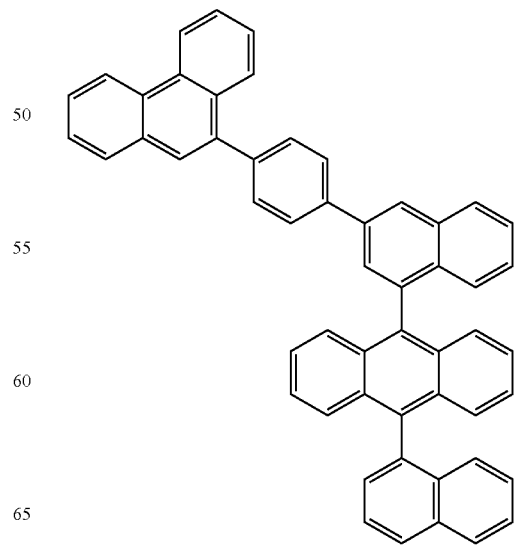

Formula 67
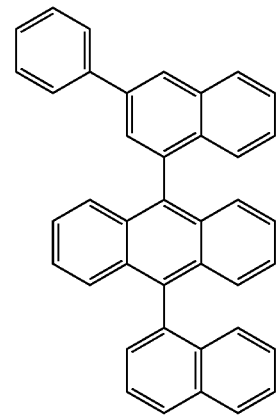
Formula 68
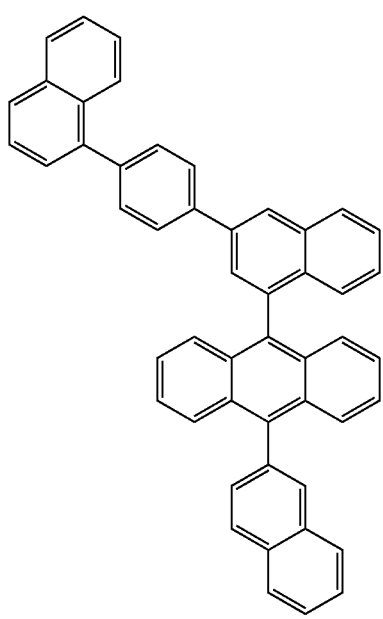
Formula 69
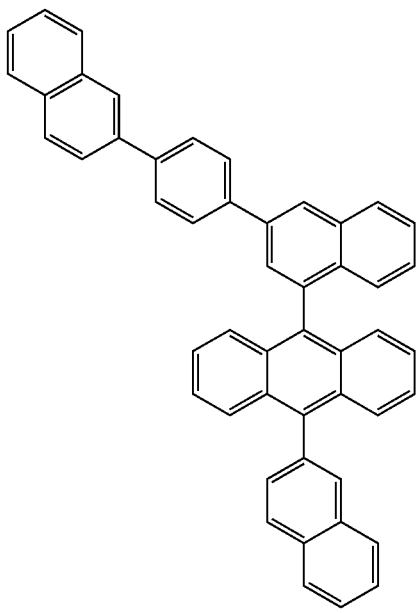
Formula 70
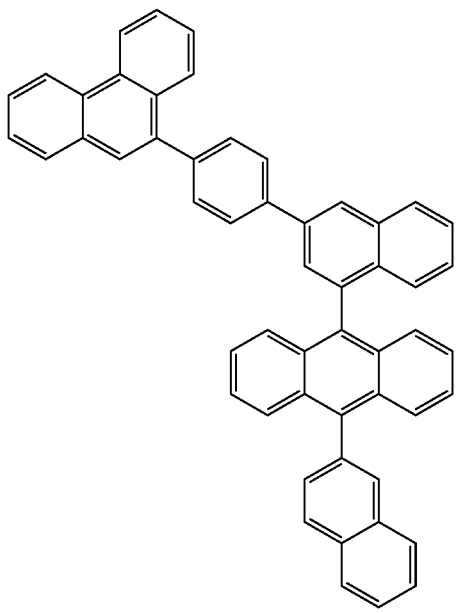
Formula 71
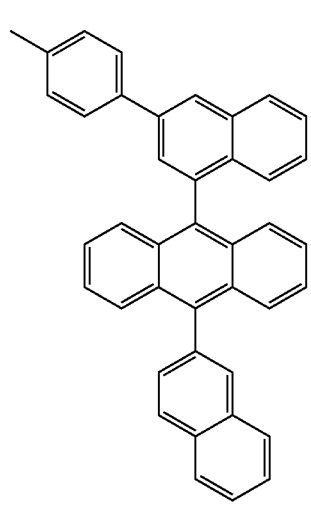

Formula 72
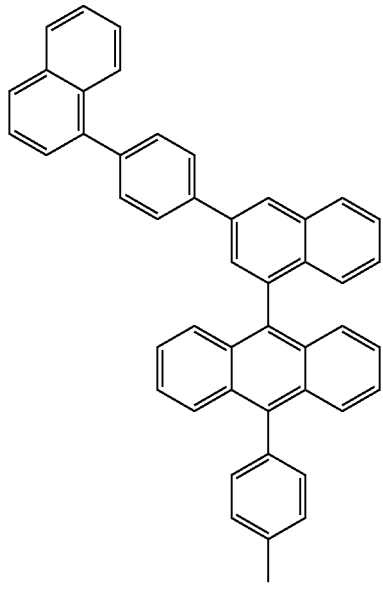
Formula 73
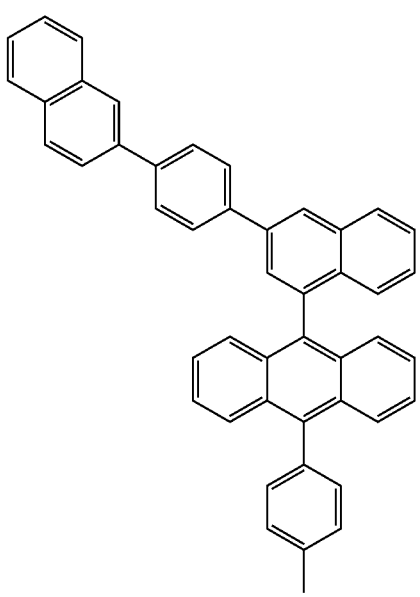
Formula 74
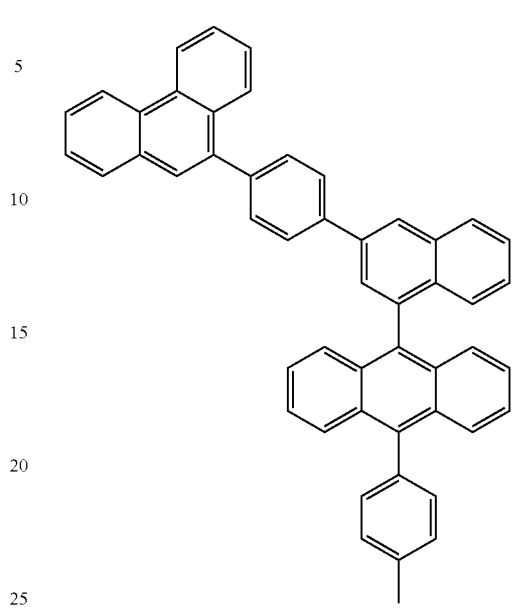
Formula 75
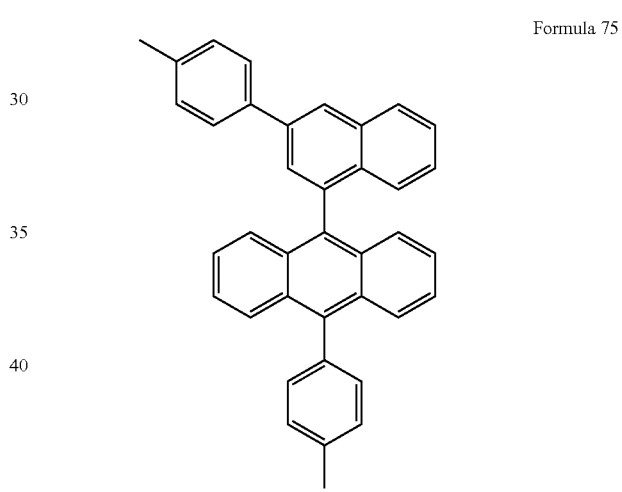
Formula 76
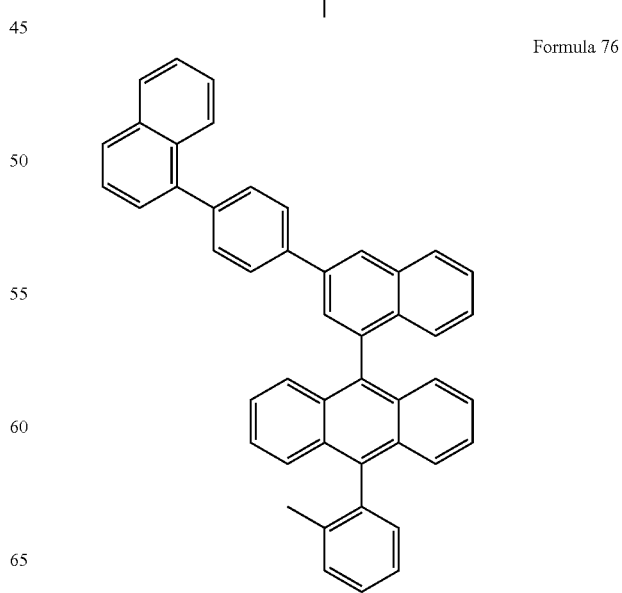

Formula 77
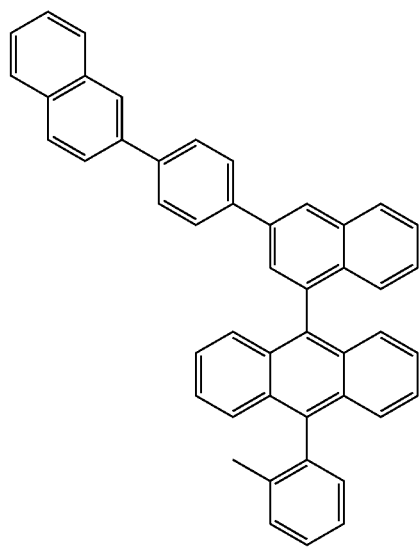
Formula 78
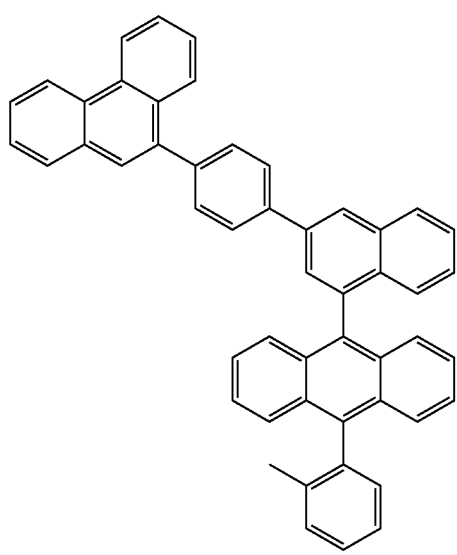
Formula 79
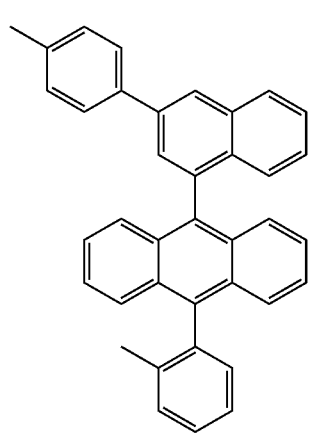
Formula 80
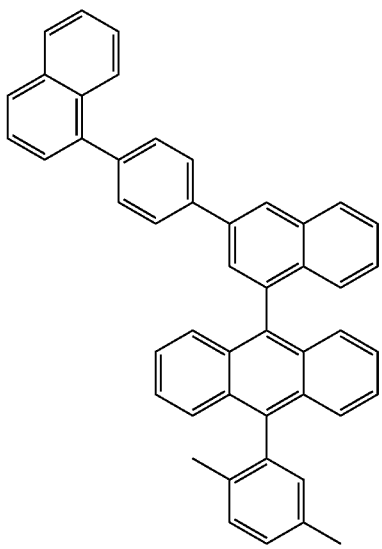
Formula 81
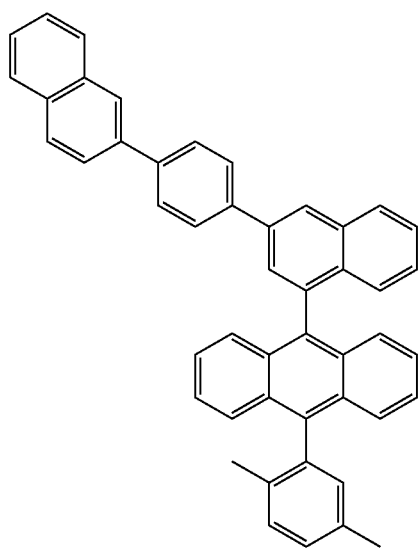

Formula 82
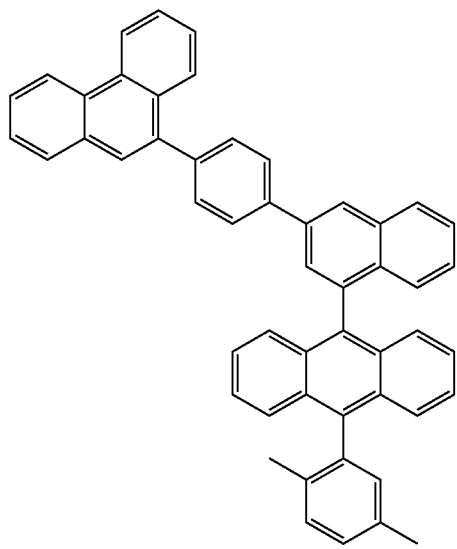
Formula 83
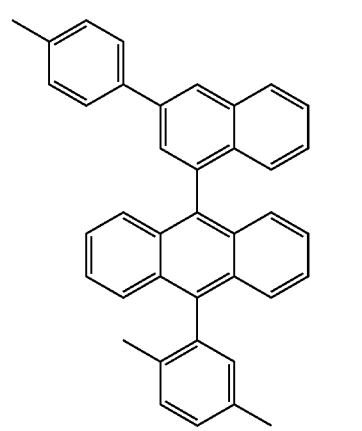
Formula 84
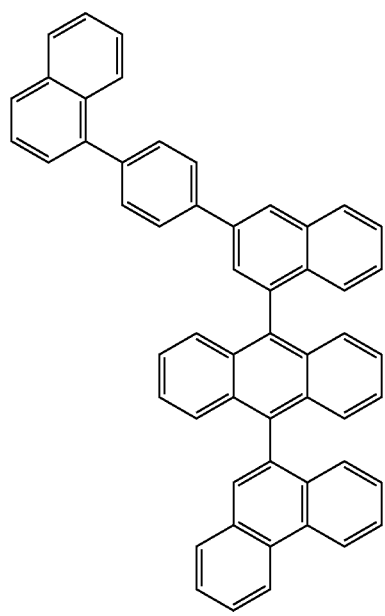
Formula 85
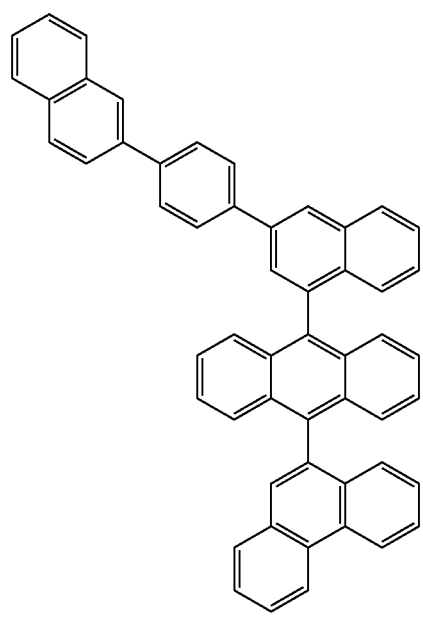
Formula 86
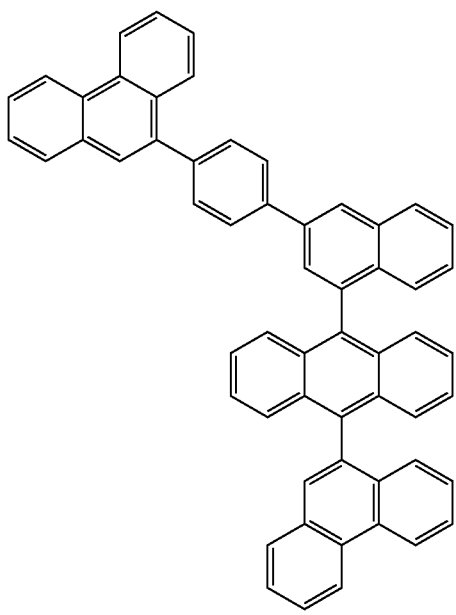

99
-continued
Formula 87
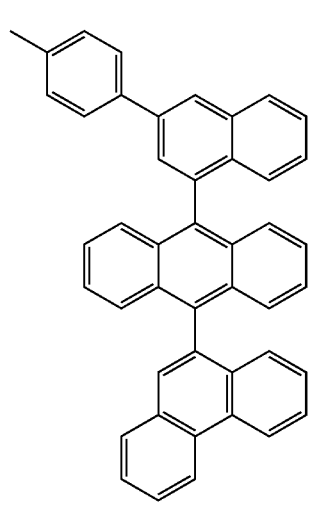
Formula 88
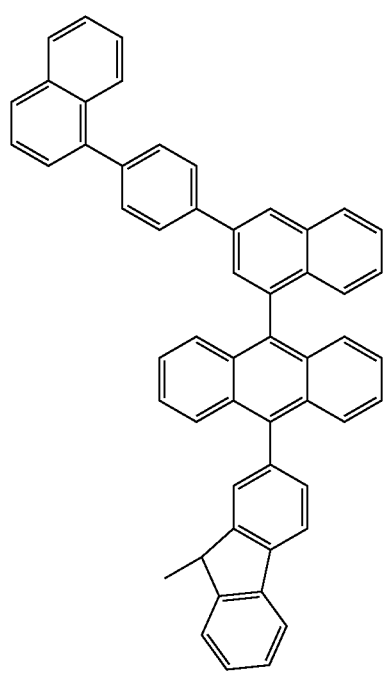
100
-continued
Formula 89
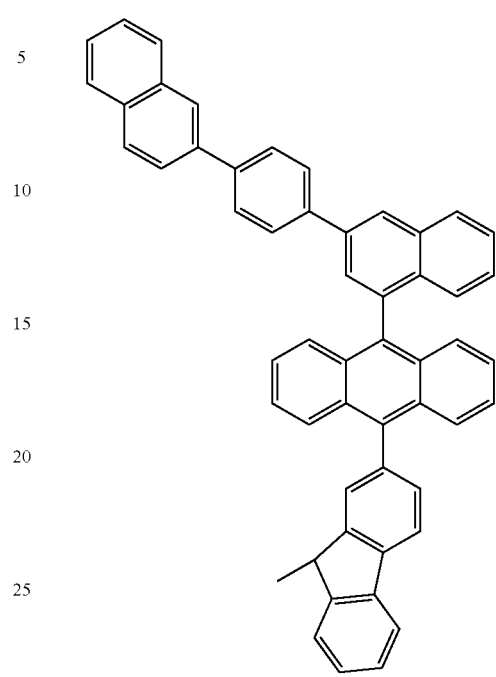
Formula 90
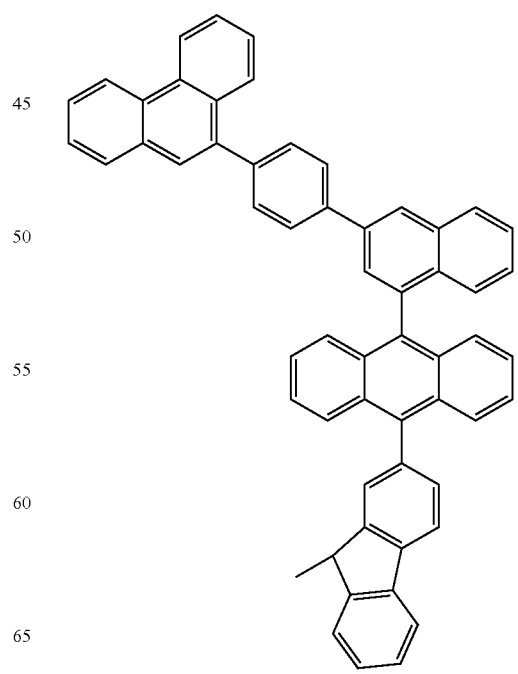

Formula 91
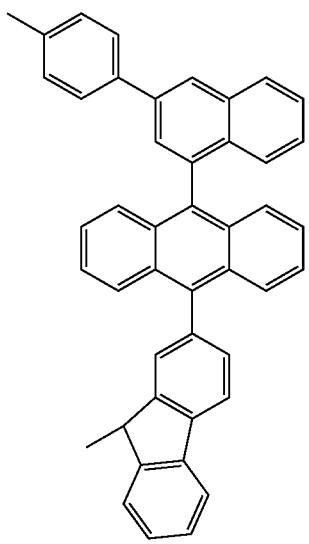
Formula 92
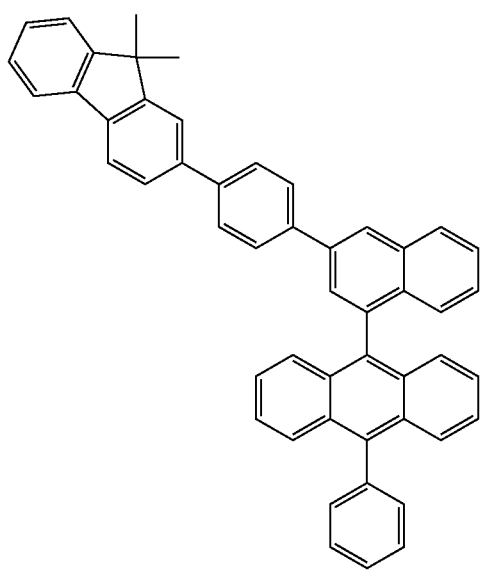
Formula 93
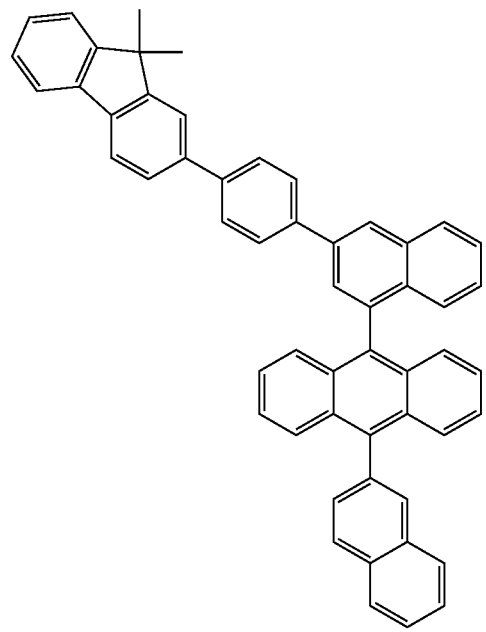
Formula 94
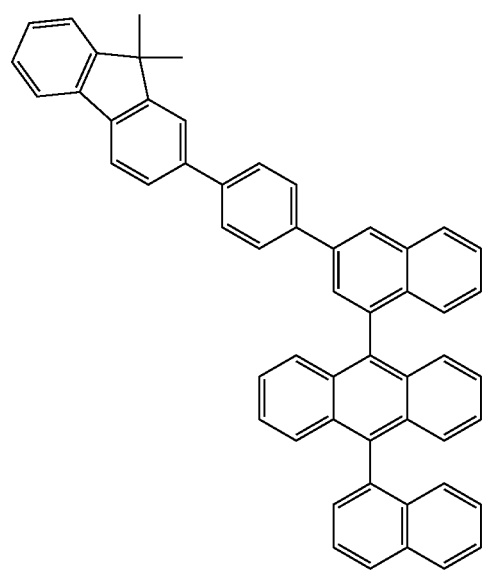

Formula 95
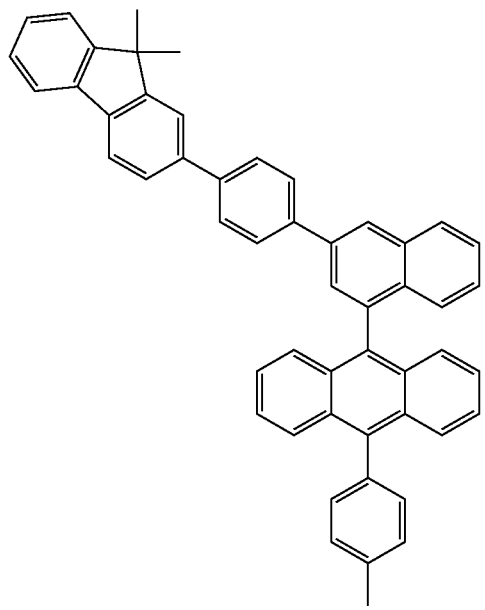
Formula 96
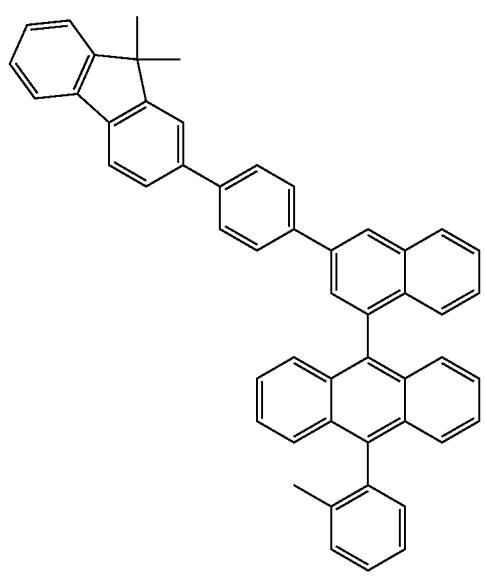
Formula 97
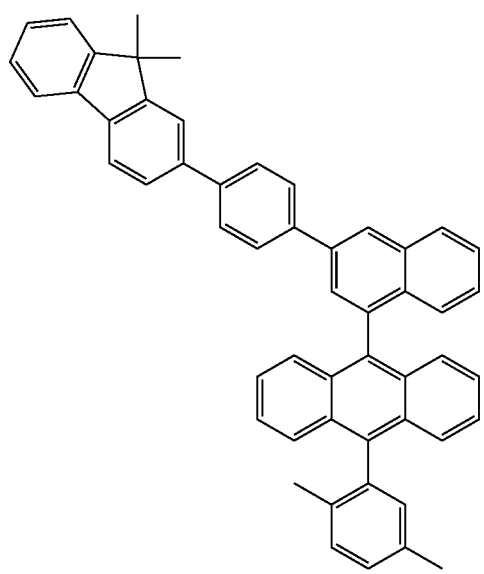
Formula 98
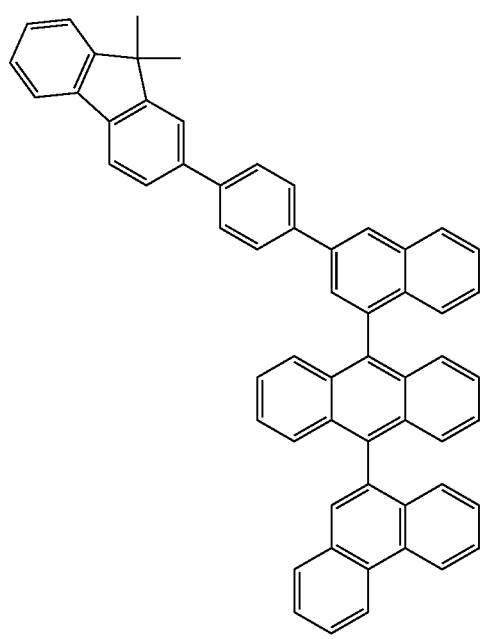

Formula 99
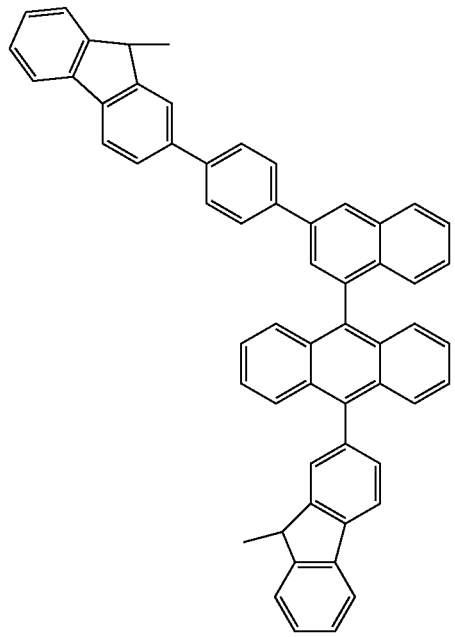
Formula 100
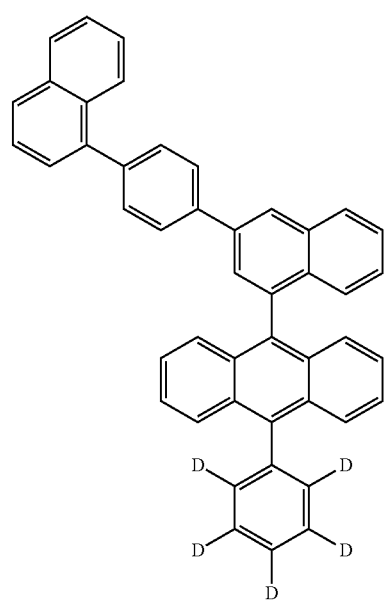
Formula 101
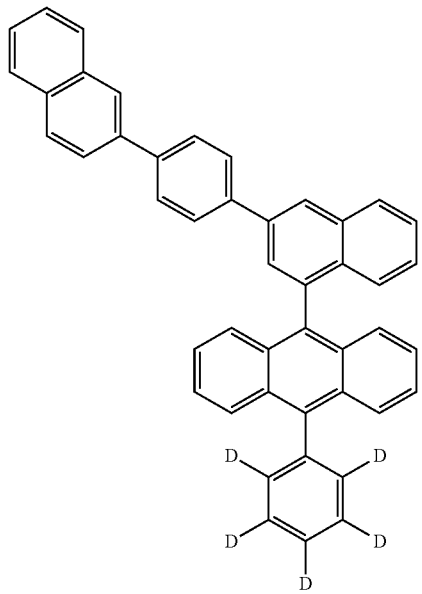
Formula 102
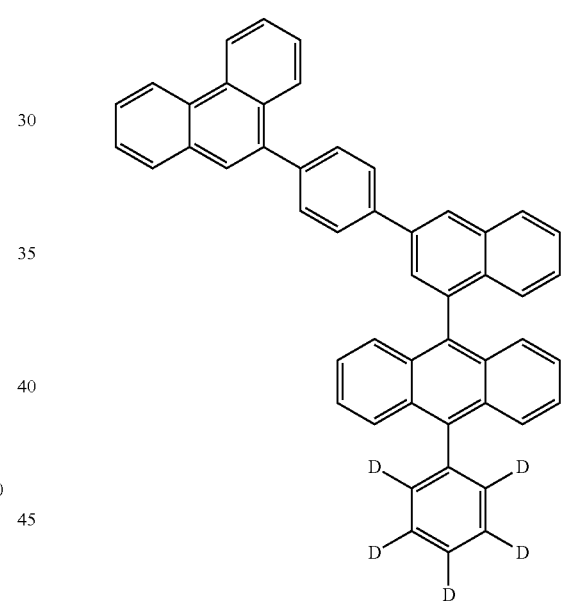
Formula 103
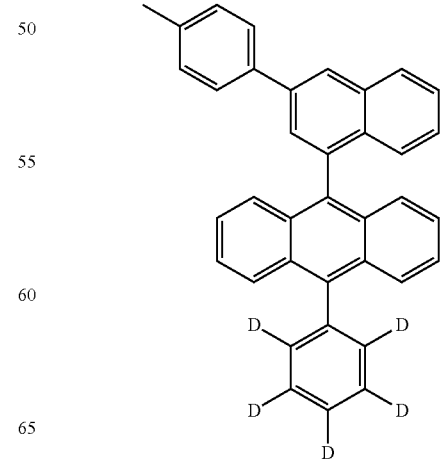

Formula 104

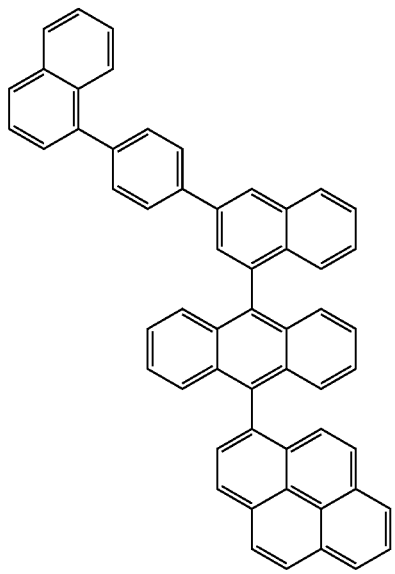

Formula 105

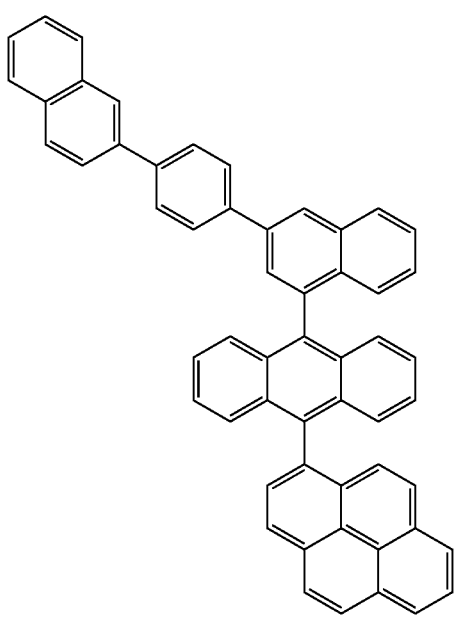

Formula 106

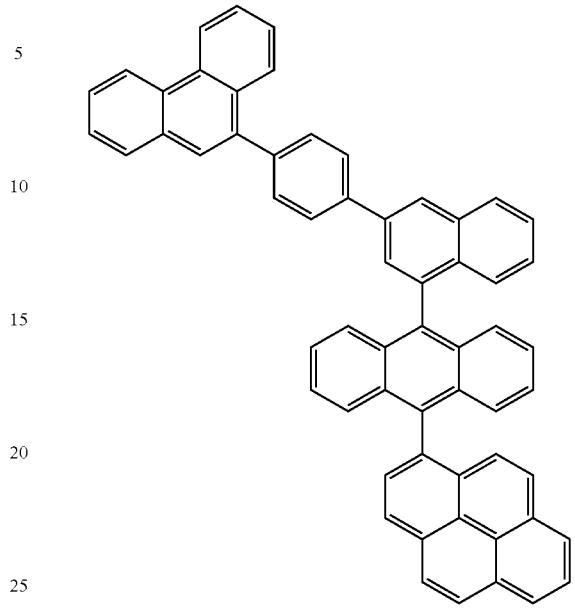

Formula 107

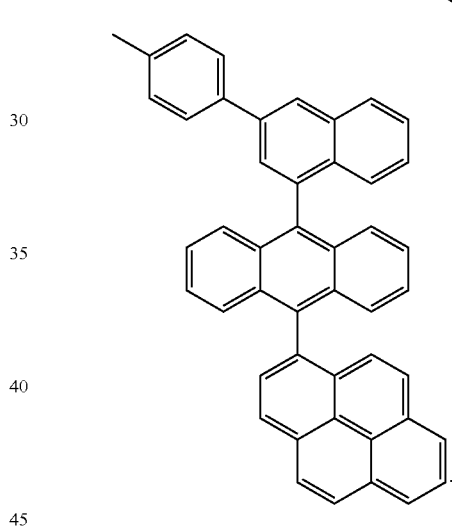

2. An organic light-emitting device comprising:
an anode;
a cathode; and
an organic layer between the anode and the cathode;
wherein the organic layer comprises at least one anthracene derivative according to claim 1.

3. The organic light-emitting device of claim 2, wherein:
the organic layer comprises a single layer or a plurality of layers comprising an emission layer, and further comprises at least one of a hole-injecting layer, a hole-transporting layer, an electron-transporting layer, or an electron-injecting layer, and
the emission layer comprises the at least one anthracene derivative.

4. The organic light-emitting device of 3, wherein the emission layer comprises the at least one anthracene derivative as a host and further comprises at least one dopant compound.

5. The organic light-emitting device of claim 2, wherein the organic light-emitting device comprises at least one emission layer configured to emit white light comprising blue, red, or green light.

* * * * *